United States Patent
Peterson

(10) Patent No.: US 10,766,928 B2
(45) Date of Patent: *Sep. 8, 2020

(54) TARGETED CONFORMATIONALLY-CONSTRAINED KINKED ENDOSOMAL DISRUPTING PEPTIDES

(71) Applicant: The University of Kansas, Lawrence, KS (US)

(72) Inventor: Blake R. Peterson, Lawrence, KS (US)

(73) Assignee: The University of Kansas, Lawrence, KS (US)

(*) Notice: Subject to any disclaimer, the term of this patent is extended or adjusted under 35 U.S.C. 154(b) by 515 days.

This patent is subject to a terminal disclaimer.

(21) Appl. No.: 15/480,120

(22) Filed: Apr. 5, 2017

(65) Prior Publication Data

US 2017/0218022 A1 Aug. 3, 2017

Related U.S. Application Data

(63) Continuation-in-part of application No. 14/438,194, filed as application No. PCT/US2013/063250 on Oct. 3, 2013, now Pat. No. 9,701,715.

(60) Provisional application No. 61/710,289, filed on Oct. 5, 2012, provisional application No. 62/319,159, filed on Apr. 6, 2016.

(51) Int. Cl.
| | |
|---|---|
| *A61K 38/00* | (2006.01) |
| *C07K 7/08* | (2006.01) |
| *C07K 16/32* | (2006.01) |
| *A61K 47/54* | (2017.01) |
| *A61K 47/65* | (2017.01) |
| *A61K 47/68* | (2017.01) |
| *C07K 16/28* | (2006.01) |

(52) U.S. Cl.
CPC .............. *C07K 7/08* (2013.01); *A61K 47/554* (2017.08); *A61K 47/65* (2017.08); *A61K 47/6811* (2017.08); *A61K 47/6849* (2017.08); *A61K 47/6851* (2017.08); *A61K 47/6889* (2017.08); *C07K 16/2887* (2013.01); *C07K 16/32* (2013.01); *C07K 2317/24* (2013.01); *C07K 2317/73* (2013.01); *C07K 2319/06* (2013.01); *C07K 2319/74* (2013.01)

(58) Field of Classification Search
CPC ................................ C07K 7/08; A61K 47/6889
See application file for complete search history.

(56) References Cited

U.S. PATENT DOCUMENTS

| | | | |
|---|---|---|---|
| 6,825,319 B1 | 11/2004 | Blank et al. | |
| 9,701,715 B2* | 7/2017 | Peterson | A61K 47/42 |
| 2006/0229235 A1 | 10/2006 | Peterson | |
| 2008/0012157 A1 | 1/2008 | Kandiyeli et al. | |
| 2008/0039404 A1 | 2/2008 | Hruby et al. | |
| 2010/0041773 A1 | 2/2010 | Peterson | |
| 2011/0230420 A1 | 9/2011 | Zhao et al. | |

FOREIGN PATENT DOCUMENTS

| | | |
|---|---|---|
| CA | 1340656 | 7/1999 |
| WO | 2006052723 A2 | 5/2006 |
| WO | 2011019942 A2 | 2/2011 |

OTHER PUBLICATIONS

Sun et al. J Am Chem Soc. Aug. 6, 2008; 130(31): 10064-10065.*
Sun et al., Selective Disruption of Early/Recycling Endosomes: Release of Disulfide-Linked Cargo Mediated by a N-Alkyl-3β-Cholesterylamine-Capped Peptide, Journal of the American Chemical Society 2008 130 (31), 10064-10065 DOI: 10.1021/ja803380a (2 pages).
Peterson, Blake R., Synthetic mimics of mammalian cell surface receptors: prosthetic molecules that augment living cells, Org. Biomol. Chem., 2005,3, 3607-3612, DOI: 10.1039/B509866A, Received Jul. 5, 2005, Accepted Aug. 11, 2005 First published online Sep. 8, 2005 (6 pages).
Hymel, et al., Synthetic cell surface receptors for delivery of therapeutics and probes, Department of Medicinal Chemistry, The University of Kansas, Lawrence, KS 66045, USA Received Dec. 23, 2011, Accepted Feb. 20, 2012, Available online Feb. 25, 2012 (14 pages).
Shiraishi et al. Enhanced delivery of cell-penetrating peptide-peptide nucleic acid conjugates by endosomal disruption. Nat Protoc. 2006;1(2):633-6.
Nakase et al. Endosome-Disruptive Peptides for Improving Cytosolic Delivery of Bioactive Macromolecules. Biopolymers. 2010; 94(6):763-70.
Chakrabartty et al. Helix propensities of the amino acids measured in alanine-based peptides without helix-stabilizing side-chain interactions. Protein Science. 1994; 3:843-852.
Marshall et al.; Factors governing helical preference of peptides containing multiple α,α-dialkyl amino acids; Proc. Natl. Acad. Sci. USA; Jan. 1990; vol. 87, pp. 487-491.

(Continued)

*Primary Examiner* — Jeanette M Lieb
(74) *Attorney, Agent, or Firm* — Maschoff Brennan; Jonathan M. Benns

(57) ABSTRACT

A peptide can have a sequence of one of SEQ ID NOs: 78-91. A conformationally-constrained kinked peptide includes: a conformationally-constraining portion and a kinked portion linked to the conformationally-constraining portion that conformationally constrains the kinked portion having a peptide sequence of one of SEQ NOs: 78-97. A cell-targeting compound can include a conformationally-constrained kinked peptide having a peptide sequence of one of SEQ ID NOs: 78-97. The peptide sequence can be one of SEQ ID NOs: 78-97, or 78-91, or 92-97. A cell-targeting compound can include a conformationally-constrained kinked peptide linked to a branched linker with one branch arm linked to a specific targeting moiety and one branch arm linked to a general targeting moiety. The specific targeting moiety can be an antibody. The general targeting moiety can be a lipid or cholesterol derivative.

25 Claims, 18 Drawing Sheets

Specification includes a Sequence Listing.

(56) References Cited

OTHER PUBLICATIONS

Lyu et al.; α-Helix stabilization by natural and unnatural amino acids with alkyl side chains; Proc. Natl. Acad. Sci. USA; Jun. 1991; vol. 88, pp. 5317-5320.

Schafmeister et al.; An All-Hydrocarbon Cross-Linking System for Enhancing the Helicity and Metabolic Stability of Peptides; J. Am. Chem. Soc.; 2000; vol. 122, pp. 5891-5892.

Flint et al. Using an Azobenzene Cross-Linker to Either Increase or Decrease Peptide Helix Content upon Trans-to-Cis Photoisomerization. Chemistry and Biology. Mar. 2002; vol. 9, pp. 391-397.

Suh et al; Structural and functional implications of a proline residue in the antimicrobial peptide gaegurin; Eur. J. Biochem; 1999; vol. 266, pp. 665-674.

Richardson et al. Amino Acid Preferences for Specific Locations at the Ends of α Helices. Science. Jun. 17, 1988; vol. 240, pp. 1648-1652.

Galloux et al. NMR Structure of a Viral Peptide Inserted in Artificial Membranes. The Journal of Biological Chemistry. Jun. 18, 2010; vol. 285, No. 25, pp. 19409-19421.

Boonyarattanakalin et al.; Endocytic Delivery of Vancomycin Mediated by a Synthetic Cell Surface Receptor: Rescue of Bacterially Infected Mammalian Cells and Tissue Targeting In Vivo; J. Am. Chem. Soc.; 2007; vol. 129, pp. 268-269.

Jaworski et al. Detection of new sequences of peptaibol antibiotics trichotoxins A-40 by on-line liquid chromatography-electrospray ionization mass spectrometry. Journal of Chromatography A, 862 (1999) 179-189.

Raj et al. Conformations and Mitochondrial Uncoupling Activity of Synthetic Emerimicin Fragments. Biopolymers, vol. 27, 683-701 (1988).

\* cited by examiner

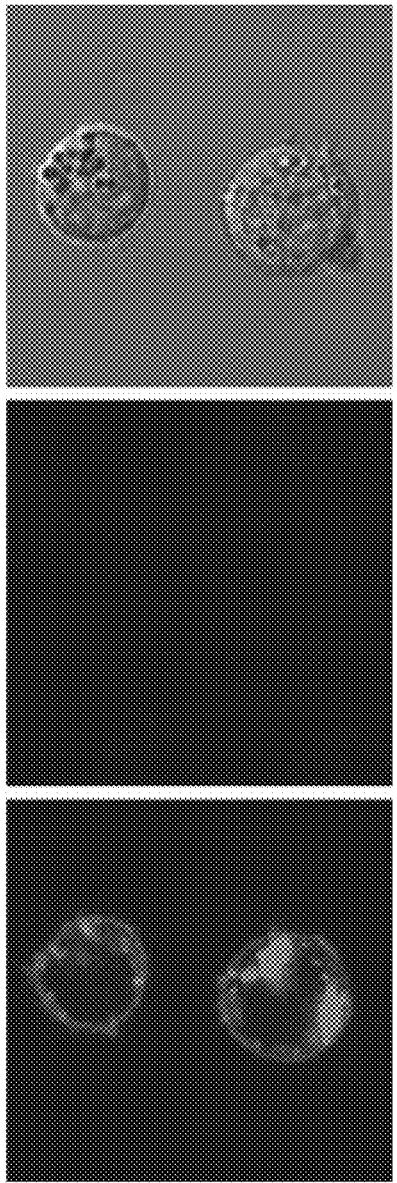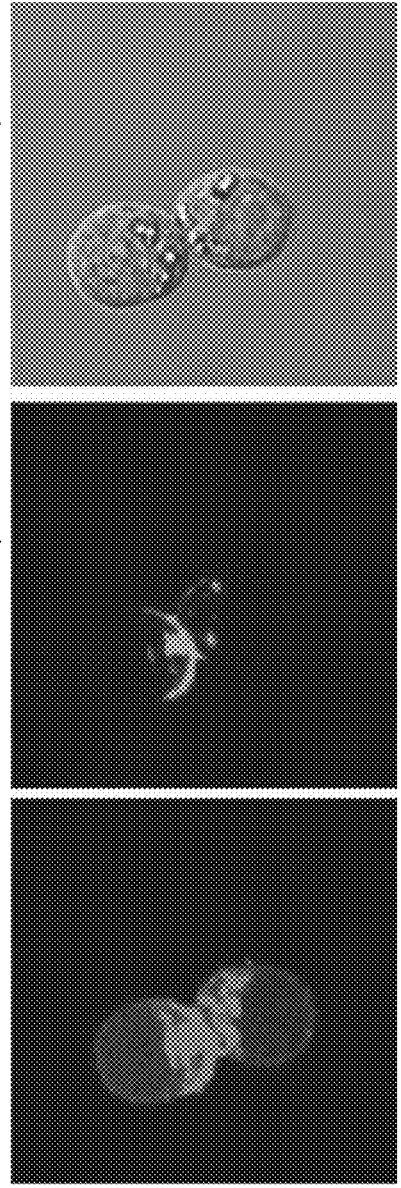

TARGETED CONFORMATIONALLY-CONSTRAINED KINKED ENDOSOMAL DISRUPTING PEPTIDES

CROSS-REFERENCE TO RELATED APPLICATIONS

This patent application is a continuation-in-part of U.S. Pat. No. 14/438,194 filed Apr. 23, 2015, which is a nationalization of PCT International Application PCT/US2013/063250 filed Oct. 3, 2013, which claims priority to U.S. Provisional Patent Application 61/710,289 filed Oct. 5, 2012, which applications are incorporated herein by specific reference in their entirety. This patent application also claims priority to U.S. Provisional Patent Application 62/319,159 filed Apr. 6, 2016, which provisional application is incorporated herein by specific reference in its entirety.

GOVERNMENT SUPPORT

This invention was made with government support under contract Nos. CA083831 and GM103638 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 5, 2017, is named K1262_10028US03_SL.txt and is 64,341 bytes in size.

BACKGROUND

It is often difficult to deliver biologically active compounds, such as proteins, peptides, nucleic acids, drugs, and diagnostic compounds into cells across the cell membrane because cell membranes resist the passage of these compounds. One method for transmembrane delivery of exogenous molecules is based on the mechanism of receptor-mediated endocytosis (RME). RME is a major mechanism of uptake of impermeant molecules by mammalian cells (Conner, S. D.; Schmid, S. L. Nature 2003, 422, 37-44). In this process, extracellular ligands bind cell surface receptors that cluster in dynamic regions of cellular plasma membranes. By actively pinching off to form intracellular vesicles, these membrane regions are internalized, encapsulating ligand-receptor complexes in the cytoplasm. These vesicles fuse and form early (primary/sorting) endosomes that are acidified (pH about 6) by the activation of proton pumps, conditions that generally promote the dissociation of receptors from bound ligands. Free receptors often cycle back to the cell surface, generally via subsequent trafficking through related recycling endosomes (also termed the endocytic recycling compartment) (Maxfield, F. R.; McGraw, T. E. Nat. Rev. Mol. Cell. Biol. 2004, 5, 121-132).

In contrast, free ligands are typically directed to more acidic late endosomes and lysosomes (pH 5), where hydrolases and other enzymes promote their degradation. Some viruses and other intracellular pathogens exploit RME to enter cells, but these organisms avoid degradation in lysosomes by expressing pH-dependent fusogenic proteins that disrupt endosomal membranes (Lakadamyali, M.; Rust, M. J.; Zhuang, X. Microbes Infect. 2004, 6, 929-836). To escape entrapment within these membranes and gain access to the cytosol, Semliki Forest virus disrupts early endosomes whereas influenza virus disrupts late endosomes during the course of infection. Nevertheless, many exogenous molecules that are introduced into cells using RME are not able to escape degradation in the late endosomes or the lysosome.

Accordingly, it can be important in various medical therapies to destabilize an endosome in order to allow for biologically active agents to be released from the endosome and/or lysosome into cellular cytoplasm. As such, it may be advantageous to identify substances that destabilize the endosome and/or lysosome.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 10B shows images of Ramos cells that are treated with a Cholesterylamine-SS-Fluorescein probe without the conformationally-constrained kinked peptide.

FIG. 10C shows images of Ramos cells that are treated with a Cholesterylamine-SS-Fluorescein probe with the conformationally-constrained kinked peptide.

DETAILED DESCRIPTION

Figure 1:
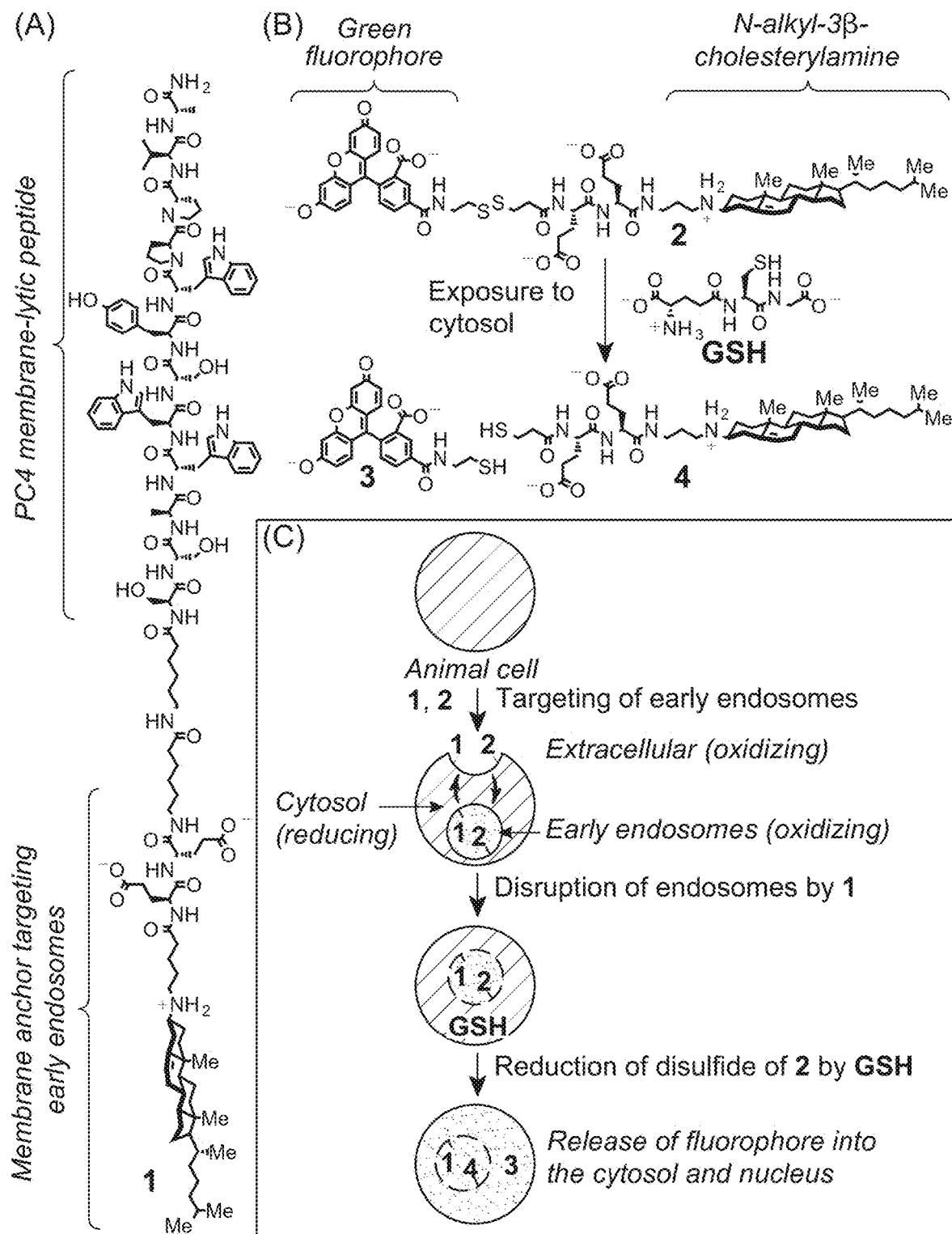
FIG. 1 shows structures of cholesterylamine-PC4 endosome disruptor (Compound 1, Panel A), a fluorescent disulfide-linked cholesterylamine (Compound 2, Panel B), and products of cleavage of Compound 2 by reduced glutathione (GSH, panel B), and Panel C shows a proposed mechanism of release of the fluorescent probe Compound 3 upon disruption of early endosomes of animal cells.

Generally, the present invention relates to conformationally-constrained and kinked peptides that have endosomal disrupting properties. As such, the present invention relates to conformationally-constrained endosomal-disrupting peptides, cargo molecules thereof, cargo delivery systems thereof, and methods of manufacture and use thereof. Standard chemical synthesis techniques and peptide chemistry can be used for manufacturing the molecules of the invention. Standard agent delivery into cells and endosomal disruption techniques to release cargo into cytoplasm in in vitro or in vivo can employ the use of the molecules of the invention. Molecules of the invention can include, without limitation, conformationally-constrained endosomal-disrupting peptides and sequences thereof, conjugates thereof, cargo molecules thereof having cargo and/or targeting moieties with or without linkers with respect to the endosomal-disrupting peptide, longer polypeptides having the peptide sequence, and any other molecular constructions with the peptide sequence.

In one example, the conformationally-constrained endosomal-disrupting peptide can be coupled to a targeting moiety, such as a cell membrane-targeting moiety like a cholesterol or cholesterol derivative directly or through a linker and/or coupling group. The targeting moiety may be any protein, peptide, nucleic acid, antibody, lipid, compound or substance that facilitates RME internalization into an endosome. in another example, the conformationally-constrained endosomal-disrupting peptide can be coupled to a cargo moiety, such as a therapeutic agent, such as siRNA, small molecule drug, macromolecule drug, polypeptide, polynucleotide, or the like. in yet another example, the conformationally-constrained endosomal-disrupting peptide is linked at one end to a cargo moiety and a targeting moiety on the other end. In another example, the conformationally-constrained endosomal-disrupting peptide is linked at one end to a targeting moiety and a cargo moiety is linked to an internal region of the compound, such as near the targeting moiety, to a linker between the targeting moiety and endosomal-disrupting peptide, or to a part of the endosomal-disrupting peptide.

The conformationally-constrained endosomal-disrupting peptide can be designed based on a viral protein that facilitates endosome release. The conformationally-constrained endosomal-disrupting peptide can be configured as a membrane-lytic peptide and may include a hydrophobic, amphipathic, or other helical or non-helical sequence kinked by a proline, glycine, or related residue. The kinked helical, non-helical, or unstructured peptide or peptidomimetic can enable the conformationally-constrained endosomal-disrupting peptide or peptidomimetic to destabilize the endosome so that cargo associated therewith can pass through pores induced in the endosome membrane. In one aspect, the conformationally-constrained endosomal-disrupting peptide is configured to mimic a viral protein that destabilizes an endosome. The conformationally-constrained endosomal-disrupting peptide can be a non-natural analogue of the dodecapeptide PC4 (sequence: SSAWWSYWPPVA; SEQ ID NO: 39). The conformationally-constrained endosomal-peptide can be linked to any targeting moiety, such as derivatives of cholesterol, other lipids, proteins, peptides, antibodies, nucleic acids, carbohydrates, or other compounds which can function as cellular and endosome-targeting elements.

In one embodiment, the conformationally-constrained endosomal-disrupting peptide can include a sequence having the SSA tripeptide of PC4 replaced with helix-inducing or otherwise conformationally-constraining 2-aminoisobutyric acid (Aib) residues or derivatives thereof in order to be an active disruptor of early endosomes. In one aspect, the peptides can include covalently linking endosome disruptive peptides to both a targeting moiety (e.g., cholesteryl carbamate or antibody or both) and a disulfide-linked cargo (e.g., a fluorophore, a toxin, or the endosome disruptive agent itself as a form of cargo), to provide delivery systems capable of release of the cargo into cellular cytosol. The conformationally-constrained endosomal-disrupting peptides disclosed here and related bioconjugates have applications as agents for cellular delivery and targeting of therapeutics and probes.

As a new strategy for delivery of cell impermeant molecules into cells, we investigated mimics of cholesterol that are designed to target membrane-active kinked peptides to early endosomes. Mimics of cholesterol were studied because free (unesterified) cholesterol is a key component of lipid bilayers of mammalian cells that resides predominantly (~60%) in the plasma membrane. Much of the remaining free cholesterol (~35%) is stored in membranes of early endosomes, particularly the endocytic recycling compartment (ERC). Constitutive cycling of cholesterol between the ERC to the plasma membrane is used to maintain homeostasis in most mammalian cells. This dynamic lipid trafficking occurs through both non-vesicular and vesicular mechanisms, and the latter process is similar to plasma membrane recycling of many cell surface receptors. We previously identified N-alkyl-3β-cholesterylamines (3β-amino-5-cholestenes) as unique synthetic mimics of cholesterol that can be avidly incorporated in the outer leaflet of plasma membranes of cells of higher eukaryotes. This incorporation occurs at least in part via a receptor-mediated process that can be inhibited by ezetimibe. Once incorporated, these compounds rapidly cycle between the plasma membrane and early/recycling endosomes, similar to many natural cell surface receptors. We found that by incorporating glutamic acid residues proximal to N-alkyl-3β-cholesterylamine and other structurally related cholesterol mimics, these compounds can preferentially localize in endosomes compared with the plasma membrane, providing a unique platform for targeting molecules to these compartments.

By linking a membrane-lytic peptide termed PC4 to N-alkyl-3β-cholesterylamine, we previously demonstrated release of a disulfide-linked fluorescent probe from endosomes into the cytoplasm and nucleus of living mammalian cells. This novel two-component delivery system employed Compound 1 (FIG. 1, panel A) having the PC4 peptide (SEQ ID NO: 39) to promote cleavage of the disulfide of cholesterylamine Compound 2 and release fluorophore Compound 3 (FIG. 1, panel B) into the cytosol and nucleus of animal cells through a proposed mechanism illustrated in FIG. 1 (Panel C). Compound 4 remains after cleavage and release of Compound 3. This mechanism is based on the observation that, like the extracellular environment, some endosomes appear to be oxidizing and disruption of these compartments can allow reduced glutathione (GSM, present at high concentrations in the cytosol, to cleave disulfides targeted to the lumen of these organelles. Alternatively, cleavage of disulfides in endosomes through other mechanisms such as the action of enzymes or other reducing agents could lead to entrapment of thiols that could be released during the course of endosome disruption. Compared to the myriad studies of cell-penetrating peptides such as HIV-1 Tat, Penetratin, Antennapedia, and many others, that nearly universally contain multiple basic amino acid residues, the delivery approach shown in FIG. 1 is unique in that basic amino acids are not required for cellular uptake or release of cargo by these agents. Moreover, because some cell-penetrating peptides with a preponderance of basic groups exhibit substantial toxicity, the avoidance of these groups may benefit certain delivery applications.

Accordingly, the compounds of the present invention can include unnatural kinked peptides as membrane-lytic agents. The compounds of the present invention can include analogues of Compound 1 that include helix-promoting or otherwise conformationally-constrained amino acids. The design of the compounds of the invention used alanine scanning and truncation approaches to optimize release of the anionic fluorescent probe Compound 3 from early endosomes. We further constructed integrated delivery systems that combine the features of the conformationally-constrained endosomal-disrupting peptide with targeting moieties and cargo molecules for delivery into the cellular cytosol.

In one embodiment, the compounds of the invention can have improved potency, maintained or increased efficacy of disruption of early endosomes, minimized toxicity in culture, and maximized solubility. We used a combination of solution-phase and solid-phase synthesis to prepare analogues of Compound 1 including lipopeptides (Compounds 5-38) and unmodified peptides (Compounds 39-54). The structures of these compounds are shown in Tables A, B, and C. Many of these analogues include Aib residues (e.g., a stretch of contiguous Aib residues), a naturally occurring amino acid found in some antibacterial peptides. The Aib residues can be derivatives thereof, reaction products thereof, or analogues thereof having peptide linkages. The Aib residues dramatically affect peptide structure, and peptides containing Aib can adopt $3_{10}$ or alpha helical structures depending on length, the number of Aib residues, and the solvent. In peptides that equilibrate between these structures, high polarity solvents tend to favor alpha helices, whereas the $3_{10}$-helix is often observed in low polarity solvents, but Aib can also provide conformational constraint in the absence of defined helical structures.

In one aspect, Compounds 1-4 and 39 are specifically excluded from the invention.

Figure 2A:
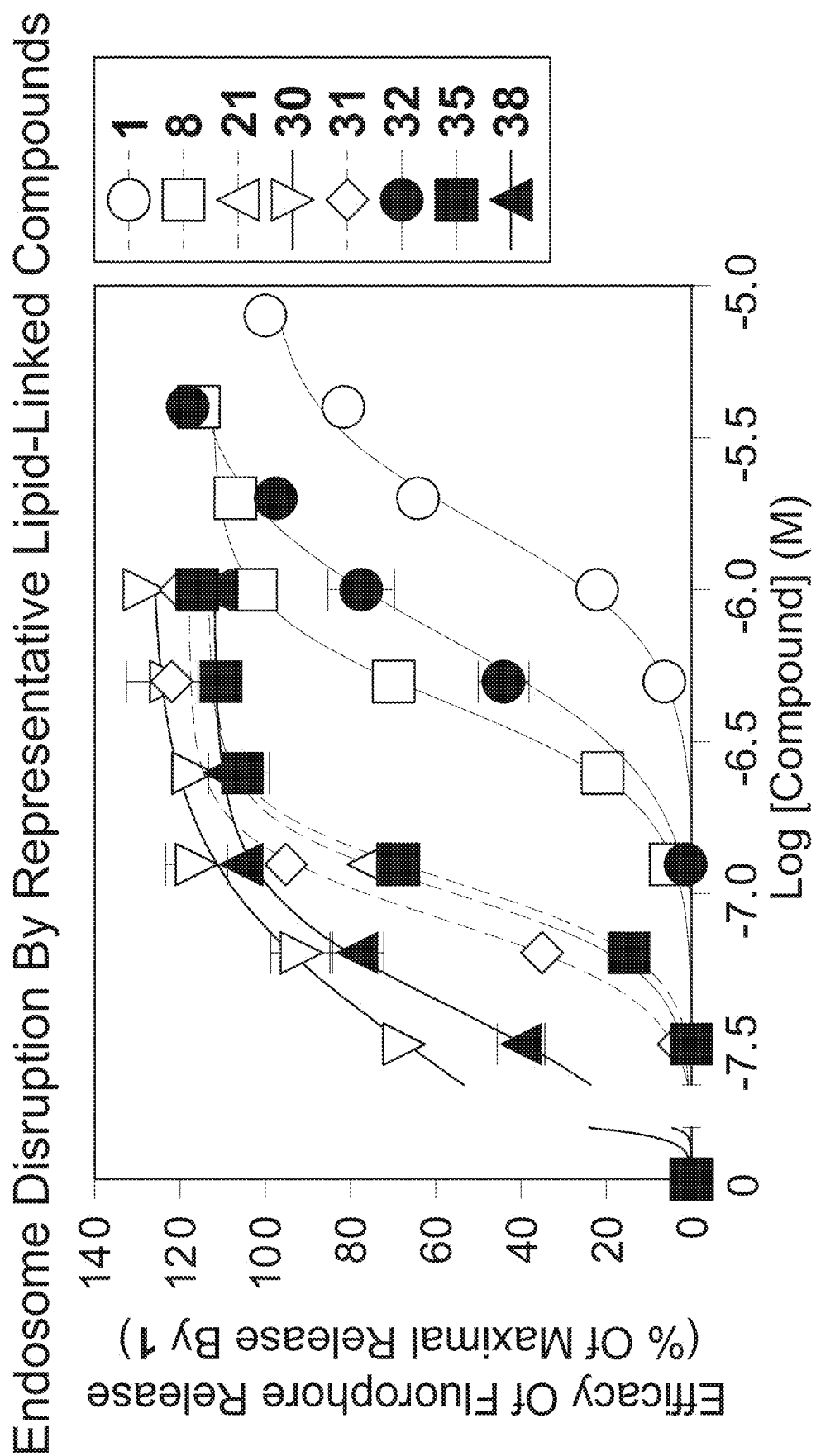
FIGS. 2A-2C include dose-response curves for disruption of endosomes of Jurkat lymphocytes by synthetic compounds of the invention.
Figure 2B:
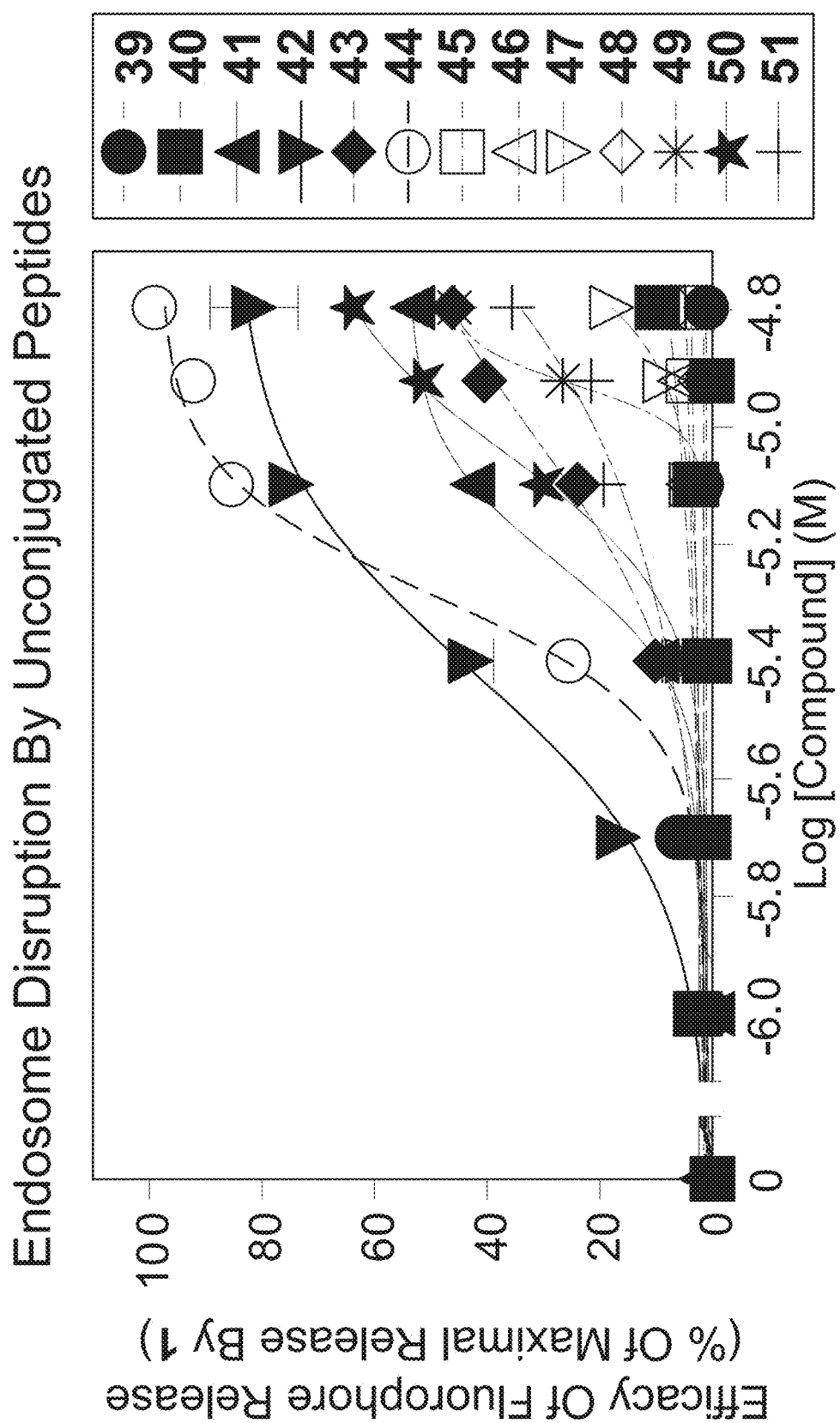
Figure 2C:
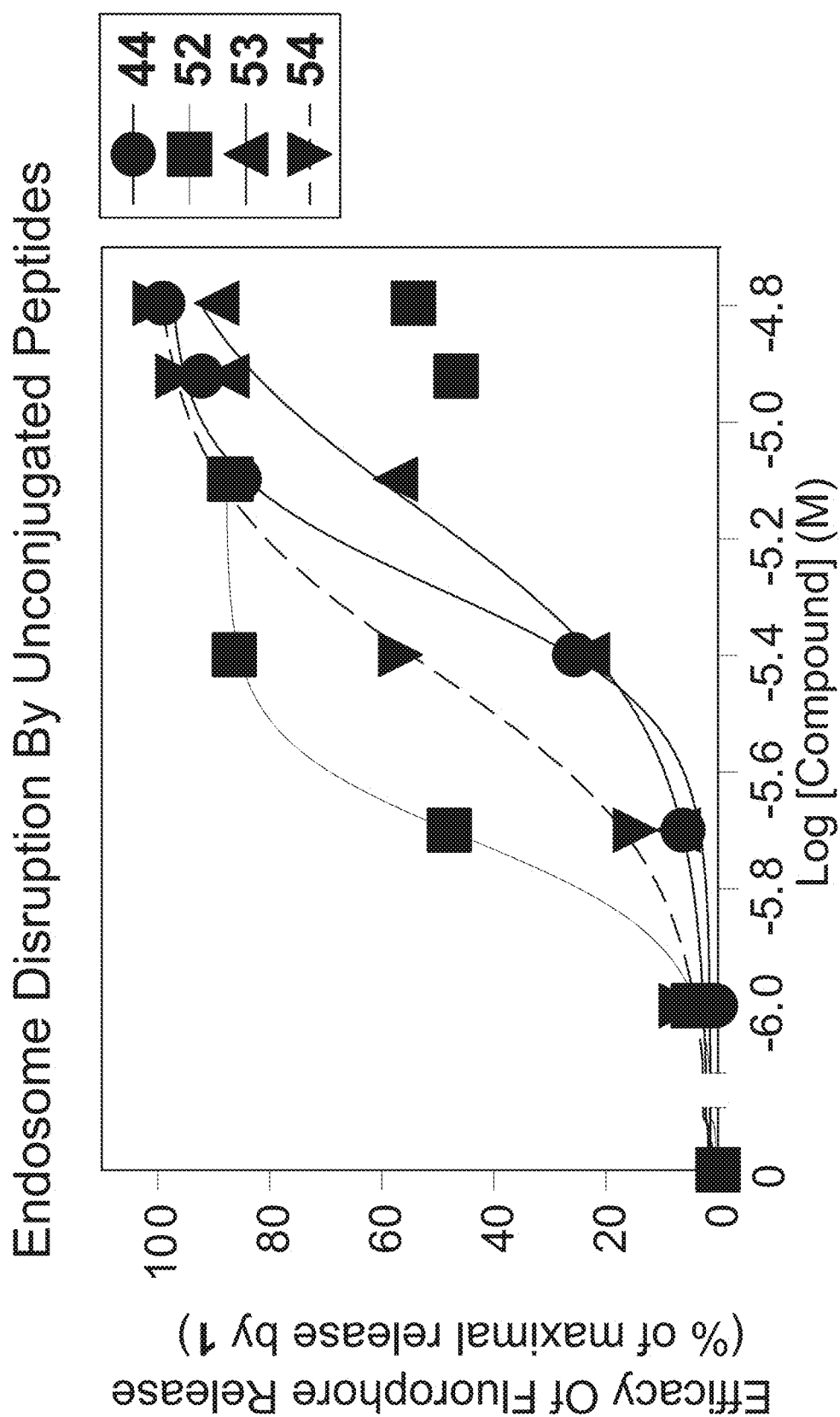

The effects of the compounds of the invention on human Juikat leukemia cells were evaluated using flow cytometry-based assays of potency, efficacy, and toxicity. Compound potency and efficacy was typically evaluated by incubating cells with endosome disruptors and fluorescent probe Compound 2 (2.5 μM) for 14 h at 37° C. Because the fluorescence of the carboxyfluorescein of Compound 2 is partially quenched by the acidity of early endosomes and this fluorophore remains trapped in the cytoplasm when released from these compartments, disruption of endosomes results in enhanced cellular fluorescence that can be readily quantified. Further confirmation of release of the fluorophore was established by confocal microscopy, which revealed green fluorescence throughout the cytoplasm and nucleus for active endosome disruptive agents. Analysis of flow cytometry data by non-linear regression was used to determine $IC_{50}$ values for potency with the efficacy expressed as a percentage. The efficacy values were defined as the percentage release of carboxyfluorescein compared to the maximal release observed by Compound 1 under the same conditions. Compound 1 typically confers maximal release in this cell line at a concentration of ~8 μM. Dose-dependent effects on cellular viability after 48 h at 37° C. in culture were also measured by flow cytometry. Thermodynamic solubility was determined in phosphate buffered saline (PBS, pH 7.4) after equilibration at room temperature for 24 hours (e.g., h or hrs). Representative dose response curves are shown in FIGS. 2A-2C, and data for representative compounds is provided in Table A and Table B and Table C.

Compounds were generated that include a targeting moiety, such as a cholesterol derivative, where the generic structures of the formulae of the compounds is provided below in Structures A, A1, A2, X, B, O, U, and Z (note Structure O is not oxygen). Structure A is a cholesterol derivative with a linker of 5-aminopentanamide or 5-aminopentanoic acid or reaction product thereof or derivative thereof between the chol and peptide R. Structure A1 is a palmitic acid derivative with a linker of 5-aminopentanamide or 5-aminopentanoic acid or reaction product thereof or derivative thereof between the chol and peptide R'. Structure A2 is a cholesteryl carbamate derivative with linker of 3-aminopropanamide or 3-aminonopropanic acid or reaction product thereof or derivative thereof between the chol and peptide R'. Structure X is a 6-aminohexanamide or 6-aminohexanoic acid or ε-Ahx amino acid or reaction product thereof or derivative thereof, which can be considered a nonstandard amino acid. B is 3-aminopropanamide or 3-aminopropanoic acid or reaction product thereof or derivative thereof, which can be considered a nonstandard amino acid. O is 3-(2-(2-(2-aminoethoxy)ethoxy)ethoxy)propanamide or 3 -(2-(2-(2-aminoethoxy)ethoxy)ethoxy)propanoic acid or mini-PEG amino acid or reaction product thereof or derivative thereof; which can be considered a nonstandard amino acid. U is 2-amino-2-methylpropanamide or 2-amino-2-methylpropanoic acid or 2-aminoisobutyric acid or Aib amino acid or reaction product thereof or derivative thereof, which can be considered a nonstandard amino acid. Z is (S)-2-aminopent-4-ynamide or (S)-2-aminopent-4-ynanoic acid or vinylglycine or reaction product thereof or derivative thereof, which can be considered a nonstandard amino acid. Structures X, B, O, U, and Z can serve as linkers in the peptide, and may be considered nonstandard amino acids for peptide descriptions and sequence listing purposes, and may include or form amide bonds common with amino acids in peptides. The structures of Structures A, A1, A2, X, B, O, U, and Z are illustrated below. The R, R', and R" of Structures A, A1, and A2 are provided in Table A.

Also, R, R', and R" can include another linker and the peptide so that the linker further separates the targeting moiety from the peptide. As such, the linker shown in Structures A, A1, and A2 can include an extended linker. Alternatively, the illustrated linker coupled to the R, R', and R" can be substituted or exchanged for a different linker. Such a linker between the targeting moiety and peptide can be any type of linker, including biodegradable and biostable linkers, and linkers which can include the cargo coupled thereto.

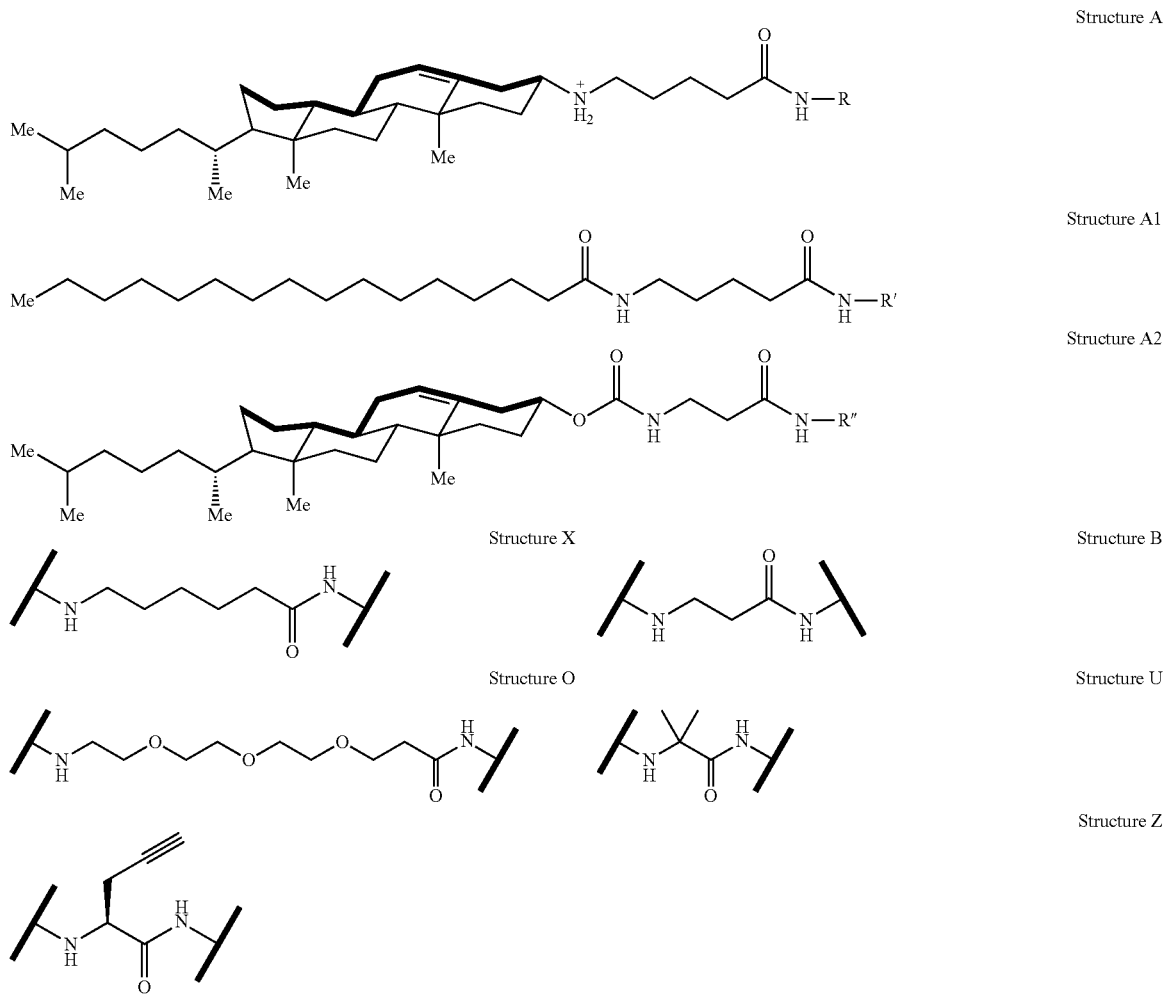

The compounds of Structures A, A1, and A2 can include peptide sequences that are lipid-linked endosome disruptors. They can include a lipidic-targeting moiety (T), a linker (L), and conformationally-constrained endosomal-disrupting peptide (CCEDP) to form T-L-EDP. The linker L can include a cargo molecule coupled thereto, as shown herein, where the cargo can be any cargo for delivery into cells or cellular membranes.

In Tables A, B, and C, the natural amino acids are represented by single letter codes, with codes for nonstandard amino acids, and X, B, O, U, and Z are defined above.

It should be recognized that the peptide sequences of Compounds 1 and 5-69 of Table A and Table B and Table C and the structures may be used alone. That is, the R, R', and R" do not have to be linked to a targeting moiety. Accordingly, the peptide sequences of Compounds 5-69 can include an amine end, such as $NH_2$ or $NH_3^+$ instead of the targeting moiety. Also, the targeting moiety of Compounds 5-38 and 55-60 can be included with a different end group or cap, such as an acetyl group (e.g., Ac). Also, the targeting moiety of Compounds 5-38 and 55-60 can be exchanged with a cargo substance. Correspondingly, the $NH_3^+$ or Ac of Compounds 39-54 and 61-68 can be exchanged for a targeting moiety or cargo substance.

The peptide sequences of Compounds 5-38 and 40-69 are novel conformationally-constrained peptides. As such, the peptide sequences of Compounds 1 and 5-69 are Peptides 1 and 5-69. The Peptides 1 and 5-69 are identified by the amino acid sequences of Sequences 1 and 5-54 and 61-69. As such, the Compounds 1 and 5-69, Peptides 1 and 5-69, and Sequences 1 and 5-54 and 61-69 correlate, and include SEQ ID NOs: 1 and 5-54 and 61-69 of the Sequence Listing. Additionally, the Compounds 79-97 include novel conformationally-constrained peptides. As such, the peptide sequences of Compounds 78-97 are Peptides 78-97. The Peptides 78-97 are SEQ ID NOs: 78-97 of the Sequence Listing.

In one embodiment, the C-terminus or N-terminus of Compounds 1 and 5-69 and Peptides 1, 5-54, 61-69, and/or 78-97 can be coupled to a targeting moiety. The targeting moiety can be any as described herein, such as a cholesterol derivative or other. However, either end of the Peptides 1, 5-54, 61-69, and/or 78-97 may be coupled to a targeting more and the other coupled to a cargo substance.

In one embodiment, the C-terminus or N-terminus of Compounds 1 and 5-69 and Peptides 1, 5-54, 61-69, and/or 78-97 and/or can be coupled to a cargo substance. The cargo substance can be any agent to be delivered into a cell. Such cargo substances can be drugs, such as small molecule drugs, nucleic acid drugs (e.g., siRNA), macromolecule drugs or protein drugs, or combinations thereof as well as any other cargo including toxins. The cargo can also be a reporter, such as a fluorophore or enzyme substrate.

In one embodiment, an internal amino acid or other linker moiety of Compounds 1 and 5-69 and Peptides 1, 5-54, 61-69, and/or 78-97 can be coupled to a cargo substance, such as shown in Compounds 55-60. The cargo substance can be any agent to be delivered into a cell. Such cargo substances can be drugs, such as small molecule drugs, nucleic acid drugs (e.g., siRNA), macromolecule drugs or protein drugs, or combinations thereof as well as any other cargo including toxins. The cargo can also be a reporter, such as a fluorophore or enzyme substrate. While a fluorophore is shown in Compounds 55-60, any cargo, such as a drug, may also be coupled in the same manner.

In one embodiment, either the C-terminus or N-terminus of the peptides can have additional peptides or polypeptides. That is, the peptide sequences shown can be internal to a polypeptide.

Figure 4A:
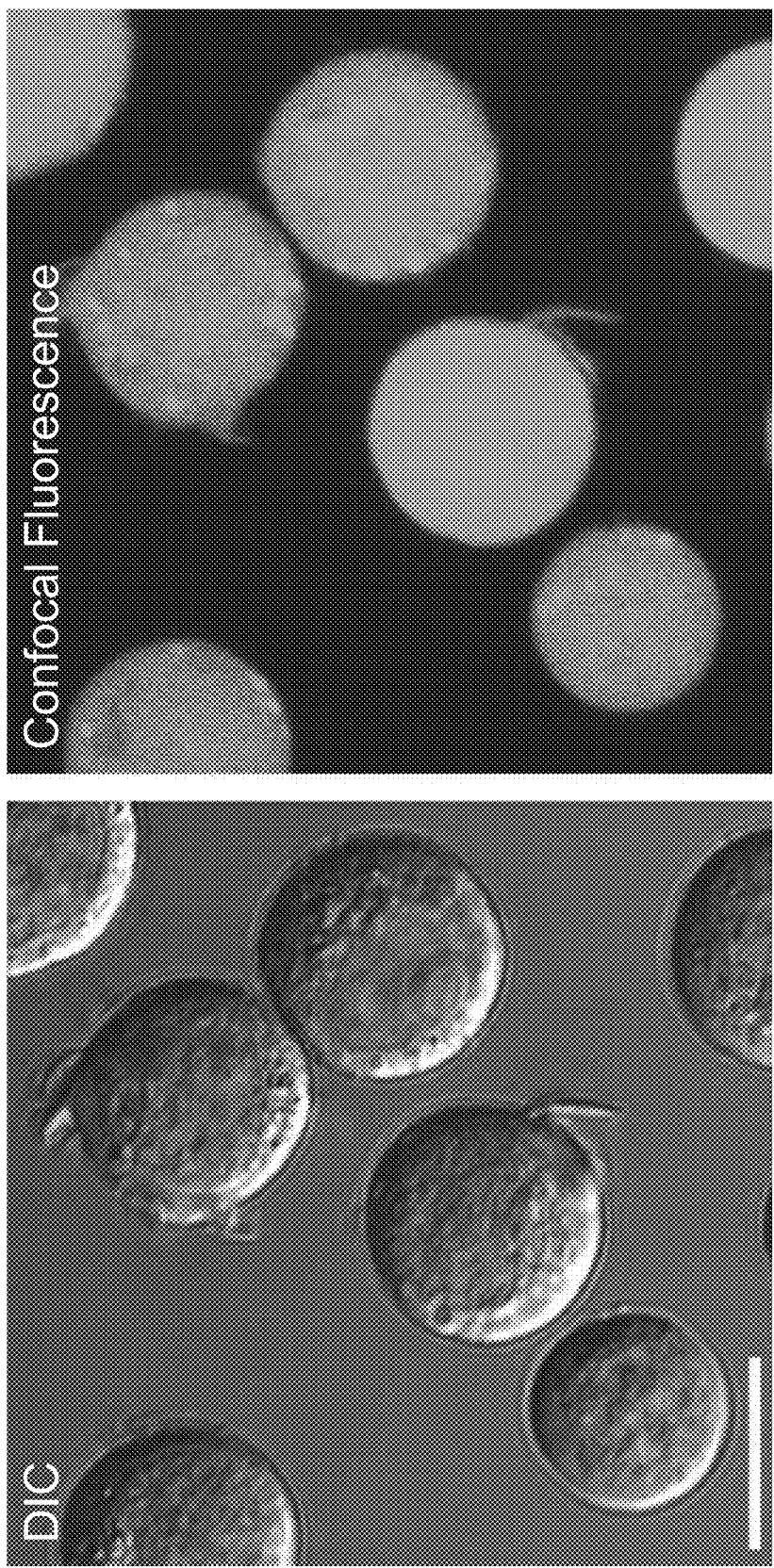
FIG. 4A includes micrographs obtained after treatment with Compound 59.
Figure 4B:
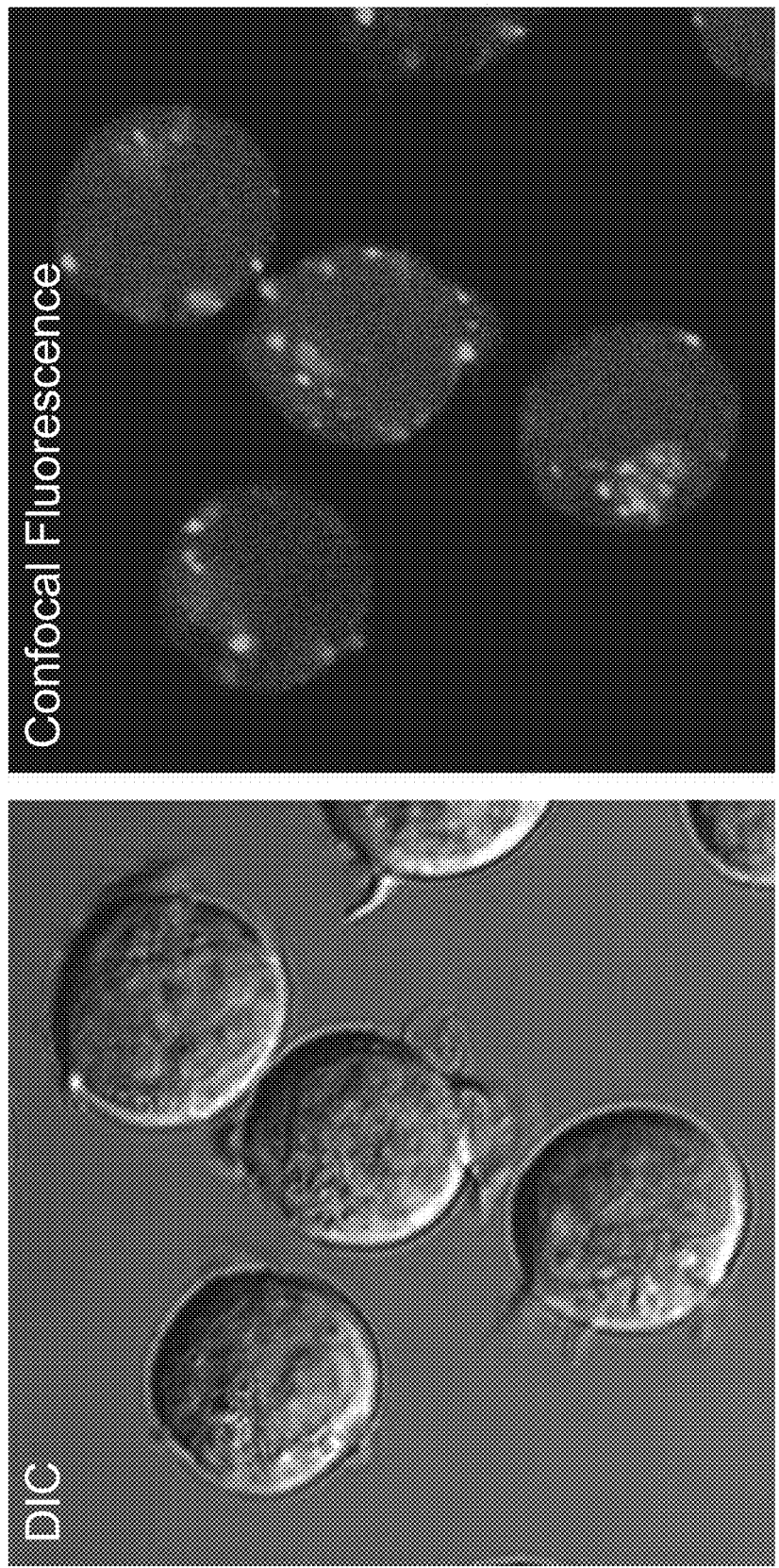
FIG. 4B includes micrographs obtained after treatment with Compound 60.

FIGS. 4A-4B show dose-response curves for disruption of endosomes of Jurkat lymphocytes by synthetic compounds. Cells were treated with fluorescent molecular probe Compound 2 (2.5 µM) and endosome disruptors for 14 hours at 37° C. Enhanced cellular fluorescence resulting from release of the pH-sensitive fluorophore Compound 3 into the cytoplasm was quantified by flow cytometry.

Figure 3:
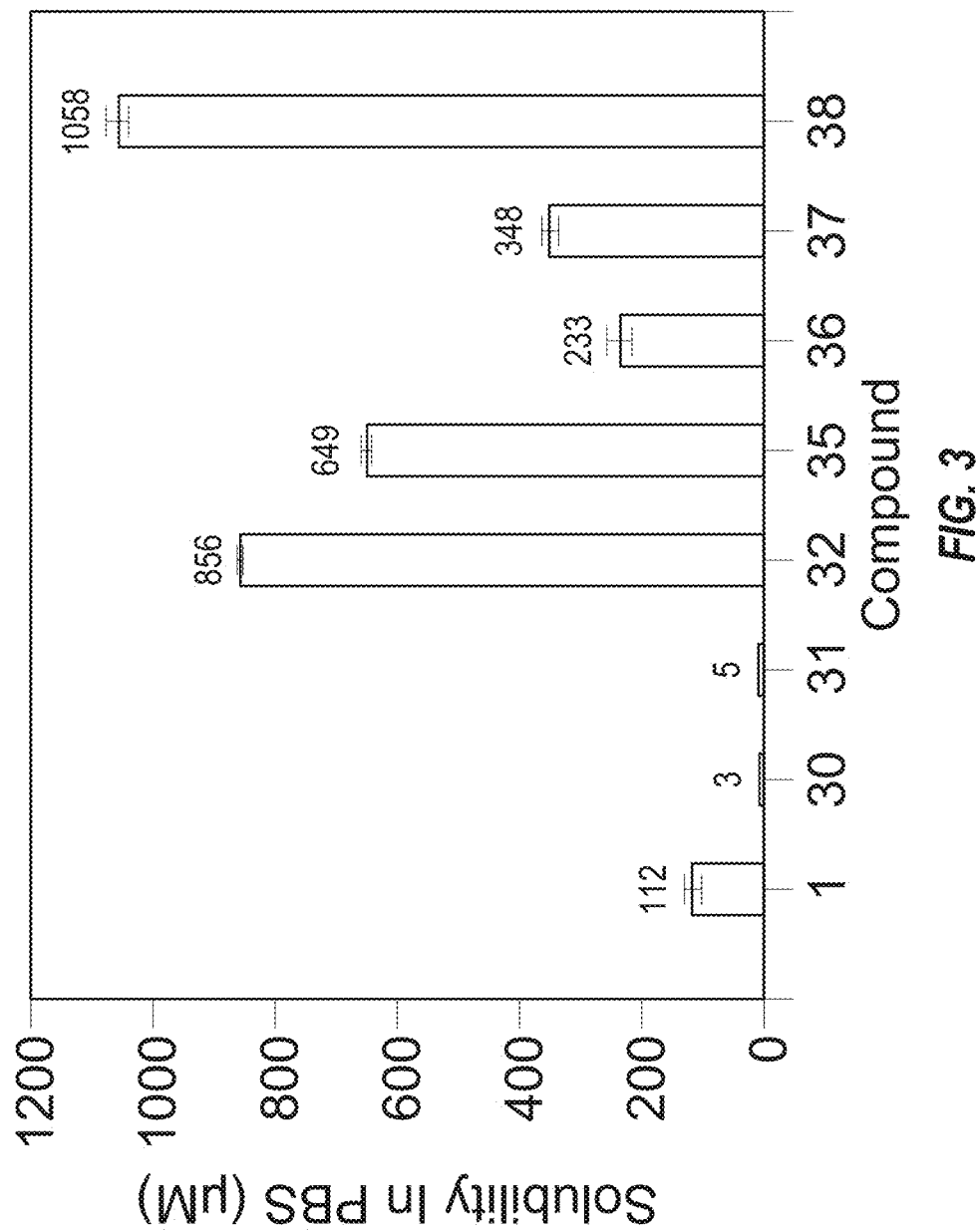
FIG. 3 includes a graph that shows solubility of compounds of the invention in PBS.

FIG. 3 shows the thermodynamic solubility values for representative compounds in PBS (pH 7.4) after equilibration for 24 hours.

Table 1 shows the potency, efficacy, toxicity, and solubility of representative synthetic endosome disruptors. The # represents the compound number in accordance with Tables A, B, and C. Concentrations of compound stock solutions were determined by absorbance measurements at 280 nm. Efficacy was determined as % change in cellular fluorescence relative to the maximal response of Compound 1, defined as 100%. Potencies and efficacies in Jurkat lymphocytes were measured by flow cytometry after treatment of cells with the compounds listed and the fluorescent probe Compound 2 (2.5 µM) for 14 hours. Toxicity to this cell line was determined by flow cytometry analysis of light scattering and counterstaining with PI after treatment for 48 h at 37° C. in culture. Thermodynamic solubility in PBS (pH 7.4, ±S.D.) was measured by sonication of 1 mL solutions containing visible solid for 30 minutes at room temperature (22° C.), gentle rocking of these samples for 24 hours at room temperature (22° C.), centrifugation for 1 hour at 16000 g, and absorbance measurements of the supernatant at 280 nm to determine concentration based on calculated extinction coefficients. Values in parentheses represent 95% confidence intervals. N.D., not determined.

TABLE A

| Compound NO. SEQ ID NO. | |
|---|---|
| 1, | R = EEXXSSAWWSYWPPVA-CONH$_2$ |
| 5, | R = EEXXAAAWWAYWPPVA-CONH$_2$ |
| 6, | R = BEEXSSAWWSYWPPVA-CONH$_2$ |
| 7, | R = BEEXAAAWWAYWPPVA-CONH$_2$ |
| 8, | R = BEEXXAAAWWAYWPPVA-CONH$_2$ |
| 9, | R = BEEXUUUWWAYWPPVA-CONH$_2$ |

TABLE A -continued

| Compound NO. SEQ ID NO. | |
|---|---|
| 10, | R = BEEXUUWWAYWPPVA-CONH$_2$ |
| 11, | R = BEEXUUUWWAYWPPV-CONH$_2$ |
| 12, | R = BEEXUUUAWAYWPPVA-CONH$_2$ |
| 13, | R = BEEXUUUWAAYWPPVA-CONH$_2$ |
| 14, | R = BEEXUUUWWAAWPPVA-CONH$_2$ |
| 15, | R = BEEXUUUWWAYAPPVA-CONH$_2$ |
| 16, | R = BEEXUUUWWAYWAPVA-CONH$_2$ |
| 17, | R = BEEXUUUWWAYWPAVA-CONH$_2$ |
| 18, | R = BEEXUUUWWAYWPPAA-CONH$_2$ |
| 19, | R = BEEXUUUWWAWWPPVA-CONH$_2$ |
| 20, | R = BEEXUUUUWWAYWPPVA-CONH$_2$ |
| 21, | R = BEEXXUUUUWWAYWPPVA-CONH$_2$ |
| 22, | R = BEEXXUUUUFFAFFPPVA-CONH$_2$ |
| 23, | R = BEEXXUUUUYYAYYPPVA-CONH$_2$ |
| 24, | R = BEEXXUUUUYYYYYPPVA-CONH$_2$ |
| 25, | R = BEEXXUUUUYYAYYPPVV-CONH$_2$ |
| 26, | R = BEEOOUUUUWWAYWPPVA-CONH$_2$ |
| 27, | R = BEEOOUUUUWWAYWPPVAA-CONH$_2$ |
| 28, | R = BEEOOUUUUYYAYYPPVV-CONH$_2$ |
| 29, | R = BEEOOUUUUYYYYYPPVV-CONH$_2$ |
| 30, | R = BEEZOOUUUUYYAYYPPVV-CONH$_2$ |
| 31, | R = BEEZOOUUUUWWAYWPPVA-CONH$_2$ |
| 32, | R' - BEEOOUUUUWWAYWPPVA-CONH$_2$ |
| 33, | R" = BZOOUUUUWWAYWPPVA-CONH$_2$ |
| 34, | R" = BEEOOUUUUWWAYWPPVA-CONH$_2$ |
| 35, | R" = BEEZOOUUUUWWAYWPPVA-CONH$_2$ |
| 36, | R" = BEEZOOUUUUWWAYWPPVV-CONH$_2$ |
| 37, | R" = BEEZOOUUUUWWAYYPPVV-CONH$_2$ |
| 38, | R" = BEEZOOUUUUYYAYYPPVV-CONH$_2$ |

TABLE B

| Compound NO. SEQ ID NO. | |
|---|---|
| 39, | Ac-SSAWWSYWPPVA-CONH$_2$ |
| 40, | Ac-AAAWWAYWPPVA-CONH$_2$ |
| 41, | Ac-UUUWWAYWPPVA-CONH$_2$ |
| 42, | Ac-UUUUWWAYWPPVA-CONH$_2$ |
| 43, | H$_3$N$^+$-UUUUWWAYWPPVA-CONH$_2$ |
| 44, | H$_3$N$^+$-UUUUWWAYWPPVV-CONH$_2$ |
| 45, | H$_3$N$^+$-UUUUAWAYWPPVV-CONH$_2$ |
| 46, | H$_3$N$^+$-UUUUWAAYWPPVV-CONH$_2$ |
| 47, | H$_3$N$^+$-UUUUWWAAWPPVV-CONH$_2$ |
| 48, | H$_3$N$^+$-UUUUWWAYAPPVV-CONH$_2$ |
| 49, | H$_3$N$^+$-UUUUWWAYWAPVV-CONH$_2$ |
| 50, | H$_3$N$^+$-UUUUWWAYWPAVV-CONH$_2$ |
| 51, | H$_3$N$^+$-UUUUWWAYWPPAV-CONH$_2$ |
| 52, | H$_3$N$^+$-UUUUYWAWWPPVV-CONH$_2$ |
| 53, | H$_3$N$^+$-UUUUWYAWWPPVV-CONH$_2$ |
| 54, | H$_3$N$^+$-UUUUWWAWYPPVV-CONH$_2$ |

TABLE C
| Compound NO. SEQ ID NO. | |
|---|---|
| 61, | Ac-UUUUUWWAYWPPVA-CONH$_2$ |
| 62, | Ac-UUUUYYAYPPVV-CONH$_2$ |
| 63, | Ac-UUUUWWAYWPPVV-CONH$_2$ |
| 64, | Ac-UUUUHHAHHPPVV-CONH$_2$ |
| 65, | Ac-UUUUWWAYWPPVL-CONH$_2$ |
| 66, | Ac-UUUUWWAYWPPLV-CONH$_2$ |
| 67, | Ac-UUUUWWAYWPPLL-CONH$_2$ |
| 68, | Ac-UUUUWWGYWPPVA-CONH$_2$ |
| 69, | Ac-UUUUYYAYPPVV-CONH$_2$ |
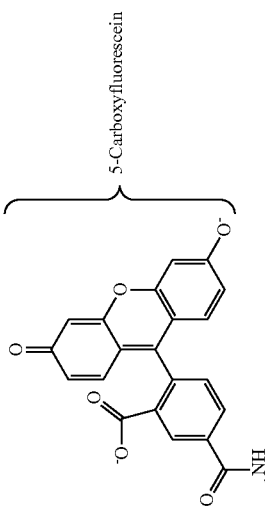

TABLE C-continued
| Compound NO. SEQ ID NO. | |
|---|---|
| UUUUYYAYYPPVV peptide | 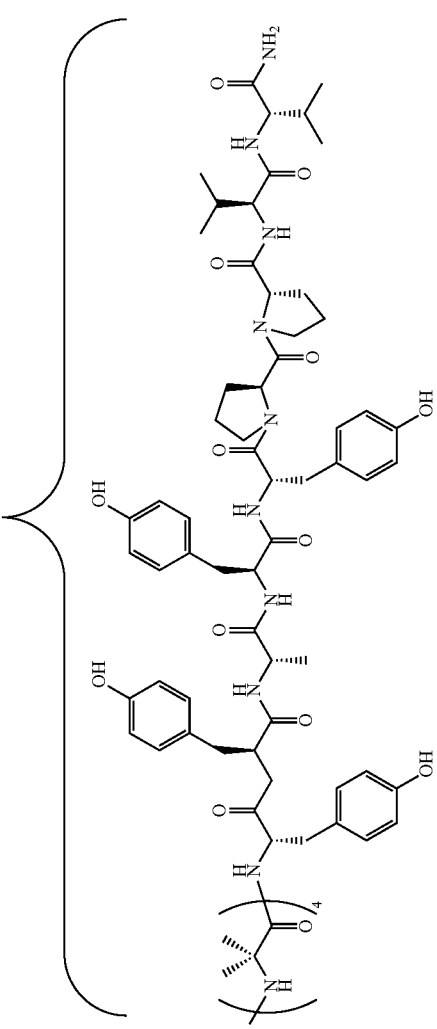<br>55 (n = 1); 56 (n = 2); 57 (n = 3); 58 (n = 4)<br>(The above compounds disclose "UUUUYYAYYPPVV" as SEQ ID NO: 69) |

TABLE C-continued
Compound NO.
SEQ ID NO.
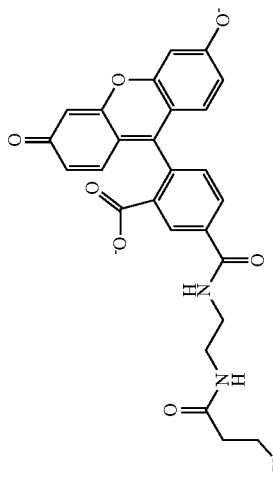
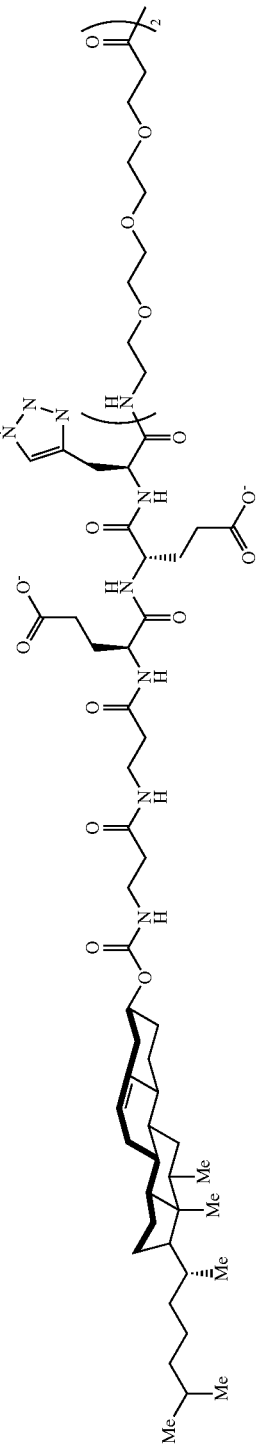
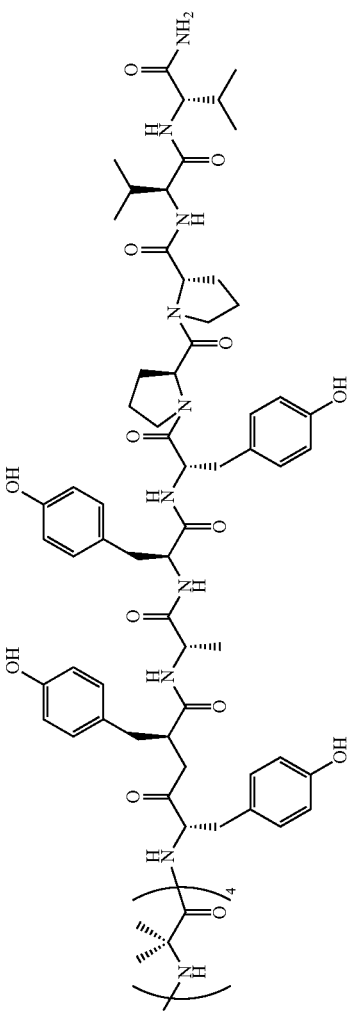
59 (X = Y = S); 60 (X = NH, Y = CO)
(The above compounds disclose "UUUUYYAYYPPVV" as SEQ ID NO: 69)

TABLE C-continued
Compound NO.
SEQ ID NO.
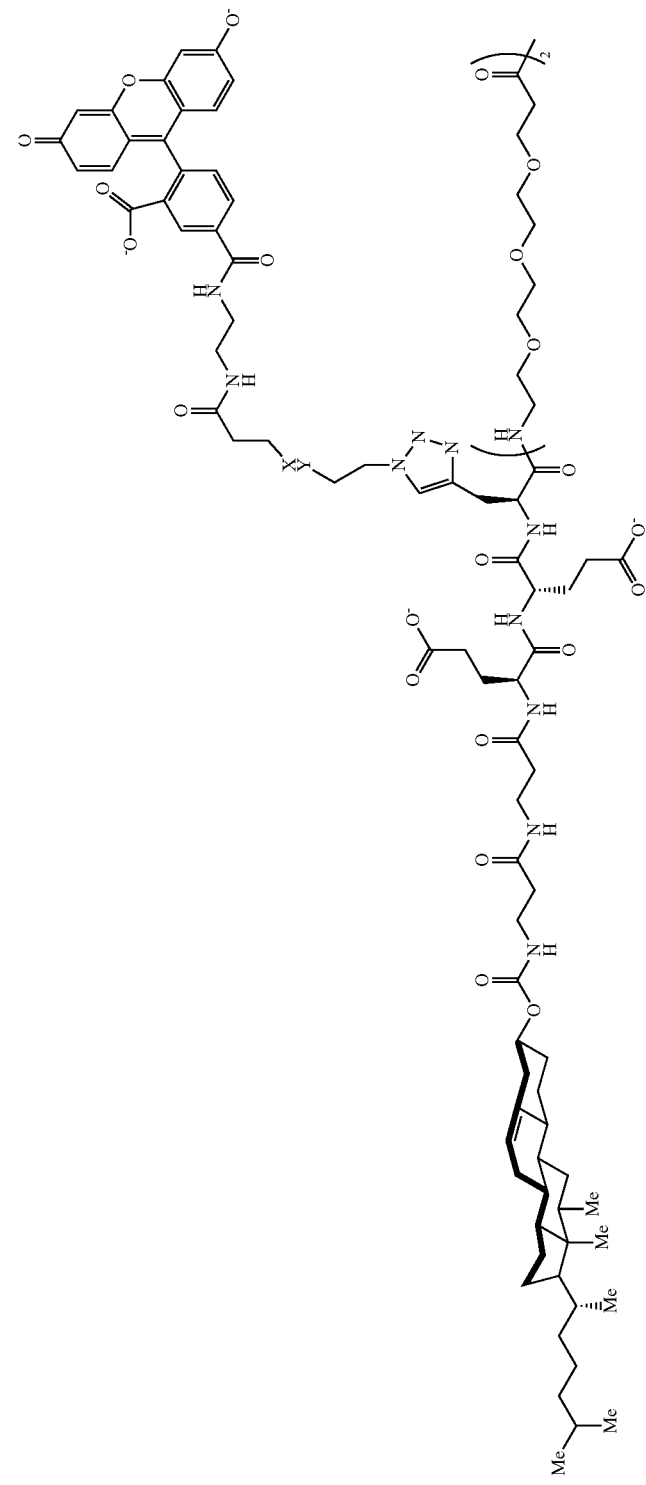

TABLE C-continued
| Compound NO. SEQ ID NO. | |
|---|---|
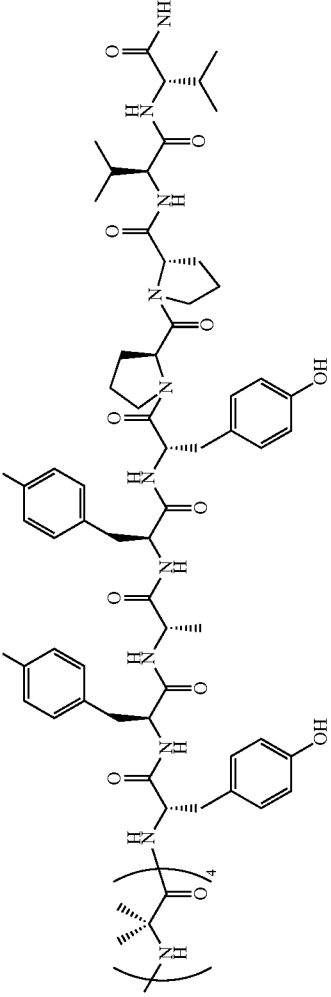
Compound 70 (X = Y = S)
Compound 71 (X = NH, Y = CO)
(Compounds 70 and 71 disclose "UUUUYYAYYPPVV" as SEQ ID NO: 69)

TABLE C-continued
| Compound NO. SEQ ID NO. | |
|---|---|
| 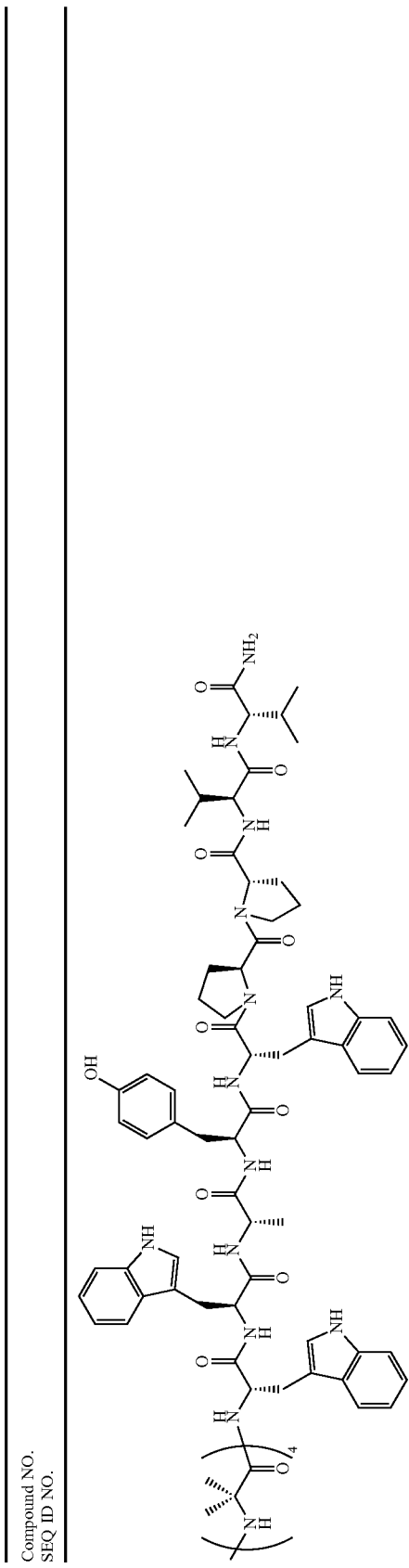<br>Compound 72<br>(Compound 72 discloses "UUUUYYAYYPPVV" as SEQ ID NO: 69)<br>(Compound 72 discloses the siRNA sequences as SEQ ID NO: 75-76, respectively, in order of appearance) | 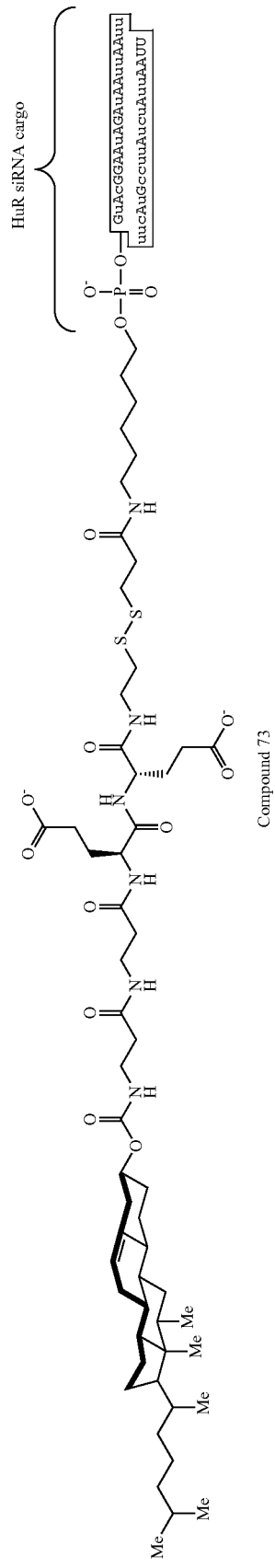<br>Compound 73<br>(Compound 73 discloses the siRNA sequences as SED ID NOS 77 and 76, respectively, in order of appearance) |

TABLE C-continued
| Compound NO. SEQ ID NO. | |
|---|---|
| | 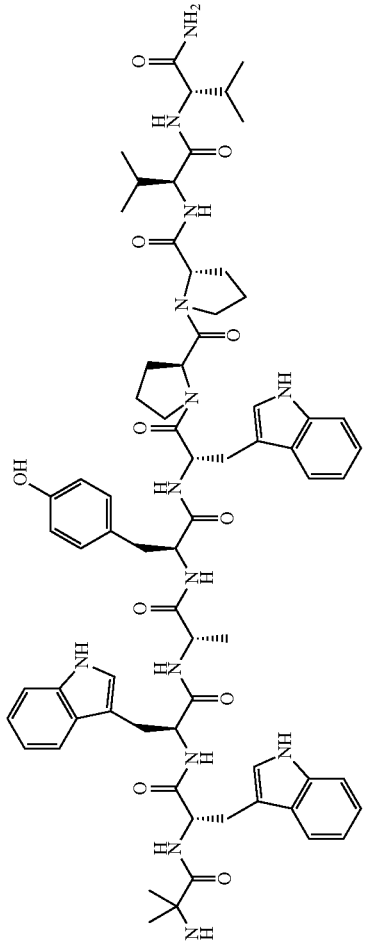
Compound 74
(Compound 74 discloses "UUUUYYAYYPPVV" as SEQ ID NO: 69) |

Compounds 55-60 and 70-72 and 73 include the peptide sequence of Compound 69—UUUUYYAYYPPVV-CONH$_2$ (SEQ ID NO: 69). Compounds 72 and 73 include the HuRsiRNA having SEQ ID NOS: 75-77. It should be noted that the targeting moiety and cargo can be exchanged for any targeting moiety and cargo. The peptide can be exchanged with other peptides in accordance with the invention.

Some of the analogues investigated (Compounds 5-31) included the N-alkyl-3-beta-cholesterylamine membrane anchor present in the endosome disruptor (Compound 1). Replacement of the SSA tripeptide of Compound 1 with a more hydrophobic and helix-promoting AAA tripeptide enhanced potency by fourfold (compare Compound 1 with Compound 5). Inclusion of a beta-alanine near the N-terminus further enhanced efficacy (compare Compound 8 with Compound 5). Substitution of the N-terminal. AAA tripeptide of Compound 7 with the conformationally-constrained UUU (U=Aib) sequence enhanced potency with some loss of efficacy that may be due to shortening of the constrained peptide (compare Compound 7 with Compound 9). Comparison of Compound 9 with Compound 10 and Compound 11 indicated that truncation of a single residue at the N-terminus or C-terminus of the core PC4-related sequence reduced potency and/or efficacy.

Analysis of the alanine-scanning analogues Compounds 12-18 compared to the reference Compound 9 revealed that many of the aromatic amino acids are helpful for high activity/potency. Additionally, the kinking PP dipeptide (e.g., di-proline sequence) provides maximal activity, but agents with a single proline residue (e.g., Compound 16 and Compound 17) retain substantial activity. These studies also revealed that the hydrophobic valine near the C-terminus is particularly helpful. Further extension of the UUU sequence by one Aib to obtain UUUU (SEQ ID NO: 2) enhanced potency by tenfold (compare Compound 19 with Compound 20).

TABLE 1

| # | Potency (EC$_{50}$, µM) | Efficacy (% of max. 1) | Toxicity (IC$_{50}$, µM) | Solubility (aq., µM) |
|---|---|---|---|---|
| 1 | 1.6 (1.4-1.9) | 100 (88-113) | 9 (8-9) | 112 ± 13 |
| 5 | 0.4 (0.4-0.5) | 100 (95-105) | 14 (13-16) | 10 ± 1 |
| 6 | 3.5 (3.3-3.6) | 94 (89-98) | N.D. | N.D. |
| 7 | 1.0 (0.9-1.1) | 99 (90-107) | 16 (15-16) | N.D. |
| 8 | 0.4 (0.4-0.5) | 113 (103-122) | 9 (8-9) | N.D. |
| 9 | 0.4 (0.3-0.5) | 87 (80-92) | 11 (10-12) | 12 ± 1 |
| 10 | 0.9 (0.8-1.0) | 97 (86-107) | 15 (15-15) | N.D. |
| 11 | 0.8 (0.8-0.9) | 71 (66-77) | 15 (15-16) | N.D. |
| 12 | 0.4 (0.3-0.5) | 99 (90-108) | 14 (13-14) | N.D. |
| 13 | 0.7 (0.6-0.8) | 97 (89-104) | 16 (15-16) | N.D. |
| 14 | 1.2 (0.8-1.9) | 51 (39-63) | N.D. | N.D. |
| 15 | N.D. | <50 | N.D. | N.D. |
| 16 | 1.6 (1.3-2.0) | 55 (47-63) | N.D. | N.D. |
| 17 | 2.1 (1.8-2.5) | 55 (47-64) | N.D. | N.D. |
| 18 | N.D. | <50 | N.D. | N.D. |
| 19 | 1.0 (0.9-1.2) | 88 (79-97) | 20 (18-21) | N.D. |
| 20 | 0.1 (0.09-0.13) | 109 (99-118) | 15 (15-15) | N.D. |
| 21 | 0.1 (0.08-0.12) | 112 (102-122) | 9 (8-9) | N.D. |
| 22 | >10 | <50 | N.D. | N.D. |
| 23 | 0.10 (0.09-0.11) | 74 (701-78) | 4 (4-4) | N.D. |
| 24 | 0.09 (0.07-0.10) | 74 (65-83) | 5 (4-5) | N.D. |
| 25 | 0.09 (0.09-0.10) | 109 (104-114) | 9 (9-9) | 22 ± 1 |
| 26 | 0.1 (0.06-0.15) | 123 (113-134) | 8 (8-9) | 14 ± 2 |
| 27 | 0.2 (0.1-0.2) | 81 (74-87) | 3 (3-3) | N.D. |
| 28 | 0.06 (0.05-0.07) | 122 (111-133) | 3 (3-4) | 63 ± 28 |
| 29 | 0.08 (0.07-0.09) | 125 (115-135) | 3 (3-3) | 90 ± 2 |
| 30 | 0.03 (0.02-0.04) | 127 (110-144) | 2 (2-2) | 3 ± 1 |
| 31 | 0.08 (0.7-0.9) | 119 (109-130) | 4 (3-4) | 5 ± 1 |
| 32 | 0.7 (0.5-1.0) | 121 (95-149) | 16 (15-17) | 856 ± 2 |
| 33 | 0.13 (0.12-0.15) | 129 (117-141) | >100 | 2 ± 1 |
| 34 | 0.10 (0.09-0.12) | 102 (92-111) | 17 (17-17) | 405 ± 20 |
| 35 | 0.11 (0.10-0.12) | 114 (110-119) | 13 (13-13) | 649 ± 11 |
| 36 | 0.06 (0.06-0.07) | 128 (122-133) | 13 (13-14) | 233 ± 21 |
| 37 | 0.04 (0.04-0.05) | 130 (124-135) | 3 (3-4) | 348 ± 13 |
| 38 | 0.04 (0.04-0.05) | 112 (102-122) | 8 (8-8) | 1058 ± 19 |
| 39 | N.D. | <<50 | N.D. | 173 ± 11 |
| 40 | N.D. | <<50 | N.D. | N.D. |
| 41 | 5.9 (5.5-6.3) | 53 (50-56) | >100 | 24 ± 3 |
| 42 | 5.3 (4.9-5.9) | 85 (78-92) | >100 | 11 ± 1 |
| 43 | 10 (6-15) | 64 (38-90) | N.D. | N.D. |
| 44 | 5.2 (4.8-5.5) | 97 (94-102) | N.D. | 22 ± 1 |
| 45 | N.D. | <<50 | N.D. | N.D. |
| 46 | N.D. | <<50 | N.D. | N.D. |
| 47 | N.D. | <<50 | N.D. | N.D. |
| 48 | N.D. | <<50 | N.D. | N.D. |
| 49 | 12 (12-12) | 45 (42-52) | N.D. | N.D. |
| 50 | 9 (8-10) | 71 (62-81) | N.D. | N.D. |
| 51 | N.D. | <50 | N.D. | N.D. |
| 52 | 1.9 (1.8-2.1) | 87 (83-93) | N.D. | N.D. |
| 53 | 7.1 (5.6-9.1) | 104 (79-128) | N.D. | N.D. |
| 54 | 3.8 (3.5-4.1) | 100 (94-107) | N.D. | N.D. |

Replacement of all of the more polar Trp and Tyr amino acids with Phe was not tolerated (compare Compound 21 with Compound 22), but potency was retained with some reduction in efficacy when the Trp residues were replaced by Tyr (compare Compound 21 with Compound 23). This loss of efficacy was overcome by installation of Val at the C-terminus (compare Compound 23 with Compound 25).

In an attempt to improve solubility, the ε-Ahx-ε-Ahx motif (e.g., XX dipeptide) of Compound 21 was replaced by a dipeptide derived from two mini-PEG amino acids (e.g., OO dipeptide). This change enhanced efficacy (compare Compound 21 with Compound 26), but the solubility of Compound 26 in PBS continued to be much lower (e.g., 14 µM) than the parent Compound 1 (e.g., 112 µM). Higher potency and solubility were achieved by further substituting the more hydrophobic Trp residues with the more polar Tyr (compare Compound 26 with Compound 28 and Compound 29), but none of these compounds were more soluble than Compound 1. The data provides enhanced potency of tyrosine-containing YYAYY peptides (SEQ ID NO: 3) over analogous tryptophan-containing WWAYW peptides (SEQ ID NO: 4), demonstrating greater affinity of tyrosine for insertion into biological membranes compared with tryptophan.

Compounds 30 and 31 included propargylglycine as an alkyne for potential coupling to cargo using Cu-catalyzed Huisgen 1,3-dipolar cycloaddition reactions with azides. These compounds represented two of the most potent and effective endosome disruptors, but showed low solubility in PBS (<5 µM). However, solubility can be enhanced by a modified linker that includes hydrophilic moieties, such as a PEG linker or a linker that includes PEG.

To evaluate the properties of endosome disruptors linked to other lipids, the palmitic acid derivative Compound 32 and cholesteryl carbamates Compounds 33-38 were synthesized. These compounds proved to be much more soluble in. PBS than the corresponding cholesterylamines (See FIGS. 2A-2C and Table 1). The palmitic acid derivative Compound 32 was sevenfold less potent than a structurally similar cholesterylamine Compound 26, but remarkably was sixty-fold more soluble in PBS (856 µM). Fortuitously, the analogous cholesteryl carbamate Compound 34 retained high potency/efficacy, comparable to Compound 26, while maintaining high solubility in PBS (405 µM). Studies of the solubility of simpler model systems that replaced the endosome disruptive peptide with a fluorophore revealed that the greater than hundredfold difference in solubility between compounds such as Compound 31 and Compound 35 does not relate to an intrinsic difference in solubility between the cholesterylamine and cholesteryl carbamate, but rather is a specific property of these particular lipopeptide derivatives (data not shown). Additionally, cholesteryl carbamate Compound 33 lacking the Glu-Glu dipeptide sequence of Compound 34 was highly active and potent but exhibited low solubility in PBS (2 µM). Based on these results, we synthesized the alkyne-containing cholesterol carbamates Compounds 35-38. All of these compounds were highly potent, active, and soluble in PBS, with Compound 37 and Compound 38 exhibiting the highest potency ($IC_{50}$=40 nM). Studies of toxicity to Jurkat lymphocytes in culture after treatment for 48 hours revealed that potent and soluble endosome disruptors such as Compound 38 can exhibit greater than hundredfold selectivity for disruption of endosomes over toxicity to cells in culture.

We further synthesized and examined the properties of much shorter peptides lacking a cellular/endosomal-targeting lipid. Whereas the unconjugated PC4 peptide (Compound 39) was devoid of biological activity in the endosome disruption assay, replacement of the N-terminal SSA motif with UUU (Compound 41) conferred substantial endosome disruption activity (FIG. 2A-2C and Table 1). This activity was improved by incorporation of additional Aib residues (Compound 42) and substitution of Ala with Val at the C-terminus (compare Compound 43 with Compound 44). The substantial activity of peptide Compound 50 bearing only a single proline residue further demonstrates that a single residue capable of inducing a kink in the structure is sufficient to enable disruption of endosomes by these types of compounds. The studies of lipid conjugates indicate that these and related peptides could be used to promote endosomal escape of cargo when conjugated to a wide variety of cellular-targeting motifs.

FIGS. 2A-2C include dose-response curves for disruption of endosomes of Jurkat lymphocytes by synthetic compounds. Cells were treated with fluorescent molecular probe Compound 2 (2.5 µM) and endosome disruptors for 14 hours at 37° C. Enhanced cellular fluorescence resulting from release of the pH-sensitive fluorophore Compound 3 into the cytoplasm was quantified by flow cytometry.

Systems that integrate a cellular/endosomal-targeting motif, endosome disruptive element, and linked cargo could also be useful for delivery applications. To create examples of these types of systems, we investigated attachment of a fluorophore as model cargo though acylation of amine-containing side chains, as well as coupling via triazoles derived from Cu-catalyzed Huisgen 1,3-dipolar cycloaddition reactions of alkynes with azides. The integrated systems of Compounds 55-60 were prepared to examine the influence of linker length and structure on delvery of carboxyfluorescein. The structures of integrated delivery systems of Compounds 55-60 include a cholesteryl carbamate linked to both an endosome disruptive peptide and carboxyfluorescein as cargo.

Figure 5:
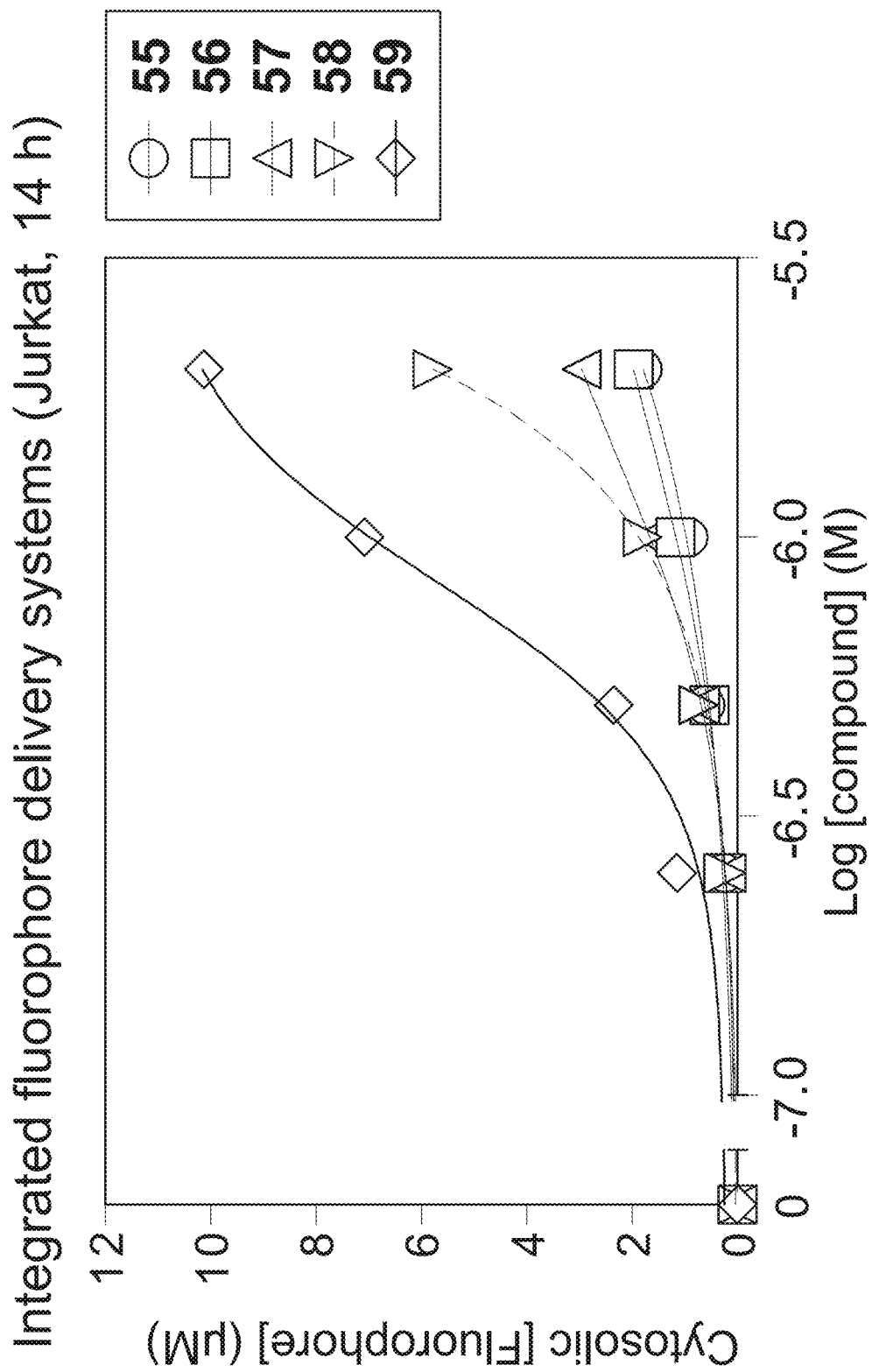
FIG. 5 includes a graph that shows endosomal release profiles of compounds of the invention.

Treatment of Jurkat lymphocytes with Compounds 55-60 resulted in dose-dependent accumulation of fluorescence in the cytosol (FIG. 5). By using bead standards (Spherotech) to convert cellular fluorescence to molecules of equivalent fluorescein (MEFL), and the diameter of Jurkat cells (12.3±0.7 µm by microscopy), the concentration of the fluorophore released into the cytosol was measured as a function of the concentration of the added delivery system. These systems were structurally specific, and small molecular changes to the linker between the cargo and peptide backbone strongly affected the efficiency of delivery. In particular, amine-containing side chains with three or fewer methylenes in the linker region (Compounds 55-57) were of relatively low potency/efficacy, but the four methylenes in the side chain of lysine provided modest potency/efficacy ($IC_{50}$~2.1 µM). In contrast, the triazole derivative Compound 59 was more than twice as potent ($IC_{50}$=830 nM). Moreover, treatment with 250 nM of Compound 59 yielded a cytosolic fluorophore concentration of over 1 µM, and at the maximum dose studied (2 µM), Compound 59 delivered 11 µM of the fluorophore into the cytosol after 14 h in culture.

FIG. 5 shows comparative efficacy of integrated fluorophore delivery systems. Dose-dependent accumulation of fluorophore Compound 3 in the cytosol of Jurkat lymphocytes after 14 h was determined by quantification of cellular fluorescence by flow cytometry, conversion to MEFL using bead standards, and calculation based on the average diameter of living Jurkat lymphocytes (12.3 µm).

Jurkat lymphocytes treated with the integrated fluorescent disulfide Compound 59 and the isosteric amide Compound 60 were imaged by confocal microscopy. As shown in FIGS. 4A-4B, only the disulfide Compound 59 released the fluorophore into the cytosol. The amide Compound 60 remained trapped in early endosomes. These results further confirm the importance of a disulfide or other cleavable linker between the delivery system and the cargo for release from endosomes by this mechanism.

FIGS. 4A-4B show confocal and DIC micrographs of living Jurkat lymphocytes treated for 16 h with the disulfide-linked fluorophore delivery system Compound 59 (Panel A) and the analogous amide control Compound 60 (Panel B). Scale bar=10 microns.

Figure 6:
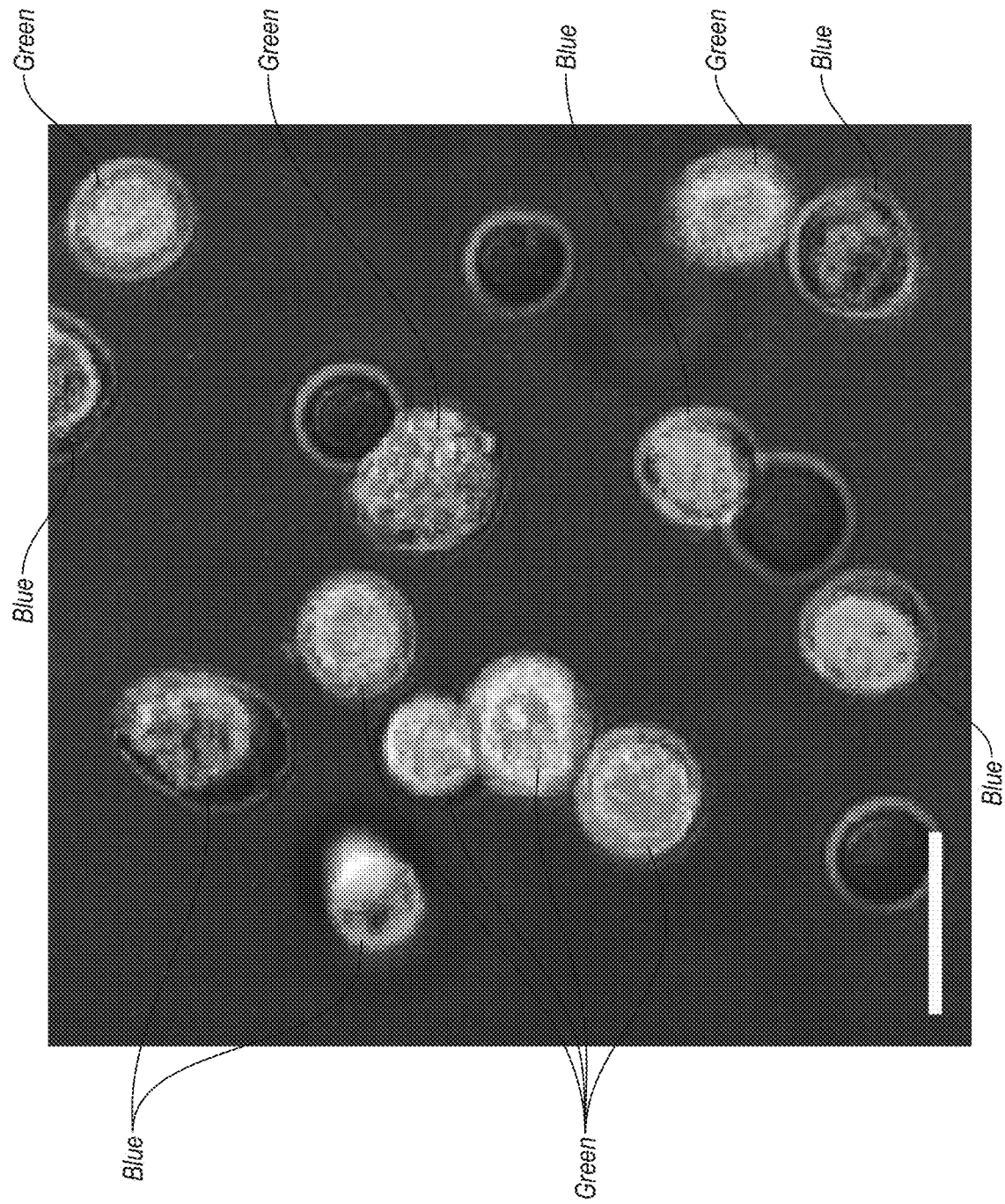
FIG. 6 includes a micrograph showing endosomal release in mouse splenocytes after IV injection of Compound 59.

To examine the potential of these types of compounds in vivo, the integrated fluorescent disulfide Compound 59 was injected into the tail vein of B6D2F1 mice at 25 mg/Kg in 100 µL of 1:1 PBS:DIVISO. After 8 hours, splenocytes were harvested and imaged by confocal microscopy. As shown in FIG. 6, green fluorescence was observed in the cytosol of living nucleated cells. These results suggest that these delivery systems have the potential for substantial half-lives and high stability in viva.

FIG. 6 shows overlaid confocal fluorescence (blue/green) and DIC micrographs of living splenocytes isolated from B6D2F1 mice. Mice were subjected to tail vein injection of the disulfide-linked fluorophore delivery system Compound 59 at 25 mg/Kg. After 8 hours, cells were harvested by splenectomy and processing with a gentle max tissue dissociator. Cells were treated with blue fluorescent cell permeable Hoechst 33342 nuclear stain and red fluorescent cell-impermeable propidium iodide nuclear stain to identify cells suitable for analysis of the subcellular distribution of the green fluorescent probe. All of the cells shown in the field were living nucleated cells or erythrocytes as evidenced by positive Hoechst staining and lack of propidium iodide staining. Erythrocytes are non-fluorescent. Scale bar=10 microns.

In one embodiment, the conformationally-constrainedendosomal-disrupting peptide can include a general structure as in Formulae 1-1C, where CC-Peptide is the peptide or peptide sequence that adds a conformational constraint to the conformationally-constrained endosomal-disrupting peptide and ED-Peptide is the peptide or peptide sequence that provides for endosomal disruption. For example, the ED-Peptide includes an amino acid that induces a kink or disruption in peptide secondary structure, and can be referred to as ED-KP. The ED-KP is an endosomal-disrupting kinked peptide, which can be a modified PC4 peptide, which is an example of a kinked peptide.

In one embodiment, the conformationally-constrained endosomal-disrupting peptide can be included in a cargo delivery molecule having a cargo moiety and/or targeting moiety with a general structure as in Formulae 2-2C.

In one embodiment, the conformationally-constrained endosomal-disrupting peptide can be included in a cargo delivery molecule having one of a cargo moiety or targeting moiety with a general structure as in Formulae 3-3C and 4-4C.

Formula 1=(CC-Peptide)$_{n1}$-(Peptide)$_{n2}$-(ED-KP)$_{n3}$-(Peptide)$_{n4}$.

Formula 1A=(CC-Peptide)$_{n1}$-(L1)$_{n2}$-(ED-KP)$_{n3}$-(L2)$_{n4}$.

Formula 1B=(CC-Peptide)$_{n1}$-(Xaa)$_{n2}$-(ED-KP)$_{n3}$-(Xaa)$_{n4}$.

Formula 1C=(CC-Peptide)$_{n1}$-(Xaa$^1$)$_{n2}$-(ED-KP)$_{n3}$-(Xaa$^2$)$_{n4}$.

Formula 2=Z$^1$—Y$^1$—X$^1$—(CC-Peptide)$_{n1}$-(Peptide)$_{n2}$-(ED-KP)$_{n3}$-(Peptide)$_{n4}$-X$^2$—Y$^2$—Z$^2$.

Formula 2A=Z$^1$—Y$^1$—X$^1$—(CC-Peptide)$_{n1}$-(L1)$_{n2}$-(ED-KP)$_{n3}$-(L2)$_{n4}$-X$^2$—Y$^2$—Z$^2$.

Formula 2B=Z$^1$—Y$^1$—X$^1$—(CC-Peptide)$_{n1}$-(Xaa)$_{n2}$-(ED-KP)$_{n3}$-(Xaa)$_{n4}$-X$^2$—Y$^2$—Z$^2$.

Formula 2C=Z$^1$—Y$^1$—X$^1$—(CC-Peptide)$_{n1}$-(Xaa$^1$)$_{n2}$-(ED-KP)$_{n3}$-(Xaa$^2$)$_{n4}$-X$^2$—Y$^2$—Z$^2$.

Formula 3=Z$^1$—Y$^1$—X$^1$—(CC-Peptide)$_{n1}$-(Peptide)$_{n2}$-(ED-KP)$_{n3}$-(Peptide)$_{n4}$.

Formula 3A=Z$^1$—Y$^1$—X$^1$—(CC-Peptide)$_{n1}$-(L1)$_{n2}$-(ED-KP)$_{n3}$-(L2)$_{n4}$.

Formula 3B=Z$^1$—Y$^1$—X$^1$—(CC-Peptide)$_{n1}$-(Xaa)$_{n2}$-(ED-KP)$_{n3}$-(Xaa)$_{n4}$.

Formula 3C=Z$^1$—Y$^1$—X$^1$—(CC-Peptide)$_{n1}$-(Xaa$^1$)$_{n2}$-(ED-KP)$_{n3}$-(Xaa$^2$)$_{n4}$.

Formula 4=(CC-Peptide)$_{n1}$-(Peptide)$_{n2}$-(ED-KP)$_{n3}$-(Peptide)$_{n4}$-X$^2$—Y$^2$—Z$^2$.

Formula 4A=(CC-Peptide)$_{n1}$-(L1)$_{n2}$-(ED-KP)$_{n3}$-(L2)$_{n4}$-X$^2$—Y$^2$—Z$^2$.

Formula 4B=(CC-Peptide)$_{n1}$-(Xaa)$_{n2}$-(ED-KP)$_{n3}$-(Xaa)$_{n4}$-X$^2$—Y$^2$—Z$^2$.

Formula 4C=(CC-Peptide)$_{n1}$-(Xaa$^1$)$_{n2}$-(ED-KP)$_{n3}$-(Xaa$^2$)$_{n4}$-X$^2$—Y$^2$—Z$^2$.

In one embodiment, the conformation-constraining peptide (i.e., CC-Peptide) is replaced with a conformation-constraining moiety (CCM) and the endosomal-disrupting peptide (i.e., ED-Peptide) is replaced with an endosomal-disrupting kinked peptide (ED-KP). In one embodiment, the conformationally-constrained endosomal-disrupting peptide can include a general structure as in Formulae 5-5C, where CCM is a chemical moiety that conformationally constrains the conformationally-constrained endosomal-disrupting peptide and KP is the kinked peptide that provides for endosomal disruption. KP can be a kinked helix or other kinked peptide structure or has at least one amino acid that destabilizes or kinks a helix, or it can be a mimic of a kinked helix, any of which that has endosomal disrupting properties. In one embodiment, the conformationally-constrained endosomal-peptide can be included in a cargo delivery molecule having a cargo moiety and targeting moiety with a general structure as in Formulae 6-6C. In one embodiment, the conformationally-constrained endosomal-disrupting peptide can be included in a cargo delivery molecule having one of a cargo moiety or targeting moiety with a general structure as in Formulae 7-7C and 8-8C.

Formula 5=(CCM)$_{n1}$-(Peptide)$_{n2}$-(ED-KP)$_{n3}$-(Peptide)$_{n4}$.

Formula 5A=(CCM)$_{n1}$-(L1)$_{n2}$-(ED-KP)$_{n3}$-(L2)$_{n4}$.

Formula 5B=(CCM)$_{n1}$-(Xaa)$_{n2}$-(ED-KP)$_{n3}$-(Xaa)$_{n4}$.

Formula 5C=(CCM)$_{n1}$-(Xaa$^1$)$_{n2}$-(ED-KP)$_{n3}$-(Xaa$^2$)$_{n4}$.

Formula 6=Z$^1$—Y$^1$—X$^1$—(CCM)$_{n1}$-(Peptide)$_{n2}$-(ED-KP)$_{n3}$-(Peptide)$_{n4}$-X$^2$—Y$^2$—Z$^2$.

Formula 6A=Z$^1$—Y$^1$—X$^1$-(CCM)$_{n1}$-(L1)$_{n2}$-(ED-KP)$_{n3}$-(L2)$_{n4}$-X$^2$—Y$^2$—Z$^2$.

Formula 6B=Z$^1$—Y$^1$—X$^1$—(CCM)$_{n1}$-(Xaa)$_{n2}$-(ED-KP)$_{n3}$-(Xaa)$_{n4}$-X$^2$—Y$^2$—Z$^2$.

Formula 6C=Z$^1$—Y$^1$—X$^1$—(CCM)$_{n1}$-(Xaa$^1$)$_{n2}$-(ED-KP)$_{n3}$-(Xaa$^2$)$_{n4}$-X$^2$—Y$^2$—Z$^2$.

Formula 7=Z$^1$—Y$^1$—X$^1$—(CCM)$_{n1}$-(Peptide)$_{n2}$-(ED-KP)$_{n3}$-(Peptide)$_{n4}$.

Formula 7A=Z$^1$—Y$^1$—X$^1$-(CCM)$_{n1}$-(L1)$_{n2}$-(ED-KP)$_{n3}$-(L2)$_{n4}$.

Formula 7B=Z$^1$—Y$^1$—X$^1$—(CCM)$_{n1}$-(Xaa)$_{n2}$-(ED-KP)$_{n3}$-(Xaa)$_{n4}$.

Formula 7C=Z$^1$—Y$^1$—X$^1$—CCM)$_{n1}$-(Xaa$^1$)$_{n2}$-(ED-KP)$_{n3}$-(Xaa$^2$)$_{n4}$.

Formula 8=(CCM)$_{n1}$-(Peptide)$_{n2}$-(ED-KP)$_{n3}$-(Peptide)$_{n4}$-X$^2$—Y$^2$—Z$^2$.

Formula 8A=(CCM)$_{n1}$-(L1)$_{n2}$-(ED-KP)$_{n3}$-(L2)$_{n4}$-X$^2$—Y$^2$—Z$^2$.

Formula 8B=(CCM)$_{n1}$-(Xaa)$_{n2}$-(ED-KP)$_{n3}$-(Xaa)$_{n4}$-X$^2$—Y$^2$—Z$^2$.

Formula 8C=(CCM)$_{n1}$-(Xaa$^1$)$_{n2}$-(ED-KP)$_{n3}$-(Xaa$^2$)$_{n4}$-X$^2$—Y$^2$—Z$^2$.

In one aspect, in any Formula, n1, n2, n3, n4, and n5 can be 0-50, such as 0, 1, 2, 3, 4, 5, 6, 7, 8, 9, 10, 15, 20, 25, 30, 35, 40, 45 or 50 or other integer value in this range.

In one aspect, Xaa, Xaa1, and Xaa$^2$ can independently be one or more natural or non-natural amino acids, essential amino acids, or non-essential amino acids, or derivatives of amino acids having L or D configuration. X$^1$ or X$^2$ are independently nothing or a coupling group or beta-alanine residues or a polypeptide. Y$^1$ or Y$^2$ are independently nothing or a linker. Z$^1$ or Z$^2$ are independently an agent or cargo for delivery into a cell or a cell-targeting moiety for targeting a cell. The cell-targeting moiety can be a receptor-targeting moiety and or a membrane-targeting moiety. Any amino acid can have L or D configuration.

In one embodiment, in the formulae shown, Z (e.g., Z$^1$ and/or Z$^2$) can be a targeting moiety, where Y (e.g., Y$^1$ or Y$^2$) or X (e.g., X$^1$ or X$^2$) includes a cargo moiety coupled thereto, such as shown in Compounds 55-60 and 70-72, and which can be represented by Formulae 2, 2A, 2B, 2C, 3, 3A, 3B, 3C, 4, 4A, 4B, 4C, 6, 6A, 6B, 6C, 7, 7A, 7B, 7C, 8, 8A, 8B, and/or 8C. The L (e.g., L1 or L2) may also include a cargo moiety coupled thereto, which can be represented by the same compounds.

In one embodiment, the cell-targeting moiety $Z^1$ and/or $Z^2$ is a cholesterol derivative selected from the group consisting of cholesterol, dihydrocholesterol, sitosterol, cholesteryl, dihydrocholesteryl, cholesterylamine, dihydrocholesterylamine, sitosterylamine, or derivative thereof. The cell-targeting moiety can be any moiety that targets and interacts with a receptor to facilitate RME. The cell-targeting moiety can be a molecule, protein, peptide, antibody, nucleic acid, carbohydrate, fragment thereof, or other.

In one embodiment, the linkers $Y^1$ or $Y^2$ are independently selected from a straight chain or branched or cyclic substituted or unsubstituted alkyl group having C1-C100 or an aromatic group, amino acid, a polypeptide, a polynucleotide, polysaccharide, a polyethylene glycol, a biodegradable linker, or combinations thereof When substituted, the substituent can be a cargo molecule.

In one embodiment, the coupling groups $X^1$ or $X^2$ independently include an amide, ether, ester, carbamate, alkyl, aryl, alkene, triazole, amine, or alkanol. Alternatively, the coupling group can be derived from a coupling reaction between the linker and a coupling agent selected from a dithio diacid, a dicarboxylic acid, an acrylic moiety, a diazide, a styrene, a vinyl carboxylic acid, a urethane, a vinyl acetate, a vinyl ether, a Diels-Alder reagent, disulfides, hydrazones, imines, acetals, orthoesters, or other acid-labile or redox sensitive groups that allow release of agents in cells or tissues, photopolymerizable moiety, photocleavable moiety, derivatives thereof, and combinations thereof.

In one embodiment, the cargo molecule agents $Z^1$ or $Z^2$ are independently selected from therapeutic agents, imaging agents, diagnostic agents, assay agents, toxic agents, or combinations thereof Examples of the agents $Z^1$ or $Z^2$ independently include a protein, peptide, polypeptide, nucleic acid, RNA, DNA, RNA/DNA hybrid, PNA, morpholinos, oligomers, siRNA, carbohydrates, lipids, markers, luminophores, tracer substances, molecular probes, oligopeptides, drugs, prodrug, toxins, a small molecule, an enzyme substrate, or combinations thereof.

In one embodiment, one of $Z^1$ or $Z^2$ is a targeting moiety and the other is cargo.

In one embodiment, the compound includes one or more beta-alanine residues in the Y (e.g., $Y^1$ or $Y^2$) linker between the X (e.g., $X^1$ or $X^2$) coupling group and the Z (e.g., $Z^1$ and/or $Z^2$) targeting moiety.

In one embodiment, the CC-Peptide is or includes one or more Aib moieties or a peptide having two or more Aib moieties that are in sequence or separate. In one embodiment, the CC-Peptide is or includes one or more alanine moieties or a peptide having one or more alanine moieties (e.g., beta-alanine) that are in sequence or separate. In one embodiment, the CC-Peptide is or includes other conformation-stabilizing or conformation-constraining amino acids or peptide sequences. In one aspect, the CC-Peptide can include one or more Aib moieties and/or one or more alanine moieties. Combinations of embodiments described above may also be used.

In one embodiment, the ED-KP is or includes one or more proline moieties or a peptide having two or more proline moieties that are in sequence or separate. In one example, the ED-KP includes two sequential proline moieties. In one aspect, the ED-KP is or includes one or more glycine moieties or a peptide having two or more glycine moieties that are in sequence or separate. in one example, the ED-KP includes two sequential glycine moieties. in one aspect, the ED-KP is or includes one or more glycine moieties and one or more proline moieties or a peptide having the glycine and proline are in sequence or separate. In one example, the ED-KP includes glycine-proline or proline-glycine moieties. In one embodiment, the ED-Peptide is or includes one or more secondary structure-altering amino acid moieties or a peptide having one or more secondary structure-altering amino acid moieties that are in sequence or separate. The ED-KP is a modified PC4 having a kink. Combinations of embodiments described above may also be used.

In one embodiment, the Peptide can be any aromatic, aliphatic, or other amino acids including non-natural aromatic, aliphatic, or other amino acids or derivatives thereof These derivatives include but are not limited to N-alkyl amino acids. In one embodiment, the Peptide includes one or more Xaa, $Xaa^1$, or $Xaa^2$. In one embodiment, the Peptide can be a linker L1 or L2, which linker L1 or L2 can be a straight chain or branched or cyclic substituted or unsubstituted alkyl group having C1-C100 or an aromatic group, amino acid, a polypeptide, a polynucleotide, polysaccharide, a polyethylene glycol, a biodegradable linker, or combinations thereof.

In one embodiment, Xaa, $Xaa^1$, or $Xaa^2$ are independently phenylalanine, tryptophan, histidine, tyrosine, thyroxine, or other aromatic amino acid.

In one embodiment, the conformationally-constraining moiety (CCM) can be a conformation-stabilizing amino acid, conformation-stabilizing peptide, conformation-stabilizing functional group, conformation-stabilizing helix mimics, or conformation-constrained amino acids or conformation-constraining peptides. The endosomal-disrupting kinked peptide (ED-KP) can be a suitable peptide sequence or mimic thereof.

In one aspect, $X^1$, $Y^1$, and $Z^1$ and $X^2$, $Y^2$, and $Z^2$ independently can each represent nothing (unmodified), one or more functional groups, one or more amino acids, a capping group, a solubilizing group such as PEG or other motif that alters solubility, a linker to a targeting motif, or a targeting motif such as a targeting motif comprising a cellular-binding or membrane-binding moiety such as a small molecule, protein, peptide, lipid, antibody, cholesterol or a cholesterol mimic, carbohydrate, nucleic acid, or other moiety with affinity for cellular components or membranes. $X^1$, $Y^1$, and $Z^1$ and $X^2$, $Y^2$, and $Z^2$ can also represent zero, one, or more cargo molecules including nucleic acids, peptides, proteins, small molecules, drugs, or probes linked to the specific structure. $X^1$, $Y^1$, and $Z^1$ and $X^2$, $Y^2$, and $Z^2$ can also be independently defined for X, Y, and Z in the incorporated references. In one aspect, the targeting moiety can be a cholesterol or cholesterol derivative.

In one aspect, the CCM can be one or more 2-aminoisobutyric acid (i.e., .Aib) moieties or a polypeptide containing one or more Aib. Also, CCM can include two or more Aib, which can be sequential Aib or an amino acid or peptide can be between the Aib moieties.

In one embodiment, each Aib moiety can be replaced by other helix-stabilizing amino acids (e.g., natural or non-natural), helix-stabilizing crosslinking groups, other helix-stabilizing modifications, or other conformationally-restricted amino acids or groups. Examples of these are found in the incorporated references or generally known to one of ordinary skill in the art. Specifically, helix-stabilizing amino acids include alanine and others as described in Richardson et al. "Amino Acid Preferences for Specific Locations at the Ends of Alpha Helices" Science 1988, 240, 1648-1652.

In one embodiment, the conformationally-constrained endosomal-disrupting peptide can include a general structure as in Formula 9, which provides a modified PC4 peptide, which is a kinked PC4 peptide derivative that is conformationally constrained in the kink. That is, the structure of Formula 9 includes the kinked peptide portion and the conformationally-constraining peptide portion. In one embodiment, the conformationally-constrained endosomal-disrupting peptide can be included in a cargo delivery molecule having a cargo moiety and targeting moiety with a general structure as in Formula 10. In one embodiment, the conformationally-constrained endosomal-disrupting peptide can be included in a cargo delivery molecule having one of a targeting moiety or a cargo as in. Formula 11 or Formula 12.

Formula 9=$(Aib)_{n1}$-$(Xaa^1)_{n2}$-$(KP)_{n3}$-$(Xaa^2)_{n4}$.

Formula 10=$Z^1$—$Y^1$—$X^1$-$(Aib)_{n1}$-$(Xaa^1)_{n2}$-$(KP)_{n3}$-$(Xaa^2)_{n4}$-$X^2$—$Y^2$—$Z^2$.

Formula 11=$Z^1$—$Y^1$—$X^1$-$(Aib)_{n1}$-$(Xaa^1)_{n2}$-$(KP)_{n3}$-$(Xaa^2)_{n4}$.

Formula 12=$(Aib)_{n1}$-$(Xaa^1)_{n2}$-$(KP)_{n3}$-$(Xaa^2)_{n4}$-$X^2$—$Y^2$—$Z^2$.

All of the variables are defined herein, with KP being a kinked peptide or an amino acid that causes a peptide to kink, such as one or more amino acids that cause an endosomal-disrupting peptide sequence to kink. As such, all or part of $(Xaa^1)_{n2}$ and/or $(Xaa^2)_{n3}$ provide for the endosomal-disrupting peptide or the endosomal-disrupting functionality. The $(KP)_{n3}$ provides the kink in the endosomal-disrupting peptide. The $(Aib)_{n1}$ provides the conformation constraint. The KP can be one or more prolines or one or more glycines or a combination of one or more prolines and one or more glycines. Examples include: proline-proline, proline-glycine, glycine-proline, and glycine-glycine, as well as tripeptides, tetrapeptides, or n-peptides thereof, where n is an integer.

In one aspect, the KP can be substituted with other secondary structure-altering moieties or amino acids. The KP can be replaced by other amino acids that alter secondary structure of peptides that may or may not be separated by one or more amino acids. In Formulae 9-9C, 10-10C, 11-11C, and 12-12C, KP1 can be the same or different from KP and $Xaa^3$ and/or $Xaa^4$ can be the same or different from $Xaa^1$ or $Xaa^2$. The n5 can be an integer that is the same or different from n3, and n6 can be an integer that is the same or different from n4. The n6 and/or n7 can independently be any integer as described for an "n" herein (e.g., is 0-50, such as 0, 1, 2, 3, 4, 5, 6, 7, 8, 9, 10, 15, 20, 25, 30, 35, 40, 45 or 50, or other value in this range.

Formula 9A=$(Aib)_{n1}$-$(Xaa^1)_{n2}$-$(KP)_{n3}$-$(Xaa^2)_{n4}$-$(KP1)_{n5}$.

Formula 10A=$Z^1$—$Y^1$—$X^1$-$(Aib)_{n1}$-$(Xaa^1)_{n2}$-$(KP)_{n3}$-$(Xaa^2)_{n4}$-$(KP1)_{n5}$-$X^2$—$Y^2$—$Z^2$.

Formula 11A=$Z^1$—$Y^1$—$X^1$-$(Aib)_{n1}$-$(Xaa^1)_{n2}$-$(KP)_{n3}$-$(Xaa^2)_{n4}$-$(KP1)_{n5}$.

Formula 12A=$(Aib)_{n1}$-$(Xaa^1)_{n2}$-$(KP)_{n3}$-$(Xaa^2)_{n4}$-$(KP1)_{n5}$-$X^2$—$Y^2$—$Z^2$.

Formula 9B=$(Aib)_{n1}$-$(Xaa^1)_{n2}$-$(KP)_{n3}$-$(Xaa^2)_{n4}$-$(KP1)_{n5}$-$(Xaa^3)_{n6}$.

Formula 10B=$Z^1$—$Y^1$—$X^1$-$(Aib)_{n1}$-$(Xaa^1)_{n2}$-$(KP)_{n3}$-$(Xaa^2)_{n4}$-$(KP1)_{n5}$-$(Xaa^3)_{n6}$-$X^2$—$Y^2$—$Z^2$.

Formula 11B=$Z^1$—$Y^1$—$X^1$-$(Aib)_{n1}$-$(Xaa^1)_{n2}$-$(KP)_{n3}$-$(Xaa^2)_{n4}$-$(KP1)_{n5}$-$(Xaa^3)_{n6}$.

Formula 12B=$(Aib)_{n1}$-$(Xaa^1)_{n2}$-$(KP)_{n3}$-$(Xaa^2)_{n4}$-$(KP1)_{n5}$-$(Xaa^3)_{n6}$-$X^2$—$Y^2$—$Z^2$.

Formula 9C=$(Xaa^4)_{n7}$-$(Aib)_{n1}$-$(Xaa^1)_{n2}$-$(KP)_{n3}$-$(Xaa^2)_{n4}$-$(KP1)_{n5}$.

Formula 10C=$Z^1$—$Y^1$—$X^1$-$(Xaa^4)_{n7}$-$(Aib)_{n1}$-$(Xaa^1)_{n2}$-$(KP)_{n3}$-$(Xaa^2)_{n4}$-$(KP1)_{n5}$-$X^2$—$Y^2$—$Z^2$.

Formula 11C=$Z^1$—$Y^1$—$X^1$-$(Xaa^4)_{n7}$-$(Aib)_{n1}$-$(Xaa^1)_{n2}$-$(KP)_{n3}$-$(Xaa^2)_{n4}$-$(KP1)_{n5}$.

Formula 12C=$(Xaa^4)_{n7}$-$(Aib)_{n1}$-$(Xaa^1)_{n2}$-$(KP)_{n3}$-$(Xaa^2)_{n4}$-$(KP1)_{n5}$-$X^2$—$Y^2$—$Z^2$.

The X, Y, and Z moieties of the formulae can represent nothing (unmodified), one or more functional groups, one or more amino acids, a capping group, a solubilizing group such as PEG or other motif that alters solubility, a linker to a targeting motif, or a targeting motif comprising a cellular-binding or membrane-binding moiety such as a small molecule, protein, peptide, antibody, lipid, cholesterol or a cholesterol mimic, carbohydrate, nucleic acid, or other moiety with affinity for cellular components or membranes. X, Y, and Z moieties of the formulae can also represent zero, one, or more cargo molecules including nucleic acids, peptides, proteins, small molecules, drugs, toxins, enzyme substrates, or probes linked to the specific structure. The Xaa can be one or more aromatic, aliphatic, or other amino acids including non-natural aromatic, aliphatic, or other amino acids or derivatives thereof. Any of the "n" or monomers (e.g., n1, n2, n3, n4, n5, n6, n7 etc.) can be n=0 to 50, 0 to 30, 0 to 20, 0 to 10, 0 to 5, or 0 to 2, or 1 to 50, 1 to 30, 1to 20, 1 to 10, 1 to 5, or 1 to 2, or 2 to 50, 2 to 30, 2 to 20, 2 to 10, 2 to 5, or 3 to 50, 3 to 30, 3 to 20, 3 to 10, 3 to 5, or 4 to 50, 4 to 30, 4 to 20, 4 to 10,4 to 5, or 4.

In one embodiment, Aib can be replaced by other helix-stabilizing amino acids (natural or non-natural), helix-stabilizing crosslinking groups, other helix-stabilizing modifications, or other conformationally-restricted amino acids or groups.

In one embodiment, the C-terminus can be modified such as by amidation or be unmodified.

In one embodiment, the linker (e.g., L or Y) can comprise amino acids or other coupling groups.

In one embodiment, the Pro in the ED-KP or KP can be replaced by other amino acids such as glycine that create a kink in a helix including two or more prolines or glycines or other amino acids or groups that alter secondary structure of peptides and that may or may not be separated by one or more amino acids. The incorporated references include examples.

In one embodiment, the Xaa is at least one amino acid that is either a natural aromatic amino acid (such as Tyr, Trp, or Phe) or a non-natural aromatic amino acid or mimic thereof.

In one embodiment, the conformationally-constrained endosomal-disrupting peptide can be included in a longer peptide sequence. Which longer peptide sequence is capable of being cleaved in a cell to form the conformationally-constrained endosomal-disrupting peptide of Formulae 1-1C, 5-5C, and 9-9C. That is, the Formulae of 1-1C, 5-5C, and 9-9C can be contained in a longer sequence that is cleaved in an endosome to form Formulae 1-1C, 5-5C, and 9-9C. The longer peptide sequence can also be included in the molecules that have targeting moieties and/or cargo. The cleaving of the longer peptide sequence can be by proteolysis. The proteolysis can be cell-specific, so that the endosome of specific cell types can be targeted for endosomal release.

In one embodiment, the targeting motif can be a lipid other than cholesterol or cholesterol derivative. In one embodiment, the targeting motif is a protein-binding small molecule (e.g., folic acid), peptide, protein, polypeptide, antibody, antibody fragment, or other protein-binding motif The targeting motif can be receptor active and bind with cell surface receptors or other cellular biomolecules that undergo endocytosis.

The cargo can be any therapeutics, probes, or other cargo to be delivered into a cell. As such, the present invention can include the use of these agents for delivery of therapeutics, probes, or other cargo into a cell. The method can use these agents for assays or diagnostic purposes by delivering assay or diagnostic cargo into a cell. In one embodiment, the cargo (e.g., Z) can be covalently linked to the conformationally-constrained kinked peptide. In one embodiment, the cargo can be non-covalently linked with the conformationally-constrained kinked peptide.

In one embodiment, the present invention includes a conformationally-constrained endosomal-disrupting peptide that is a derivative of dodecapeptide PC4. The conformationally-constrained endosomal-disrupting peptide can be longer or shorter than PC4, and can have various amino acid substitutions, additions, deletions, or other modifications from PC4 so long as the conformationally-constrained endosomal-disrupting peptide is conformationally constrained and has the kink features. The PC4 derivative can be kinked and conformationally constrained in the kinked conformation.

By exhibiting unique structural features, the compounds of this invention are structurally different from previously reported endosome-disrupting agents and are substantially more potent and more active than previously reported agents, as shown by the data. It is indeed surprising and unexpected that conformationally-constrained kinked peptides can be more active in endosomal disruption from native or more conformationally flexible peptides. Thus, the conformationally-constrained endosomal-disrupting peptides of the present invention are a significant advance in the art of endosomal disruption and cargo delivery platforms.

In the structures of Compounds 1 and 5-69, or Peptides 1, 5-54, 61-69, and/or 78-97, the peptide sequences shown can fit into any of the formulae shown herein. For example, the left side of sequences of Compounds 40-54 can be $(Aib)_{n1}$. The left side of sequences of Compounds 40-54 can be $(Xaa)_{n4}$. The PP can be the KP or KP1. The portion between the $(Aib)_{n1}$ and PP can be the $(Xaa)_{n2}$. The left side portions in sequences of Compounds 1 and 5-69 that include one or more U moieties can be the CC-Peptide and/or CCM. The right side portions to the right of any proline and/or glycine can be the right side amino acid sequence, such as Xaa, $Xaa^2$, and/or $Xaa^3$ or Peptide or L2. The portions having or being the prolines can be the ED-KP or KP or KP1. The portions between the U moieties and the prolines can be the Xaa or $Xaa^1$ or $L^1$ or Peptide.

In one embodiment, the sequences or structures of Compounds 1, 5-38, and 40-69 can include a different targeting moiety and/or the amide can be linked to a cargo. In another embodiment, the sequences or structures of Compounds 1, 5-38, and 40-69 can include the amino acid sequence shown with $X^1$, $Y^1$, and $Z^1$ at one end, and/or $X^2$, $Y^2$, and $Z^2$ at the other end.

In one embodiment, the molecule of the invention can include the Formula 13=A-Y-(Helix-Stabilizing Amino Acids, functional groups, helix mimics, or conformationally-constrained amino acids or groups)$_n$-(Xaa)$_n$-(Helix-Disrupting Amino Acids or groups or mimics)$_n$-(Xaa)$_n$-Z-B. in one embodiment, the molecule of the invention can include the Formula 14=A-Y-(Aib)$_n$-(Xaa)$_n$-(Pro or other secondary structure-altering amino acid)$_n$-(Xaa)$_n$-Z-B. Where A, B, Y, and Z can represent nothing (unmodified), one or more functional groups, one or more amino acids, a capping group, a solubilizing group such as PEG or other motif that alters solubility, a linker to a targeting motif, or a targeting motif comprising a cellular-binding or membrane-binding moiety such as a small molecule, protein, peptide, lipid, cholesterol or a cholesterol mimic, carbohydrate, nucleic acid, or other moiety with affinity for cellular components or membranes. A, B, Y, or Z can also represent zero, one, or more cargo molecules including nucleic acids, peptides, proteins, small molecules, drugs, toxins, enzyme substrates, or probes linked to the specific structure. Xaa is one or more aromatic, aliphatic, or other amino acids including non-natural aromatic, aliphatic, or other amino acids or derivatives thereof. The n is from 0 to 50, or any specific integer therebetween. The Aib can be replaced by other helix-stabilizing amino acids (natural or non-natural), helix-stabilizing crosslinking groups, other helix-stabilizing modifications, or other conformationally-restricted amino acids or groups. The C-terminus can be modified such as by amidation or unmodified. The linker can comprise amino acids or other coupling groups. The Pro can be replaced by other amino acids such as glycine, thiaproline, or analogues or derivatives of proline or glycine or other amino acids that create a kink in a helix including two or more prolines or glycines or other amino acids or groups that alter the structure of peptides by kinking a helix or inducing a turn or bend and that may or may not be separated by one or more amino acids. In one aspect, at least one amino acid of Xaa is either a natural aromatic amino acid (such as Tyr, Trp, or Phe) or a non-natural aromatic amino acid or mimic. In one aspect, the active membrane-disruptive peptide is generated by proteolysis of a longer peptide sequence.

Pharmaceutical compositions can include the compounds of the invention, and can include, without limitation, lyophilized powders or aqueous or non-aqueous sterile injectable solutions or suspensions, which may further contain antioxidants, buffers, bacteriostats, and solutes that render the compositions substantially compatible with the tissues or the blood of an intended recipient. Other components that may be present in such compositions include water, surfactants (e.g., Tween®), alcohols, polyols, glycerin, and vegetable oils, for example. Extemporaneous injection solutions and suspensions may be prepared from sterile powders, granules, tablets, or concentrated solutions or suspensions. The composition may be supplied, for example, but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The compositions described herein can be administered, for example, by parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Common carriers or excipients can be used for preparing pharmaceutical compositions designed for such routes of administration.

In one embodiment, a conformationally-constrained kinked peptide comprises: a conformationally-constraining portion and a kinked portion linked to the conformationally-constraining portion that conformationally constrains the kinked portion, the kinked portion comprising an endosomal-disrupting peptide. The peptide can include a peptide sequence of one of SEQ ID NOs: 1, 5-54, 61-69, and/or 78-97. In one aspect, the conformationally-constrained kinked portion is a majority portion of the peptide. In one aspect, the conformationally-constrained kinked portion is a minority portion of the peptide. In one aspect, the peptide can include one of Formulae 1-1C, wherein: CC-Peptide includes a peptide that conformationally constrains the ED-KP; Peptide independently includes natural, unnatural, essential or non-essential aromatic or aliphatic amino acids, or derivatives thereof having L or D configuration; ED-KP includes an endosomal-disrupting kinked peptide; Xaa, $Xaa^1$, and $Xaa^2$ are independently one or more natural or non-natural. amino acids, essential amino acids, or non-essential amino acids, or derivatives of amino acids having L or D configuration; L1 and L2 are independently linkers; and n1, n2, n3, and n4 are independently 0-50.

In one embodiment, the peptide can include one of Formulae 5-5C, wherein: CCM includes a moiety that conformationally constrains the ED-KP; Peptide independently includes natural, unnatural, essential or non-essential aromatic, aliphatic, or other amino acids, or derivatives thereof having L or D configuration; ED-KP includes an endosomal-disrupting kinked peptide; Xaa, $Xaa^1$, and $Xaa^2$ are independently one or more natural or non-natural amino acids, essential amino acids, or non-essential amino acids, or derivatives of amino acids having L or D configuration; L1 and L2 are independently linkers; and n1, n2, n3, and n4 are independently 0-50.

In one embodiment, the peptide can include one of Formulae 9-9C, wherein: KP and KP1 independently include a kinked peptide or an amino acid that causes peptide to kink; Xaa, $Xaa^1$, and $Xaa^2$ are independently one or more natural or non-natural amino acids, essential amino acids, or non-essential amino acids, or derivatives of amino acids having L or D configuration; and n1, n2, n3, n4, n5, n6, and n7 are independently 0-50.

In one embodiment, the peptide can include one of the peptide sequences of one of the SEQ ID NOs: 40-54 or 69.

In one embodiment, a cell-targeting compound can include: one or more of the peptides of one of the embodiments; and a targeting moiety linked to an end of the peptide.

In one embodiment, a cell-targeting compound can include the targeting moiety on the C-terminus or N-terminus of the peptide of one of SEQ ID NOs: 1, 5-54, 61-69, and/or 78-97.

In one embodiment, the cell-targeting compound can include one of Formulae 2-2C, 3-3C, or 4-4C, wherein: CC-Peptide includes a peptide that conformationally constrains the ED-KP; Peptide independently includes natural, unnatural, essential or non-essential aromatic or aliphatic amino acids, or derivatives thereof having L or D configuration; ED-KP includes an endosomal-disrupting kinked peptide; Xaa, $Xaa^1$, and $Xaa^2$ are independently one or more natural or non-natural amino acids, essential amino acids, or non-essential amino acids, or derivatives of amino acids having L or D configuration; L1 and L2 are independently linkers; n1, n2, n3, and n4 are independently 0-50; $Z^1$ and $Z^2$ are independently a targeting moiety, cargo moiety, or nothing, wherein at least one is a targeting moiety; $Y^1$ and $Y^2$ are independently nothing or a linker, or a linker having a cargo moiety; and $X^1$ and $X^2$ are independently nothing, a coupling group, one or more beta-alanine residues, or a polypeptide.

In one embodiment, the cell-targeting compound can include one of Formulae 6-6C, 7-7C, or 8-8C, wherein: CCM includes a moiety that conformationally constrains the ED-KP; Peptide independently includes natural, unnatural, essential or non-essential aromatic or aliphatic amino acids, or derivatives thereof having L or D configuration; ED-KP includes an endosomal-disrupting kinked peptide; Xaa, $Xaa^{1,}$ and $Xaa^2$ are independently one or more natural or non-natural amino acids, essential amino acids, or non-essential amino acids, or derivatives of amino acids having L or D configuration; L1 and L2 are independently linkers; n1, n2, n3, and n4 are independently 0-50; $Z^1$ and $Z^2$ are independently a targeting moiety, cargo moiety, or nothing, wherein at least one is a targeting moiety; $Y^1$ and $Y^2$ are independently nothing or a linker, or a linker having a cargo moiety; and $X^1$ and $X^2$ are independently nothing, a coupling group, one or more beta-alanine residues, or a polypeptide.

In one embodiment, the cell-targeting compound includes a linker between and linking the one or more peptides and the targeting moiety. In one aspect, the linker is adjacent to a cargo moiety opposite of the cholesterol carbamate, wherein the cargo moiety is branched from the linker, wherein the linker includes a bi-glutamic acid adjacent to the branch having the cargo moiety.

In one embodiment, the cell-targeting compound includes one of Formulae 10-10C, 11-11C, or 12-12C wherein: KP and KP1 independently includes a kinked peptide or an amino acid that causes peptide to kink; Xaa, $Xaa^1$, and $Xaa^2$ are independently one or more natural or non-natural amino acids, essential amino acids, or non-essential amino acids, or derivatives of amino acids having L or D configuration; $Z^1$ and $Z^2$ are independently a targeting moiety, cargo moiety, or nothing, wherein at least one is a targeting moiety; $Y^1$ and $Y^2$ are independently nothing or a linker, or a linker having a cargo moiety; $X^1$ and $X^2$ are independently nothing, a coupling group, one or more beta-alanine residues, or a polypeptide; and n1, n2, n3, n4, n5, n6, and n7 are independently 0-50.

In one embodiment, the cell-targeting compound includes a structure of one of Compounds 1, 5-38, and 40-73.

In one embodiment, a cargo delivery compound includes: one of the peptides described herein; and a cargo moiety linked to the peptide.

In one embodiment, a cargo delivery molecule can include cargo that is a therapeutic agent, pharmaceutical, nutraceutical, diagnostic agent, assay agent, tracking agent, suicide agent, toxin, or any other agent.

In one embodiment, a molecule can include one or more beta-alanine residues between the peptide and the targeting moiety.

In one embodiment, a molecule can include the conformationally-constraining portion having one or more Aib moieties or a peptide having two or more Aib moieties that are in sequence or separate. In one aspect, the conformationally-constraining portion includes one or more alanine moieties or a peptide having one or more alanine moieties that are in sequence or separate. In one aspect, the kinked portion is or includes one or more proline moieties or a peptide having two or more proline moieties that are in sequence or separate. In one aspect, the kinked portion includes two sequential proline moieties. In one aspect, the kinked portion includes one or more glycine moieties or a peptide having two or more glycine moieties that are in sequence or separate. In one aspect, the kinked portion includes two sequential glycine moieties. In one aspect, the kinked portion includes one or more glycine moieties and one or more proline moieties or a peptide where the glycine and proline are in sequence or separate. In one aspect, the kinked portion includes one or more glycine-proline segments or one or more proline-glycine segments. In one aspect, Xaa, $Xaa^1$, or $Xaa^2$ are independently phenylalanine, tryptophan, histidine, tyrosine, thyroxine, or other aromatic amino acids.

In one embodiment, $X^1$, $Y^1$, and $Z^1$ and $X^2$, $Y^2$, and $Z^2$ independently can each represent nothing (unmodified), one or more functional groups, one or more amino acids, a capping group, a solubilizing group such as PEG or other motif that alters solubility, a linker to a targeting motif, or a targeting motif such as a targeting motif comprising a cellular-binding or membrane-binding moiety such as a small molecule, protein, peptide, lipid, cholesterol or a cholesterol mimic, carbohydrate, nucleic acid, or other moiety with affinity for cellular components or membranes. In one aspect, $X^1$, $Y^1$, and $Z^1$ and $X^2$, $Y^2$, and $Z^2$ represent zero, one, or more cargo molecules including nucleic acids, peptides, proteins, small molecules, drugs, or probes.

In one embodiment, the CCM can be one or more 2-aminoisobutyric acid (i.e., Aib) moieties or a polypeptide containing one or more Aib. In one aspect, CCM can include two or more Aib, which can be sequential Aib or an amino acid or peptide can be between the Aib moieties. In one aspect, each Aib moiety can be replaced by other helix-stabilizing amino acids (e.g., natural or non-natural), helix-stabilizing crosslinking groups, other helix-stabilizing modifications, or other conformationally-restricted amino acids or groups.

In one aspect, the coupling agent, such as $X^1$ and/or $X^2$ can be selected from a dithio diacid, a dicarboxylic acid, an acrylic moiety, a diazide, a styrene, a vinyl carboxylic acid, a urethane, a vinyl acetate, a vinyl ether, a Diels-Alder reagent, disulfides, hydrazones, imines, acetals, orthoesters, or other acid-labile or redox sensitive groups that allow release of agents in cells or tissues, photopolymerizable moiety, photocleavable moiety, derivatives thereof, and combinations thereof.

In one aspect, the invention includes a method of disrupting endosomes comprising: providing the molecule of the invention having an endosomal-disrupting peptide; and administering the molecule to a cell. In one aspect, the cell is in a cell culture. In one aspect, the cell is in a living organism. In one aspect, the method can include administering a sufficient amount of the molecule to disrupt the endosome of the cell.

In one embodiment, a method of delivering cargo to a cell can include: performing the method of disrupting endosomes of one of the embodiments with the molecule having a cargo moiety; and allowing the molecule and/or cargo to escape the endosome into cytoplasm of the cell.

In one embodiment, a method of targeting a cell for delivery of cargo can include: performing the method of disrupting endosomes with a molecule having a targeting moiety; and allowing the molecule to target and associate with a cell membrane sufficiently for endocytosis of the molecule.

In one embodiment, a cell-targeting compound can include: one or more peptides having a conformationally-constraining portion, and a kinked portion linked through a peptide linker to the conformationally-constraining portion that conformationally constrains the kinked portion, the kinked portion comprising an endosomal-disrupting kinked peptide derived from SEQ ID NO: 39; and at least one targeting moiety linked to a middle region or an end of the peptide, wherein such linking is optionally through an extension linker, and where in the at least one targeting moiety can include a specific targeting moiety that targets a receptor or ligand on a cell surface and can include a general targeting moiety that can generally target cell surfaces (e.g., hydrophobic targeting moiety that targets cell membranes), wherein: the kinked portion has an amino acid sequence that includes one or more amino acids independently selected from proline and glycine; the conformationally-constrained portion includes one or more 2-aminoisobutyric acid residues or derivatives thereof (e.g., derivatives having alkyl moieties replaced by longer chain alkyl moieties such as C2-C12 or cycloalkane, or other cyclic moiety replacing one or both methyl groups); and the peptide linker includes one or more natural or non-natural amino acids, essential amino acids, or non-essential amino acids, or derivatives of amino acids having an L or D configuration or peptide thereof, wherein the extension linker extends the at least one targeting moiety from the conformationally-constraining portion. The extension linker can be PEG or other hydroscopic or water solubilizing moiety. An optional targeting linker can be used to link one or two or more targeting moieties to the conformationally-constraining portion with or without the extension linker.

Figure 7:
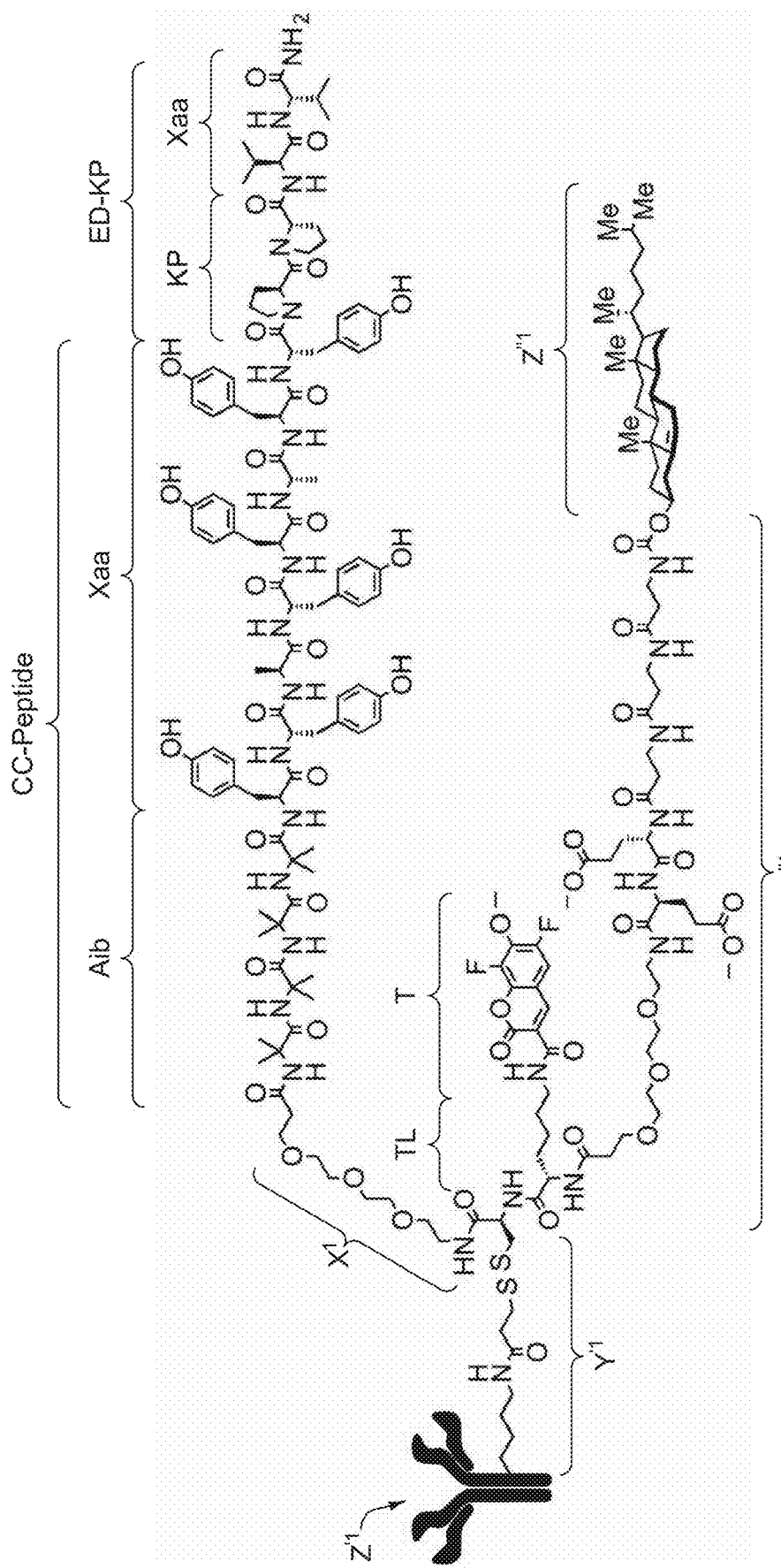
FIG. 7 includes a structure of a compound with a conformationally-constrained kinked peptide with a specific targeting moiety and general targeting moiety linked to the conformationally-constrained kinked peptide through a branched linker.

Examples of such a cell-targeting compound are provided in FIG. 7, where the variables defined here are illustrated. It should be noted that Z'1 is an antibody, but can be any other specific targeting moiety that targets a specific receptor on a cell. The Z"1 can be a non-specific targeting moiety, such as a lipid or cholesterol, that can generally associate with a cell membrane. The T can be a tracking moiety, such as Pacific Blue, which can be linked to the rest of the molecule through a linker (TL), such as a glycine, beta-alanine, or GABA, or other linker such as those described herein. The compound is divided into sections that are defined in accordance with the formulae provided herein.

Figure 8:
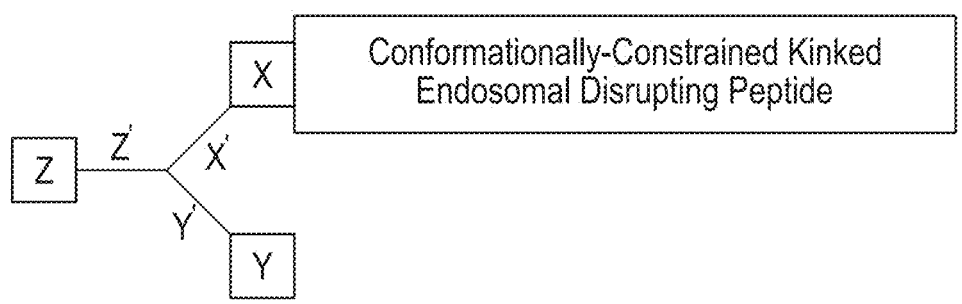
FIGS. 8, 8A, 8B, 8C, and 8D show examples of embodiments of a conformationally-constrained kinked peptide linked to targeting moieties or cargo moieties through branched likers.

In one embodiment, FIG. 8 shows the ZYX- or —XYZ portion of the cell-targeting compound. The figures shown here illustrate the design and function of targeted endosome disruptive compounds and conjugates. As such, FIG. 8 shows a general design of targeted endosome disruptors that are shown to include two or more of a targeting moiety, an endosome disruptor, a lipid, a cholesterol derivative, a ligand, a small molecule, a solubilizing moiety, a cargo moiety, a therapeutic agent, a toxic agent, an imaging agent, a diagnostic agent, a prodrug, a drug, a linker, an amino acid, a peptide, a protein, a natural or non-natural nucleic acid, a natural or non-natural carbohydrate, a molecular probe, a cleavable group, any other moiety, combinations thereof, or nothing, wherein at least one is a targeting moiety and one is an endosome disruptor. X can be independently nothing, a coupling group, one or more beta-alanine residues, or a polypeptide as described herein for X1 or X2. X' can be independently nothing, a coupling group, one or more beta-alanine residues, or a polypeptide as described herein for X1 or X2. Z can be a targeting moiety such as a specific targeting moiety, or as described from Z1 or Z2 herein. Z' can be a linker, such as from a branch that links the targeting moiety Z to the compound. Y can be nothing or a linker, or a linker having a cargo moiety or a linker having a general targeting moiety (e.g., hydrophobic moiety, such as cholesterol or alkyl chain or lipid) or a general targeting moiety. Y' can be a linker, such as from a branch that links the general targeting moiety Y to the compound. In FIG. 8, Y can be a general targeting moiety; however, Z is often used to be a specific targeting moiety or general targeting moiety given that at least one Z is a specific targeting moiety, although all Zs may be general targeting moieties. Thus, in FIG. 8, Y can be replaced with —Y—Z or —Y—Z$^1$ or —Y—Z$^2$, where Z, Z$^1$, or Z$^2$ is a targeting moiety such as a general targeting moiety. In one aspect, Z', Y' and X' are independently a linker, a linker having one or more cargo moieties, a linker having one or more targeting moieties, a linker having one or more specific targeting moieties, a linker having one or more general targeting moieties (e.g., hydrophobic moiety), a linker having one or more reporter moieties (Tracking moiety—T), a linker having one or more solubilizing moieties (e.g., PEG), a linker having one or more natural or non-natural amino acids, a linker having one or more cleavable moieties, a linker having a disulfide, a linker having one or more lipids, a linker having any other moiety, combinations thereof, or nothing. In FIG. 8, Z, Z', X, X', and/or Y, Y' can be interchangeable and/or repeated with any of Z, Z', X, X', and/or Y, Y'.

Figure 8A:
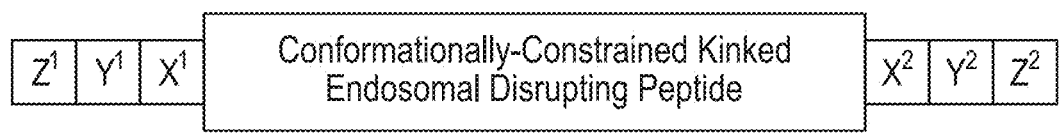
Figure 8B:
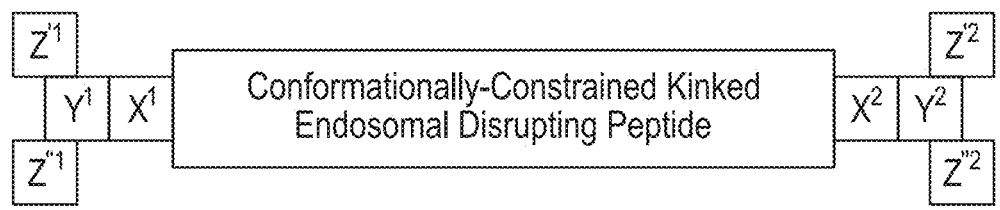
Figure 8C:
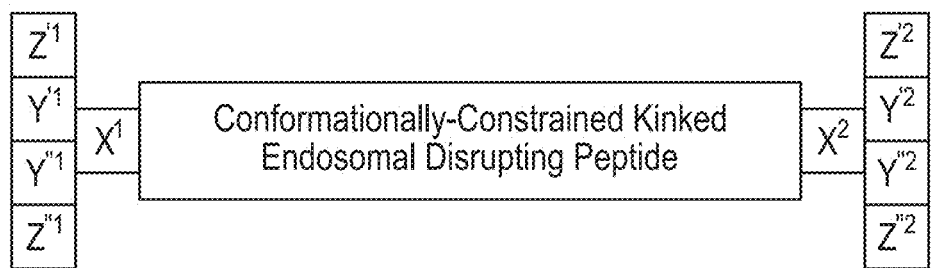
Figure 8D:
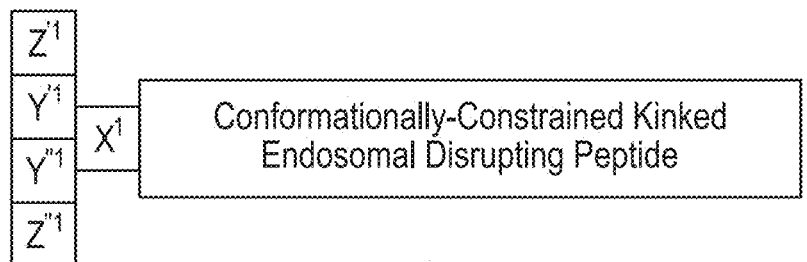

FIGS. 8A-8D show examples that correspond with Formulae 10-10C, 11-11C, or 12-12C, where the definitions provided here for the variables apply to the examples. In FIG. 8A, Z$^1$ and Z$^2$ are independently a targeting moiety, cargo moiety, or nothing, wherein at least one is a targeting moiety; Y$^1$ and Y$^2$ are independently nothing or a linker (e.g., having any one or more of the cargo moiety, targeting moiety, general targeting moiety, specific targeting moiety, tracking moiety, solubilizing moiety, cleavable moiety, or the like), or a linker having a cargo moiety or a linker having a targeting moiety; and X$^1$ and X$^2$ are independently nothing, a coupling group, one or more beta-alanine residues, or a polypeptide. In FIG. 8B, Z'$^1$, Z"$^1$, Z'$^2$ and Z"$^2$ are independently a targeting moiety, cargo moiety, or nothing, wherein at least one is a targeting moiety; Y$^1$ and Y$^2$ are independently nothing or a branched linker (e.g., having any one or more of the cargo moiety, targeting moiety, general targeting moiety, specific targeting moiety, tracking moiety, solubilizing moiety, cleavable moiety, or the like), or a branched linker having a cargo moiety or a linker having a targeting moiety; and. X$^1$ and X$^2$ are independently nothing, a coupling group, one or more beta-alanine residues, or a polypeptide. In FIG. 8C, Z'$^1$, Z"$^1$, Z'$^2$ and Z"$^2$ are independently a targeting moiety, cargo moiety, or nothing, wherein at least one is a targeting moiety; Y'$^1$, Y"$^1$, Y'$^2$, and Y"$^2$ are independently nothing or a linker (e.g., having any one or more of the cargo moiety, targeting moiety, general targeting moiety, specific targeting moiety, tracking moiety, solubilizing moiety, cleavable moiety, or the like), or a linker having a cargo moiety or a linker having a targeting moiety; and X$^1$ and X$^2$ are independently nothing, a coupling group, one or more beta-alanine residues, or a polypeptide. In FIG. 8D, Z'$^1$ and Z"$^1$, are independently a targeting moiety, cargo moiety, or nothing, wherein at least one is a targeting moiety; Y" and Y'"$^1$ are independently nothing or a linker (e.g., having any one or more of the cargo moiety, targeting moiety, general targeting moiety, specific targeting moiety, tracking moiety, solubilizing moiety, cleavable moiety, or the like), or a linker having a cargo moiety or a linker having a targeting moiety; and X$^1$ is nothing, a coupling group, one or more beta-alanine residues, or a polypeptide.

Additional sequences shown in Table 2 also provide the improvements described herein for endosomal disruption.

TABLE 2

| SEQ ID NO. | Sequence | Potency (µM) | Efficacy (% of 1) |
|---|---|---|---|
| 1 | Ch1-EEXXSSAWWSYWPPVA-NH$_2$ | 1.3 ± 0.3 | 100 ± 5 |
| 39 | Ac-SSAWWSYWPPVA-NH$_2$ | ND | <2 |
| 40 | Ac-AAAWWAYWPPVA-NH$_2$ | >15 | ND |
| 43 | UUUUWWAYWPPVA-NH$_2$ | 9 ± 3 | 57 ± 7 |
| 44 | UUUUWWAYWPPVV-NH$_2$ | 5 ± 1 | 98 ± 2 |
| 45 | UUUUAWAYWPPVV-NH$_2$ | ND | <10 |
| 46 | UUUUWAAYWPPVV-NH$_2$ | ND | <10 |
| 47 | UUUUWWAAWPPVV-NH$_2$ | >15 | ND |
| 48 | UUUUWWAYAPPVV-NH$_2$ | ND | <10 |
| 49 | UUUUWWAYWAPVV-NH$_2$ | ND | 35 ± 2 |
| 50 | UUUUWWAYWPAVV-NH$_2$ | 9 ± 3 | 54 ± 3 |
| 51 | UUUUWWAYWPPAV-NH$_2$ | >15 | ND |
| 52 | UUUUYWAWWPPVV-NH$_2$ | 3.2 ± 1.4 | 105 ± 19 |
| 53 | UUUUWYAWWPPVV-NH$_2$ | 6.7 ± 0.8 | 96 ± 12 |
| 54 | UUUUWWAWYPPVV-NH$_2$ | 5.4 ± 1.6 | 101 ± 2 |
| 78 | Ac-UUUUWWAWYPPVV-NH$_2$ | 2.3 ± 0.3 | 70 ± 2 |
| 79 | UUUUWWAWWAWYPPVV-NH$_2$ | 0.22 ± 0.06 | 86 ± 5 |
| 80 | UUUUWYAWYAWYPPVV-NH$_2$ | 0.28 ± 0.1 | 113 ± 4 |
| 81 | UUUUAWYAWYWYPPVV-NH$_2$ | 9 ± 6 | 83 ± 13 |
| 82 | Ac-UUUUWYAWYAWYPPVV-NH$_2$ | 0.8 ± 0.2 | 85 ± 7 |
| 83 | PB-GUUUUWYAWYAWYPPVV-NH$_2$ | 1.9 ± 0.3 | 123 ± 3 |
| 84 | Ch2-EEOOUUUWYAWYAWYPPVV-NH$_2$ | 0.04 ± 0.01 | 134 ± 1 |
| 85 | UUUUYYAYYAYYPPVV-NH$_2$ | 4 ± 1 | >125 |
| 86 | Ch1-EEOOUUUUYYYYPPVV-NH$_2$ | 0.08 ± 0.01 | 125 ± 10 |
| 87 | Ch2-EEOOUUUUYYAYYAYYPPVV-NH$_2$ | <0.05 | >125 |

In Table 2, the sequences of synthetic peptides, potency and efficacy as disruptors of endosomes is shown. Natural amino acids are represented by single letter codes. Codes for non-standard elements are as follows: Ch1: (3β-Cholest-5-en-3-yl-ammonio)pentanoyl; Ch2: (Cholester-3-yl)oxy-βAla-βAla; X: ε-Ahx; U: Aib; PB: Pacific Blue fluorophore. O: 3-(2-(2-(2-aminoethoxy)ethoxy)ethoxy)propanyl. Potency (EC$_{50}$) and efficacy (% of the effect of previously published (JACS 2008, 130, 10064-10065) compound 1 based on the calculated span of the dose-response curve) ±standard deviation in Jurkat lymphocytes were measured by flow cytometry after treatment of cells with peptides and a previously published (JACS 2008, 130, 10064-10065) disulfide-linked fluorescent probe (2.5 µM) for 14 h.

In Table 3, the toxicity (Tox., IC$_{50}$) to this cell line was determined by flow cytometry analysis of light scattering after treatment for 48 h at 37° C. Thermodynamic aqueous solubility (Sol.) in PBS (pH 7.4) was measured by sonication of solutions (1 mL) containing visible solid for 30 min at 22° C., gentle rocking of these samples for 24 h at 22° C., centrifugation (1 h, 16000 g), and absorbance (280 nm) of the supernatant to determine concentration based on calculated extinction coefficients. Measurements represent duplicate or more replicates, with active peptides subjected to multiple replicates. ND: not determined. The peptide was non-toxic and soluble in cell culture medium at this concentration.

TABLE 3

| SEQ ID NO. | Toxicity (μM) | Solubility (μM) |
|---|---|---|
| 1 | 9 ± 1 | 80 ± 8 |
| 39 | ND | 137 ± 8 |
| 40 | ND | 41 ± 2 |
| 43 | ND | 40 ± 2 |
| 44 | >16$^a$ | 22 ± 1 |
| 45 | ND | 86 ± 5 |
| 46 | ND | 86 ± 5 |
| 47 | ND | 63 ± 3 |
| 48 | ND | 86 ± 5 |
| 49 | ND | 21 ± 2 |
| 50 | ND | 22 ± 2 |
| 51 | ND | 48 ± 3 |
| 52 | >16$^a$ | 21 ± 1 |
| 53 | >>16$^a$ | 29 ± 3 |
| 54 | >>16$^a$ | 8 ± 1 |
| 78 | >>16$^a$ | 5 ± 1 |
| 79 | >>16$^a$ | 2 ± 1 |
| 80 | >>16$^a$ | 5 ± 2 |
| 81 | >>8$^a$ | 3 ± 1 |
| 82 | >>16$^a$ | 2 ± 1 |
| 83 | >>16$^a$ | 3 ± 1 |
| 84 | 11 ± 2 | 21 ± 1 |

Figure 9:
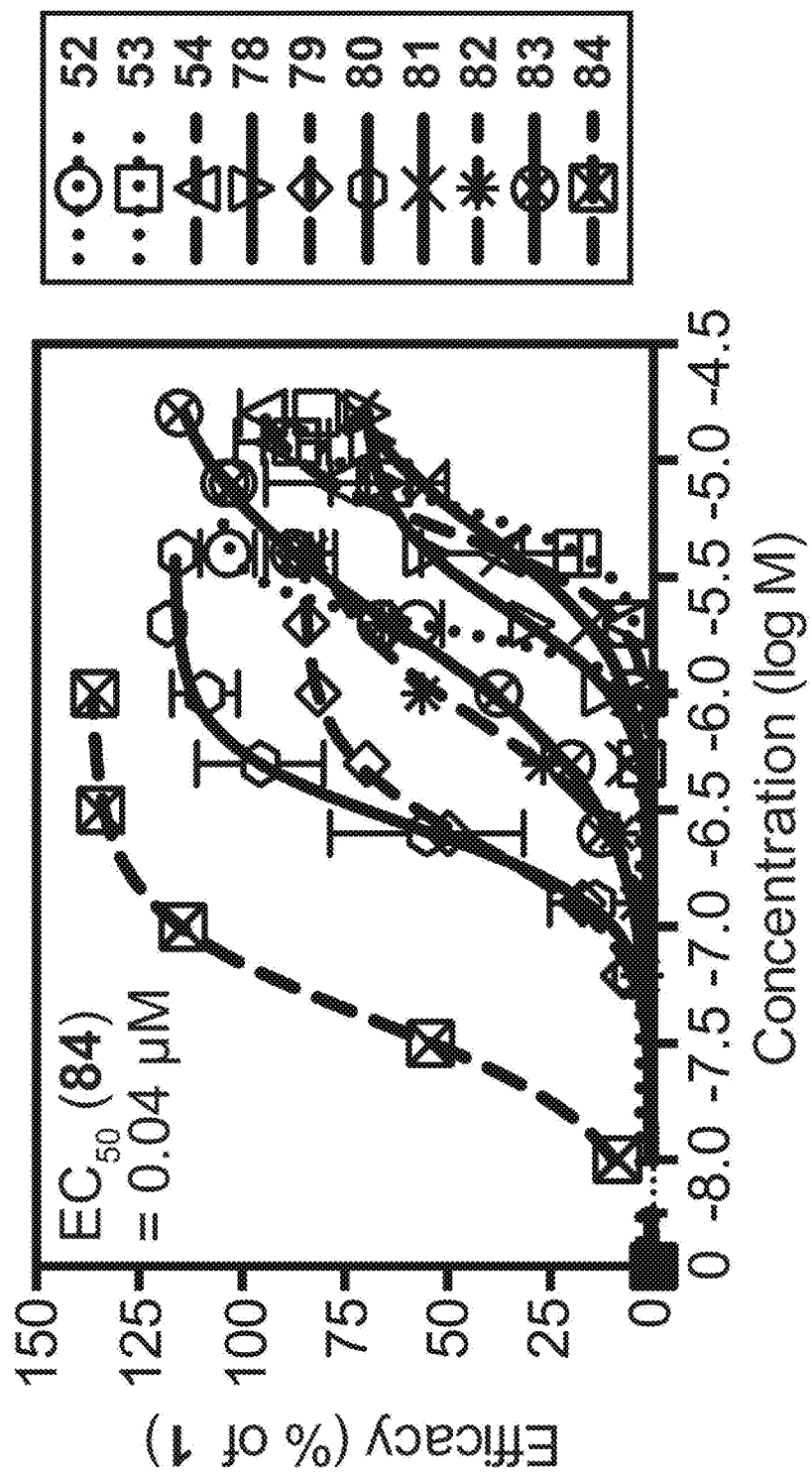
FIG. 9 shows a dose-response curve for the efficacy of endosomal release obtained by conthrmationally-constrained kinked peptides.

FIG. 9 shows the endosomal disruption efficacy of the sequences of SEQ ID Nos: 52, 53, 54, 78, 79, 80, 81, 82, 83, and 84.

Accordingly, some representative peptide sequences, which can include only the amino acids in the sequences, or the amino acids in addition to the end groups (E.g., Ac, PB, Chol, etc. are shown below. These sequences are also successful as membrane disruption agents.

UUUUWWAWWAWYPPVV-CONH$_2$ (SEQ ID NO: 79)

UUUUWYAWYAWYPPVV-CONH$_2$ (SEQ ID NO: 80)

Ac-UUUUWYAWYAWYPPVV-CONH$_2$ (SEQ ID NO: 82)

PB-GUUUUWYAWYAWYPPVV-CONH$_2$ (SEQ ID NO: 83)

Chol-EEOOUUUUWYAWYAWYPPVV-CONH$_2$ (SEQ ID NO: 84)

UUUUYYAYYAYYPPVV-CONH$_2$ (SEQ ID NO: 85)

Chol-EEOOUUUYYAYYAYYPPVV-CONH$_2$ (SEQ ID NO: 87)

UUUUYWAYWAYWPPVV-CONH$_2$ (SEQ ID NO: 88)

UUUUWWAWWAWWPPVV-CONH$_2$ (SEQ ID NO: 89)

Ac-UUUUWWAWWAWYPPVV-CONH$_2$ (SEQ ID NO: 90)

Ac-UUUUYYAYYAYYPPVV-CONH$_2$ (SEQ ID NO: 91)

More general peptide sequences that describe this family include:

UUUUXXAXXAXXPPVV-CONH$_2$ (SEQ ID NO: 92), where each X is tryptophan or tyrosine;

UUUUXXAXXAXXPPVV-CONH$_2$ (SEQ ID NO: 93), where each X is any aromatic amino acid;

BBBBXXAXXAXXPPVV-CONH$_2$ (SEQ ID NO: 94), where each X is any aromatic amino acid, and each B is any aliphatic amino acid, 2-amino isobutyric acid (U, Aib), or nothing;

BBBBXXAXXAXXPPBB-CONH$_2$ (SEQ ID NO: 95), where each X is any aromatic amino acid, and each B is any aliphatic amino acid. 2-amino isobutyric acid (U, Aib), other amino acid, or nothing;

BBBBXXAXXAXXPPBB-CONH$_2$ (SEQ ID NO: 96), where each X is any aromatic amino acid, and each B is any aliphatic amino acid, 2-amino isobutyric acid (U, Aib), other amino acid, or nothing, where the number of B amino acids can vary from 1-10 or each B amino acid can be from 1-10 amino acids; and BBBBXXAXXAXXZZBB-CONH$_2$ (SEQ ID NO: 97), where X is any aromatic amino acid, and B is any aliphatic amino acid, 2-amino isobutyric acid (U, Aib), other amino acid, or nothing, where the number of B amino acids can vary from 1-10 or each B amino acid can be from 1-10 amino acids, and Z is proline or glycine or nothing.

In one embodiment, the targeting moiety is on the C-terminus of the peptide, wherein the kinked portion or the kinked portion, peptide linker and conformationally-constraining portion includes one of SEQ ID NOs: 1, 5-38, 40-54, 61-69, or 78-97. Alternately, the targeting moiety is on the N-terminus of the peptide, wherein the kinked portion or the kinked portion, peptide linker and conformationally-constraining portion includes one of SEQ ID NOs: 1, 5-38, 40-54, 61-69, or 78-97. Also, any of the embodiments herein that includes an endosomal disrupting peptide can include one of the peptides of SEQ ID Nos: 78-97. In some instances, the peptides have sequences of SEQ ID Nos: 78-92.

In one embodiment, the cell-targeting compound can include one of Formulae 2-2C, 3-3C, or 4-4C, wherein: ED-KP is the endosomal-disrupting kinked peptide having one or more amino acids independently selected from proline and glycine; CC-Peptide includes a peptide having one or more 2-aminoisobutyric acid residues or derivatives thereof (e.g., methyl replaced with longer alkyls) that conformationally-constrains the ED-KP; the Peptide independently includes natural, unnatural, essential or non-essential aromatic, aliphatic, or other amino acids, or derivatives thereof having L or D configuration; Xaa, Xaa$^1$, and Xaa$^2$ are independently one or more natural or non-natural amino acids, essential amino acids, or non-essential amino acids, or derivatives of amino acids having L or D configuration; L1 and L2 are independently linkers; n1 and n3 are independently an integer greater than 0 and less than 50; n2 and n4 are independently 0-50; $Z^1$ and $Z^2$ are independently a targeting moiety, cargo moiety, or nothing, wherein at least one is a targeting moiety; $Y^1$ and $Y^2$ are independently nothing or a linker, or a linker having a cargo moiety; and X[1] and X[2] are independently nothing, a coupling group, one or more beta-alanine residues, or a polypeptide.

In one embodiment, the cell-targeting compound can include one of Formulae 6-6C, 7-7C, or 8-8C, wherein: ED-KP is the endosomal-disrupting kinked peptide having one or more amino acids independently selected from proline and glycine; CCM includes a moiety having one or more 2-aminoisobutyric acid residues or derivatives thereof that conformationally constrains the ED-KP; Peptide independently includes natural, unnatural, essential or non-essential aromatic, aliphatic, or other amino acids, or derivatives thereof having L or D configuration; Xaa, Xaa[1], and Xaa[2] are independently one or more natural or non-natural amino acids, essential amino acids, or non-essential amino acids, or derivatives of amino acids having L or D configuration; L1 and L2 are independently linkers; n1 and n3 are independently an integer greater than 0 and less than 50; n2 and n4 are independently 0-50; Z' and Z[2] are independently a targeting moiety, cargo moiety, or nothing, wherein at least one is a targeting moiety; Y[1] and Y[2] are independently nothing or a linker, or a linker having a cargo moiety; and X[1] and X[2] are independently nothing, a coupling group, one or more beta-alanine residues, or a polypeptide.

In one embodiment, the cell-targeting compound can include one of Formulae 10-10C, 11-11C, or 12-12C wherein: KP and KP1 are independently one or more amino acids independently selected from proline and glycine that can cause the endosomal-disrupting kinked peptide to kink; Aib is a 2-aminoisobutyric acid residue; Xaa, Xaa[1], and Xaa[2] are independently one or more natural or non-natural amino acids, essential amino acids, or non-essential amino acids, or derivatives of amino acids having L or D configuration; Z[1] and Z[2] are independently a targeting moiety, cargo moiety, or nothing, wherein at least one is a targeting moiety; Y[1] and Y[2] are independently nothing or a linker, or a linker having a cargo moiety; X[1] and X[2] are independently nothing, a coupling group, one or more beta-alanine residues, or a polypeptide; and n1 and n3 are independently an integer greater than 0 and less than or equal to 50; n2 n4, n5, n6, and n7 are independently 0-50.

In one embodiment, the cell-targeting compound can include a cargo moiety linked to the peptide. In one aspect, the cargo moiety is a general targeting moiety or hydrophobic moiety that has hydrophobic attraction to cell membranes, wherein the cargo moiety is not a specific targeting moiety that targets a receptor or ligand on a cell surface, which allows the cargo moiety to insert into the cell membrane, such as surface or endosome. In one aspect, the cargo moiety is linked at an internal portion of the cell-targeting compound between the targeting moiety and the peptide. In one aspect, the cargo moiety is linked at an end of the peptide opposite of the targeting moiety. In one aspect, the cargo moiety is a therapeutic agent, pharmaceutical, nutraceutical, diagnostic agent, assay agent, tracking agent, suicide agent, toxin, or any other agent. In one aspect, the n1, n2, n3, n4, n5, n6, and n7 are independently an integer greater than 0 and less than or equal to 50. In one aspect, the targeting moiety is on the C-terminus. In one aspect, the targeting moiety is on the N-terminus. In one aspect, Z[1] and Z[2] are independently a targeting moiety or cargo moiety, wherein at least one is a targeting moiety. In one aspect, Y[1] and Y[2] are each a linker. In one aspect, X[1] and X[2] are each independently one or more beta-alanine residues or linkers including such beta-alanine residues. In one aspect, Y[1] and Y[2] are each a linker and X[1] and X[2] are each independently one or more beta-alanine residues. In one aspect, Y[1] and Y[2] are each a linker that includes one or more natural or non-natural amino acids, essential amino acids, or non-essential amino acids, or derivatives of amino acids having L or D configuration or peptide thereof. In one aspect, $X^1$-$(Aib)_{n1}$-$(Xaa^1)_{n2}$-$(KP)_{n3}$-$(Xaa^2)_{n4}$ includes one of SEQ ID NOs: 1, 5-38, 40-54, 61-69, or 78-97. In one aspect, n1 is 1, 2, 3, or 4.

In any of the embodiments, KP and KP1 independently include a kinked peptide or an amino acid that can cause a peptide to kink, or KP and KP1 are amino acids that can cause a peptide to kink.

In any of the embodiments, n1, n2, n3, n4, n5, n6, and n7 are independently 0-50, or n1, n2, n3, n4, n5, n6, and n7 are independently 1-50, or 0, 1, 2, 3, 4, 5, 6, 7, 8, 9, 10, 15, 20, 25, 30, 35, 40, 45 or 50 or other integer value in this range.

In any of the embodiments, Aib is 2-aminoisobutyric acid or a related alpha, alpha-disubstituted amino acid, such as diethylglycine, 4-amino-4-tetrahydropyrancathoxylic acid, 1-amino-1-cyclobutane carboxylic acid, 1-amino-1-cyclopentane carboxylic acid, or 1-amino-1-cyclohexane carboxylic acid.

In any of the embodiments, X1, Y1, Z1, X2, Y2, Z2 in any of the formulae are interchangeable and/or repeated in any order in any amount. This can be: Z—Z—Y—Y—X—X; ZYZYX; ZXYZXY; ZYZX; or any other permutation. The X1, Y1, X2, Y2, in any of the formulae can be linear (Y) or branched (Y', Y").

In any of the embodiments, X1, Y1, Z1, X2, Y2, Z2 in any of the formulae may also include a tracking moiety (T), such as a visualization agent, or be devoid of tracking moiety It has been discovered that incorporation of one to five helix-promoting aminoisobutyric acid (Aib, U) residues enhances the endosome disruptive activity of peptides. Further improvement in activity and/or potency was achieved by addition of a WWA, WYA, YWA, or YYA tripeptide sequence and substitution of Ala with Val at the C-terminus of these compounds.

In assays, release of fluorophore (FIGS. 10A-10C) from endosomes into the cytosol and nucleus enhances cellular fluorescence due in part to changes in pH. These peptides do not require a membrane-targeting cholesterol moiety but similarly accumulate in endosomes, as evidenced by studies of fluorescent derivatives, and they exhibit high potency as endosome disruptive agents.

Figure 10A:
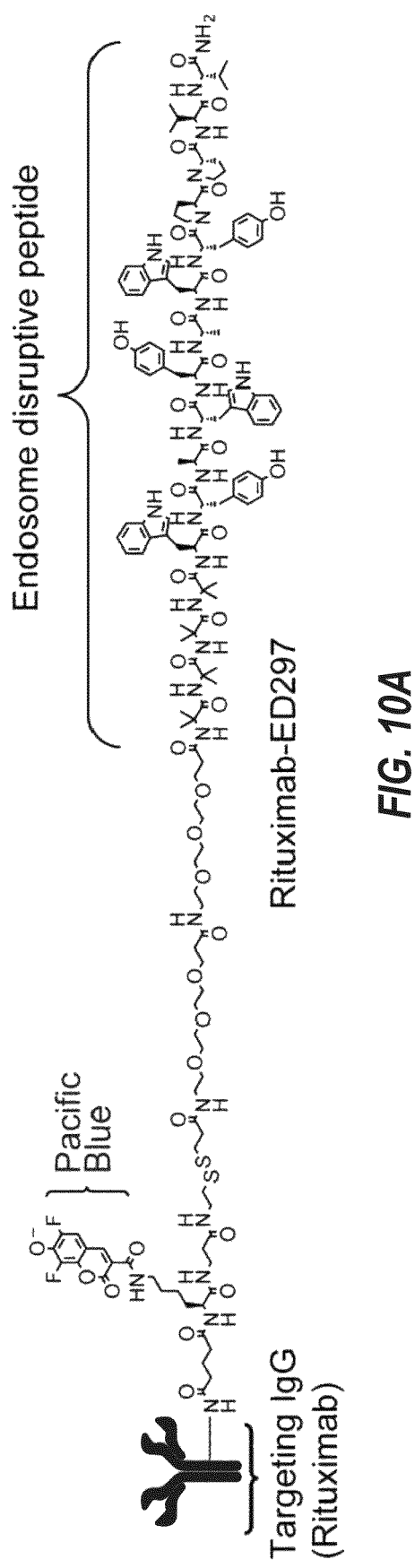
FIG. 10A shows a conformationally-constrained kinked peptide linked to an antibody targeting moiety and having a tracking agent.

While FIGS. 10A-10C show data with Rituximab, other antibodies, or antibody fragments such as Fab fragments, or Fc fragments, or derivatives thereof, can be used. This allows an antibody for a certain target, such as a receptor, on a cell to be used to provide the compounds to the endosome of the cell for endosomal disruption.

Figure 11:
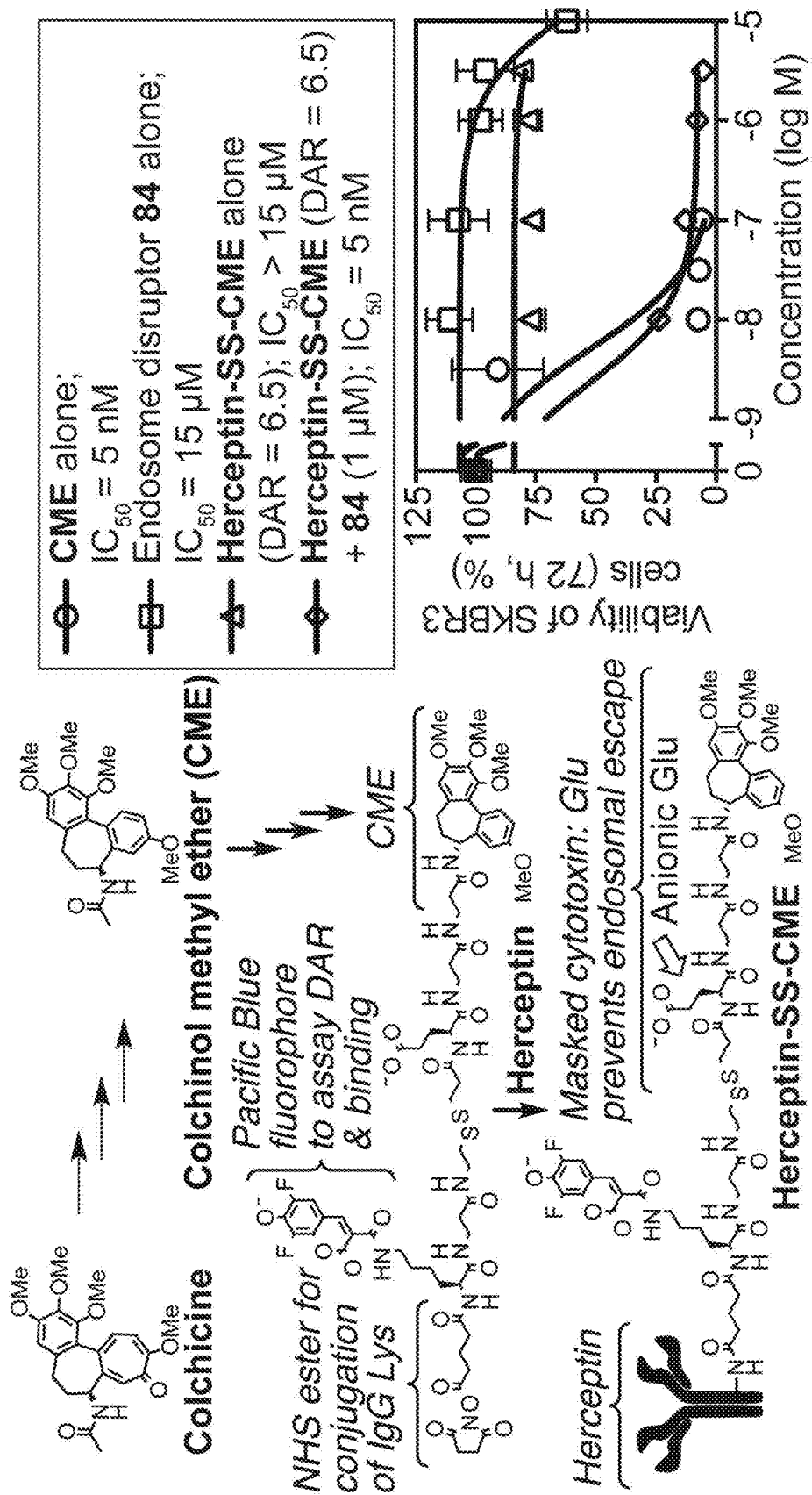
FIG. 11 shows a toxin having an antibody targeting moiety and synthesis thereof as well as a dose-response curve for cell viability with or without the conformationally-constrained kinked peptide having the peptide with SEQ ID NO: 84.

It was found that endosome disruptive peptides can exhibit synergistic cytotoxicity with antibody conjugates. To investigate whether endosome disruptive peptides might enable release of a cytotoxin from endosomes, we treated SKBr3 breast cancer cells with a Herceptin-cytotoxin conjugate. The cytotoxin that we investigated was a synthetic derivative of the natural product colchicine termed colchinol methyl ether. CME was chosen as it exhibits greater specificity than colchicine as a tubulin-binding cytotoxin. As shown in FIG. 11, a colchinol methyl ether derivative was linked to an amine reactive NHS ester via a cleavable disulfide linker that also included the Pacific Blue fluorophore. This fluorophore is orthogonal to fluorescein, and it was included for determination of the drug-antibody ratio (DAR) and for assays of binding of antibody conjugates to targets by microscopy.

FIG. 11 shows the structures of natural (colchicine) and synthetic (CME) tubulin polymerization inhibitors, a disulfide-linked colchinol-NHS ester used for antibody conjugation, and a Herceptin-disulfide-CME conjugate. FIG. 11 also shows the synergistic cytotoxicity towards SKBR3 breast cancer cells from treatment with endosome disruptive peptide 84 (e.g., SEQ ID NO: 84) and the Herceptin-SS-CME conjugate. Comparison of the cytotoxic $IC_{50}$ values of disulfide-linked Herceptin-SS-CME alone ($IC_{50}$=15 μM), and in the presence of peptide 84 (at a fixed concentration of 1 μM) revealed that the addition of peptide 84 synergistically enhances the toxicity of Herceptin-SS-CME by over 100-fold ($IC_{50}$(Herceptin-SS-CME+84)=5 nM). The low toxicity of the Herceptin-SS-CME conjugate alone can be explained by the poor penetration of the highly polar glutamic acid-containing CME cargo across endosomal membranes, limiting access to the target tubulin in the cytoplasm. When trapped and sequestered in endosomes, this cargo is unable to manifest cytotoxicity. However, release of this agent from endosomes mediated by the endosome disruptive peptide 84 triggers potent cytotoxic action against tubulin the cytosol. Thus, the compounds described herein can provide endosomal disruption so that a second agent, such as one with a targeting moiety and a cargo (e.g., drug) can escape the endosome when disrupted.

Figure 12A:
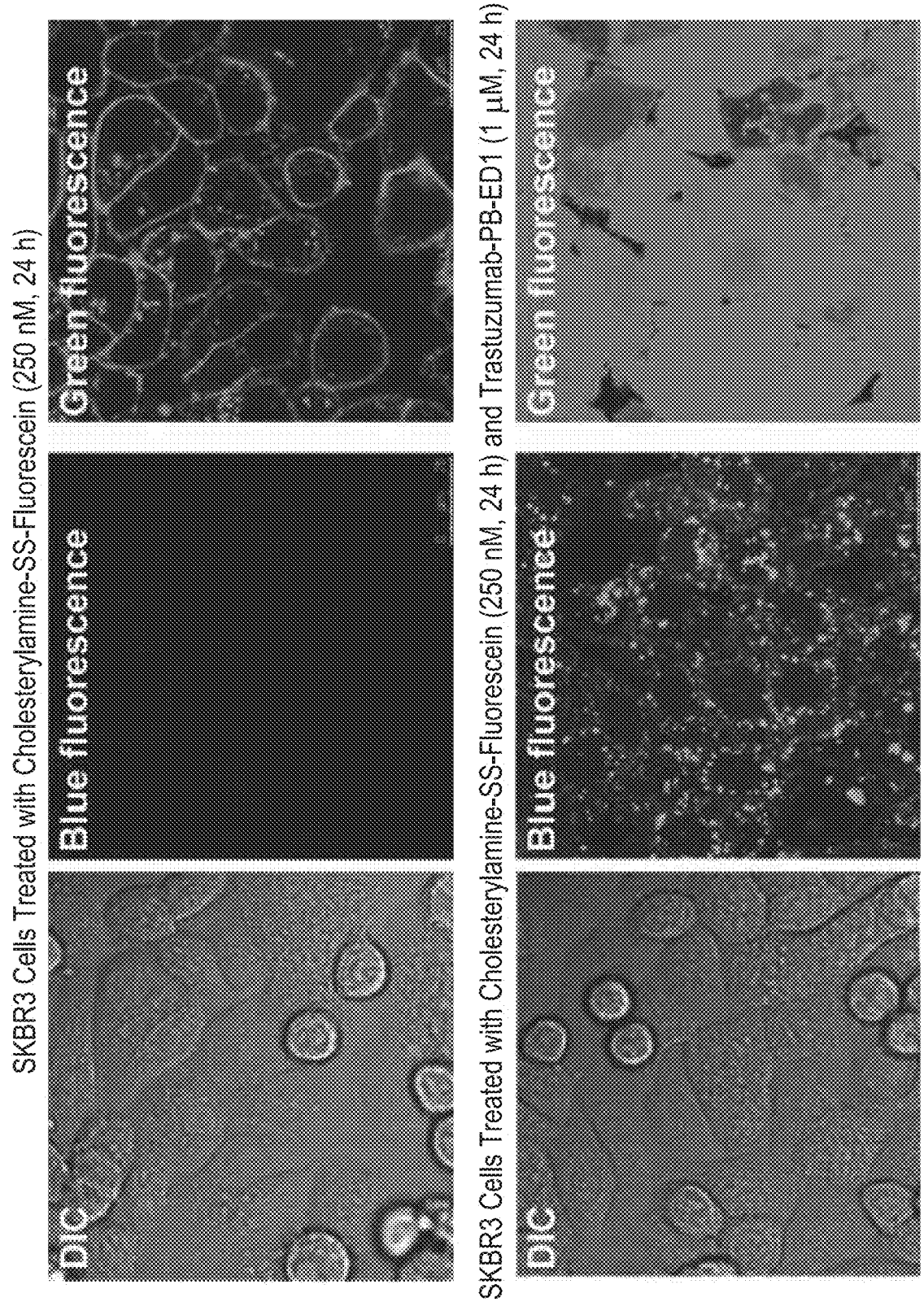
FIGS. 12A-12B shows images of SKBR3 cells that are treated with a Cholesterylamine-SS-Fluorescein probe with and without different conformationally-constrained kinked peptides.
Figure 12B:
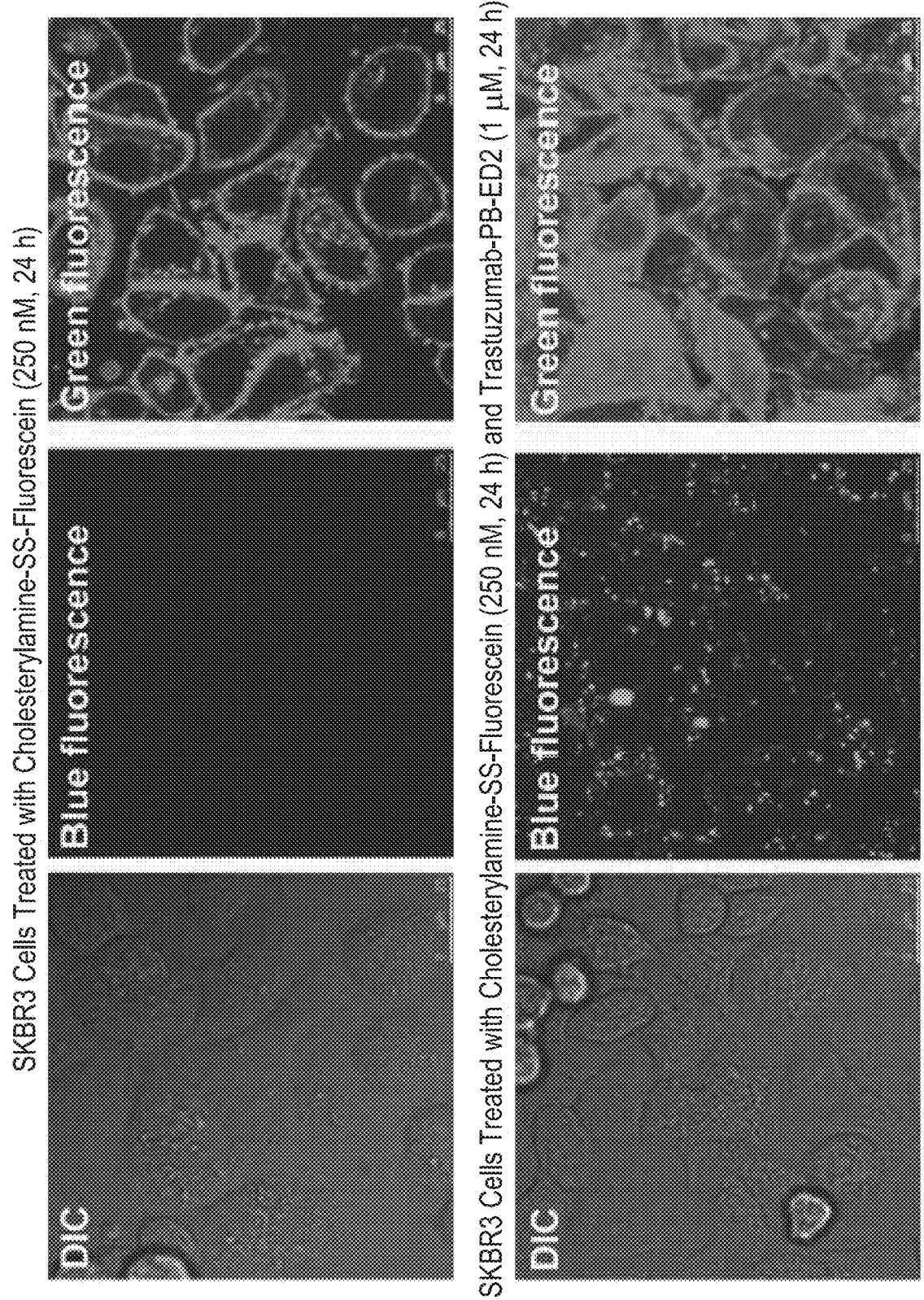

FIGS. 12A-12B includes data of functional assays of endosome disruption by Trastuzumab-PB-ED1 (Compare Panels of FIG. 12A) and Trastuzumab-PB-ED2 (Compare Panels of FIG. 12B). Trastuzamab-PB-LD1 is the compound of FIG. 7 with the antibody being Trastuzamab. Trastuzumab-PB-ED2 is the compound of FIG. 7 with the antibody being Trastuzamab but the cholesteryl carbamate is replaced by an amide derived from palmitic acid and the endosome disruptive peptide is replaced by the peptide: UUUUWY-AWYAWYPPVV-CONH$_2$. Disruption of endosomes of SKBR3 cells is evidenced by release of green fluorescence of Cholesterylamine-SS-Fluorescein from endosomes into the cytoplasm and nucleus as imaged by confocal laser scanning microscopy.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety: PCT Publication WO 2011/019942; U.S. Publication 2010/0041773; α-Helix Stabilization by Natural and Unnatural Amino Acids with Alkyl Side Chains; PC Lyu et al.; *Proc. Natl. Aca. Sci USA;* Vol. 88, pp. 5317-5320, June 1991; An All-Hydrocarbon Cross-Linking System for Enhancing the Helicity and Metabolic Stability of Peptides; CE Schafmeister et al.; *J. Am. Chem. Soc.;* Vol. 122, pp. 5891-5892, 2000; Factors Governing Helical Preference of Peptides Containing Multiple α,α-dialkyl Amino Acids; GR Marshall et al.; *Proc. Natl. Acad. Sci. USA;* Vol. 87, pp. 487-491, January 1990; Helix Propensities of the Amino Acids Measured in Alanine-Based Peptides without Helix-Stabilizing Side-Chain interactions; A Chakrabartty et al.; *Protein Science;* Vol. 3, pp. 843-852, 1994; NMR Structures of a Viral Peptide Inserted in Artificial Membranes; M Galloux et al.; *The Journal of Biological Chemistry;* Vol. 285, No. 25, pp. 19409-19421 Jun. 18, 2010; Amino Acid Preferences for Specific Locations at the Ends of a Helices; J S Richardson et al.; *Science;* Vol. 240, pp. 1648-1652, Jun. 17, 1988; Structural and Functional Implications of a Proline Residue in the Antimicrobial Peptide Gaegurin; J Y Suh; *Eur. Biochem.;* Vol. 266, pp. 665-674, 1999; Using an Azobenzene Cross-Linker to Either Increase or Decrease Peptide Helix Content upon Trans-to-Cis Photoisomerization; DG Flint; *Chemistry & Biology;* Vol. 9, pp. 391-397, March 2002; Endocytic Delivery of Vancomycin Mediated by a Synthetic Cell Surface Receptor: Rescue of Bacterially Infected Mammalian Cells and Tissue Targeting In Vivo; S Boonyarattanakalin et al.; *J. Am. Chem. Soc.;* Vol. 129, pp. 268-269, 2007; Selective Disruption of Early/Recycling Endosomes: Release of Disulfide-Linked Cargo Mediated by an N-Alkyl-3β-Cholesterylamine-Capped Peptide; Q Sun et al.; *J. Am. Chem. Soc.;* Vol. 130, pp. 10064-10065, 2008.

The invention claimed is:

1. A peptide sequence comprising:
   one of SEQ ID NOs: 92-97.

2. A peptide sequence, comprising:
   one of SEQ ID NOs: 5-38, 40-54, 61-69, or 78-91.

3. The peptide sequence of claim 2, comprising:
   one of SEQ ID NOs: 78-91.

4. A cell-targeting compound comprising:
   one or more peptides having a conformationally-constraining portion, and a kinked portion linked through a peptide linker to the conformationally-constraining portion that conformationally constrains the kinked portion, the kinked portion, peptide linker and conformationally-constraining portion includes the peptide sequence of claim 1; and
   at least one targeting moiety linked to an end of the one or more peptides.

5. The cell-targeting compound of claim 4, wherein at least one targeting moiety is on the C-terminus of the peptide.

6. The cell-targeting compound of claim 4, wherein at least one targeting moiety is on the N-terminus of the peptide.

7. The cell-targeting compound of claim 4, comprising one of Formulae 2-2C, 3-3C, or 4-4C, wherein:
   ED-KP is an endosomal-disrupting kinked peptide having one or more amino acids independently selected from proline and glycine;
   CC-Peptide includes a peptide having one or more 2-aminoisobutyric acid residues that conformationally-constrains the ED-KP;
   Peptide independently includes natural, unnatural, essential or non-essential aromatic, aliphatic, or other amino acids, or having L or D configuration;
   Xaa, $Xaa^1$, and $Xaa^2$ are independently one or more natural or non-natural amino acids, essential amino acids, or non-essential amino acids, or amino acids having L or D configuration;
   L1 and L2 are independently linkers;
   n1 and n3 are independently an integer greater than 0 and less than 50;
   n2 and n4 are independently 0-50;
   $Z^1$ and $Z^2$ are independently a targeting moiety, cargo moiety, or nothing, wherein at least one is a targeting moiety;
   $Y^1$ and $Y^2$ are independently nothing or a linker, or a linker having a cargo moiety; and
   $X^1$ and $X^2$ are independently nothing, a coupling group, one or more beta-alanine residues, or a polypeptide, $$\text{Formula } 2 = Z^1\text{—}Y^1\text{—}X^1\text{—}(\text{CC-Peptide})_{n1}\text{-}(\text{Peptide})_{n2}\text{-}(\text{ED-KP})_{n3}\text{-}(\text{Peptide})_{n4}\text{-}X^2\text{—}Y^2\text{—}Z^2;$$

$$\text{Formula } 2A = Z^1\text{—}Y^1\text{—}X^1\text{—}(\text{CC-Peptide})_{n1}\text{-}(L1)_{n2}\text{-}(\text{ED-KP})_{n3}\text{-}(L2)_{n4}\text{-}X^2\text{—}Y^2\text{—}Z^2;$$

Formula 2B $=Z^1-Y^1-X^1-(CC\text{-Peptide})_{n1}-(Xaa)_{n2}-(ED\text{-}KP)_{n3}-(Xaa)_{n4}-X^2-Y^2-Z^2$;

Formula 2C $=Z^1-Y^1-X^1-(CC\text{-Peptide})_{n1}-(Xaa^1)_{n2}-(ED\text{-}KP)_{n3}-(Xaa^2)_{n4}-X^2-Y^2-Z^2$;

Formula 3$=Z^1-Y^1-X^1-(CC\text{-Peptide})_{n1}-(Peptide)_{n2}-(ED\text{-}KP)_{n3}-(Peptide)_{n4}$;

Formula 3A $=Z^1-Y^1-X^1-(CC\text{-Peptide})_{n1}-(L1)_{n2}-(ED\text{-}KP)_{n3}-(L2)_{n4}$;

Formula 3B $=Z^1-Y^1-X^1-(CC\text{-Peptide})^{n1}-(Xaa)_{n2}-(ED\text{-}KP)_{n3}-(Xaa)_{n4}$;

Formula 3C $=Z^1-Y^1-X^1-(CC\text{-Peptide})_{n1}-(Xaa^1)_{n2}-(ED\text{-}KP)_{n3}-(Xaa^2)_{n4}$;

Formula 4$=(CC\text{-Peptide})_{n1}-(Peptide)_{n2}-(ED\text{-}KP)_{n3}-(Peptide)_{n4}-X^2-Y^2-Z^2$;

Formula 4A $=(CC\text{-Peptide})_{n1}-(L1)_{n2}-(ED\text{-}KP)_{n3}-(L2)_4-X^2-Y^2-Z^2$;

Formula 4B $=(CC\text{-Peptide})_{n1}-(Xaa)_{n2}-(ED\text{-}KP)_{n3}-(Xaa)_{n4}-X^2-Y^2-Z^2$; and Formula 4C $=(CC\text{-Peptide})_{n1}-(Xaa^1)_{n2}-(ED\text{-}KP)_{n3}-(Xaa^2)_{n4}-X^2-Y^2-Z^2$.

8. The cell-targeting compound of claim 4, comprising one of Formulae 6-6C, 7-7C, or 8-8C, wherein:

ED-KP is an endosomal-disrupting kinked peptide having one or more amino acids independently selected from proline and glycine;

CCM includes a moiety having one or more 2-aminoisobutyric acid residues that conformationally constrains the ED-KP;

Peptide independently includes natural, unnatural, essential or non-essential aromatic, aliphatic, or other amino acids, or having L or D configuration;

Xaa, Xaa$_1$, and Xaa$^2$ are independently one or more natural or non-natural amino acids, essential amino acids, or non-essential amino acids, or amino acids having L or D configuration;

L$_1$ and L2 are independently linkers;

n1 and n3 are independently an integer greater than 0 and less than 50;

n2 and n4 are independently 0-50;

Z$^1$ and Z$^2$ are independently a targeting moiety, cargo moiety, or nothing, wherein at least one is a targeting moiety;

Y$^1$ and Y$^2$ are independently nothing or a linker, or a linker having a cargo moiety; and X$^1$ and X$^2$ are independently nothing, a coupling group, one or more beta-alanine residues, or a polypeptide, Formula 6$=Z^1-Y^1-X^1-(CCM)_{n1}-(Peptide)_{n2}-(ED\text{-}KP)_{n3}-(Peptide)_{n4}-X^2-Y^2-Z^2$;

Formula 6A $=Z^1-Y^1-X^1-(CCM)_{n1}-(L1)_{n2}-(ED\text{-}KP)_{n3}-(L2)_{n4}-X^2-Y^2-Z^2$;

Formula 6B $=Z^1-Y^1-X^1-(CCM)_{n1}-(Xaa)_{n2}-(ED\text{-}KP)_{n3}-(Xaa)_{n4}-X^2-Y^2-Z^2$;

Formula 6C $=Z^1-Y^1-X^1-(CCM)_{n1}-(Xaa^1)_{n2}-(ED\text{-}KP)_{n3}-(Xaa^2)_{n4}-X^2-Y^2-Z^2$;

Formula 7$=Z^1-Y^1-X^1-(CCM)_{n1}-(Peptide)_{n2}-(ED\text{-}KP)_{n3}-(Peptide)_{n4}$;

Formula 7A $=Z^1-Y^1-X^1-(CCM)_{n1}-(L1)_{n2}-(ED\text{-}KP)_{n3}-(L2)_{n4}$;

Formula 7B $=Z^1-Y^1-X^1-(CCM)_{n1}-(Xaa)_{n2}-(ED\text{-}KP)_{n3}-(Xaa)_{n4}$;

Formula 7C $=Z^1-Y^1-X^1-(CCM)_{n1}-(Xaa^1)_{n2}-(ED\text{-}KP)_{n3}-(Xaa^2)_{n4}$;

Formula 8$=(CCM)_{n1}-(Peptide)_{n2}-(ED\text{-}KP)_{n3}-(Peptide)_{n4}-X^2-Y^2-Z^2$;

Formula 8A $=(CCM)_{n1}-(L1)_{n2}-(ED\text{-}KP)_{n3}-(L2)_{n4}-X^2-Y^2-Z^2$;

Formula 8B $=(CCM)_{n1}-(Xaa)_{n2}-(ED\text{-}KP)_{n3}-(Xaa)_{n4}-X^2-Y^2-Z^2$; and Formula 8C $=(CCM)_{n1}-(Xaa^1)_{n2}-(ED\text{-}KP)_{n3}-(Xaa^2)_{n4}-X^2-Y^2-Z^2$.

9. The cell-targeting compound of claim 4, comprising one of Formulae 10-10C, 11-11C, or 12-12C wherein:

KP and KP1 are independently one or more amino acids independently selected from proline and glycine that can cause the peptide to kink;

Aib is a 2-aminoisobutyric acid residue;

Xaa, Xaa$^1$, and Xaa$^2$ are independently one or more natural or non-natural amino acids, essential amino acids, or non-essential amino acids, or amino acids having L or D configuration;

Z$^1$ and Z$^2$ are independently a targeting moiety, cargo moiety, or nothing, wherein at least one is a targeting moiety;

Y$^1$ and Y$^2$ are independently nothing or a linker, or a linker having a cargo moiety;

X$^1$ and X$^2$ are independently nothing, a coupling group, one or more beta-alanine residues, or a polypeptide; and n1 and n3 are independently an integer greater than 0 and less than or equal to 50;

n2 n4, n5, n6, and n7 are independently 0-50,

Formula 10$=Z^1-Y^1-X^1-(Aib)_{n1}-(Xaa^1)_{n2}-(KP)_{n3}-(Xaa^2)_{n4}-X^2-Y^2-Z^2$;

Formula 11$=Z^1-Y^1-X^1-(Aib)_{n1}-(Xaa^1)_{n2}-(KP)_{n3}-(Xaa^2)_{n4}$;

Formula 12$=(Aib)_{n1}-(Xaa^1)_{n2}-(KP)_{n3}-(Xaa^2)_{n4}-X^2-Y^2-Z^2$;

Formula 10A $=Z^1-Y^1-X^1-(Aib)_{n1}-(Xaa^1)_{n2}-(KP)_{n3}-(Xaa^2)_{n4}-(KP1)_{n5}-X^2-Y^2-Z^2$;

Formula 11A $=Z^1-Y^1-X^1-(Aib)_{n1}-(Xaa^1)_{n2}-(KP)_{n3}-(Xaa^2)_{n4}-(KP1)_{n5}$;

Formula 12A $=(Aib)_{n1}-(Xaa^1)_{n2}-(KP)_{n3}-(Xaa^2)_{n4}-(KP1)_{n5}-X^2-Y^2-Z^2$;

Formula 10B $=Z^1-Y^1-X^1-(Aib)_{n1}-(Xaa^1)_{n2}-(KP)_{n3}-(Xaa^2)_{n4}-(KP1)_{n5}-(Xaa^3)_{n6}-X^2-Y^2-Z^2$;

Formula 11B $=Z^1-Y^1-X^1-(Aib)_{n1}-(Xaa^1)_{n2}-(KP)_{n3}-(Xaa^2)_{n4}-(KP1)_{n5}-(Xaa^3)_{n6}$;

Formula 12B $=(Aib)_{n1}-(Xaa^1)_{n2}-(KP)_{n3}-(Xaa^2)_{n4}-(KP1)_{n5}-(Xaa^3)_{n6}-X^2-Y^2-Z^2$;

Formula 10C $=Z^1-Y^1-X^1-(Xaa^4)_{n7}-(Aib)_{n1}-(Xaa^1)_{n2}-(KP)_{n3}-(Xaa^2)_{n4}-(KP1)_{n5}-X^2-Y^2-Z^2$;

Formula 11C $=Z^1-Y^1-X^1-(Xaa^4)_{n7}-(Aib)_{n1}-(Xaa^1)_{n2}-(KP)_{n3}-(Xaa^2)_{n4}-(KP1)_{n5}$; and Formula 12C $=(Xaa^4)_{n7}-(Aib)_{n1}-(Xaa^1)_{n2}-(KP)_{n3}-(Xaa^2)_{n4}-(KP1)_{n5}-X^2-Y^2-Z^2$.

10. The cell-targeting compound of claim 4, further comprising:
   at least one cargo moiety linked to the one or more peptides.

11. The cell-targeting compound of claim 4, wherein the at least one targeting moiety is linked to the one or more peptides through a branched linker.

12. The cell-targeting moiety of claim 11, wherein a first arm of the branched linker is linked to a specific targeting moiety and a second arm of the branched linker is linked to a general targeting moiety.

13. The cell targeting moiety of claim 12, wherein the specific targeting moiety is specific to a protein or portion thereof that is associated with a cell membrane and the general targeting moiety generally associates with the cell membrane.

14. The cell targeting moiety of claim 13, wherein the specific targeting moiety is an antibody, or fragment thereof, and the general targeting moiety is a lipid or a cholesterol or cholesterol derivative.

15. A cell-targeting compound comprising:
   one or more peptides having a conformationally-constraining portion, and a kinked portion linked through a peptide linker to the conformationally-constraining portion that conformationally constrains the kinked portion, the kinked portion, peptide linker and conformationally-constraining portion includes the peptide sequence of claim 3; and
   at least one targeting moiety linked to an end of the one or more peptides.

16. The cell-targeting compound of claim 15, wherein at least one targeting moiety is on the C-terminus of the peptide.

17. The cell-targeting compound of claim 15, wherein at least one targeting moiety is on the N-terminus of the peptide.

18. The cell-targeting compound of claim 15, comprising one of Formulae 2-2C, 3-3C, or 4-4C, wherein:
   ED-KP is an endosomal-disrupting kinked peptide having one or more amino acids independently selected from proline and glycine;
   CC-Peptide includes a peptide having one or more 2-aminoisobutyric acid residues that conformationally-constrains the ED-KP;
   Peptide independently includes natural, unnatural, essential or non-essential aromatic, aliphatic, or other amino acids, or having L or D configuration;
   Xaa, $Xaa^1$, and $Xaa^2$ are independently one or more natural or non-natural amino acids, essential amino acids, or non-essential amino acids, or amino acids having L or D configuration;
   L1 and L2 are independently linkers;
   n1 and n3 are independently an integer greater than 0 and less than 50;
   n2 and n4 are independently 0-50;
   $Z_1$ and $Z^2$ are independently a targeting moiety, cargo moiety, or nothing, wherein at least one is a targeting moiety;
   $Y^1$ and $Y^2$ are independently nothing or a linker, or a linker having a cargo moiety; and
   $Y^1$ and $X^2$ are independently nothing, a coupling group, one or more beta-alanine residues, or a polypeptide, Formula 2 = $Z^1$—$Y^1$—$X^1$—(CC-Peptide)$_{n1}$-(Peptide)$_{n2}$-(ED-KP)$_{n3}$-(Peptide)$_{n4}$-$X^2$—$Y^2$—$Z^2$;

Formula 2A = $Z^1$—$Y^1$—$X^1$—(CC-Peptide)$_1$-(L1)$_{n2}$-(ED-KP)$_{n3}$-(L2)$_{n4}$-$X^1$—$Y^2$—$Z^2$;

Formula 2B = $Z^1$—$Y^1$—$X^1$—(CC-Peptide)$_{n1}$-(Xaa)$_{n2}$-(ED-KP)$_{n3}$-(Xaa)$_{n4}$-$X^2$—$Y^2$—$Z^2$;

Formula 2C = $Z^1$—$Y^1$—$X^1$—(CC-Peptide)$_{n1}$-(Xaa$^1$)$_{n2}$-(ED-KP)$_{n3}$-(Xaa$^2$)$_{n4}$-$X^2$—$Y^2$—$Z^2$;

Formula 3 = $Z^1$—$Y^1$—$X^1$—(CC-Peptide)$_{n1}$-(Peptide)$_{n2}$-(ED-KP)$_{n3}$-(Peptide)$_{n4}$;

Formula 3A = $Z^1$—$Y^1$—$X^1$—(CC-Peptide)$_{n1}$-(L1)$_{n2}$-(ED-KP)$_{n3}$-(L2)$_{n4}$;

Formula 3B = $Z^1$—$Y^1$—$X^1$—(CC-Peptide)$_{n1}$-(Xaa)$_{n2}$-(ED-KP)$_{n3}$-(Xaa)$_{n4}$;

Formula 3C = $Z^1$—$Y^1$—$X^1$—(CC-Peptide)$_{n1}$-(Xaa$^1$)$_{n2}$-(ED-KP)$_{n3}$-(Xaa$^2$)$_{n4}$;

Formula 4 = (CC-Peptide)$_{n1}$-(Peptide)$_{n2}$-(ED-KP)$_{n3}$-(Peptide)$_{n4}$-$X^2$—$Y^2$—$Z^2$;

Formula 4A = (CC-Peptide)$_{n1}$-(L1)$_{n2}$-(ED-KP)$_{n3}$-(L1)$_{n4}$-$X^2$—$Y^2$—$Z^2$;

Formula 4B = (CC-Peptide)$_{n1}$-(Xaa)$_{n2}$-(ED-KP)$_{n3}$-(Xaa)$_{n4}$-$X^2$—$Y^2$—$Z^2$; and Formula 4C = (CC-Peptide)$_{n1}$-(Xaa$^1$)$_{n2}$-(ED-KP)$_{n3}$-(Xaa$^2$)$_{n4}$-$X^2$—$Y^2$—$Z^2$.

19. The cell-targeting compound of claim 15, comprising one of Formulae 6-6C, 7-7C, or 8-8C, wherein:
   ED-KP is an endosomal-disrupting kinked peptide having one or more amino acids independently selected from proline and glycine;
   CCM includes a moiety having one or more 2-aminoisobutyric acid residues that conformationally constrains the ED-KP;
   Peptide independently includes natural, unnatural, essential or non-essential aromatic, aliphatic, or other amino acids, or having L or D configuration;
   Xaa, $Xaa^1$, and $Xaa^2$ are independently one or more natural or non-natural amino acids, essential amino acids, or non-essential amino acids, or amino acids having L or D configuration;
   L1 and L2 are independently linkers;
   n1 and n3 are independently an integer greater than 0 and less than 50;
   n2 and n4 are independently 0-50;
   $Z^1$ and $Z^2$ are independently a targeting moiety, cargo moiety, or nothing, wherein at least one is a targeting moiety;
   $Y^1$ and $Y^2$ are independently nothing or a linker, or a linker having a cargo moiety; and
   $X^1$ and $X^2$ are independently nothing, a coupling group, one or more beta-alanine residues, or a polypeptide, Formula 6 = $Z^1$—$Y^1$—$X^1$—(CCM)$_{n1}$-(Peptide)$_{n2}$-(ED-KP)$_{n3}$-(Peptide)$_{n4}$-$X^2$—$Y^2$—$Z^2$;

Formula 6A = $Z^1$—$Y^1$—$X^1$—(CCM)$_{n1}$-(L1)$_{n2}$-(ED-KP)$_{n3}$-(L2)$_{n4}$-$X^2$—$Y^2$—$Z^2$;

Formula 6B = $Z^1$—$Y^1$—$X^1$—(CCM)$_{n1}$-(Xaa)$_{n2}$-(ED-KP)$_{n3}$-(Xaa)$_{n4}$-$X^2$—$Y^2$—$Z^2$;

Formula 6C = $Z^1$—$Y^1$—$X^1$—(CCM)$_{n1}$-(Xaa$^1$)$_{n2}$-(ED-KP)$_{n3}$-(Xaa$^2$)$_{n4}$-$X^2$—$Y^2$—$Z^2$;

Formula 7 = $Z^1$—$Y^1$—$X^1$—(CCM)$_{n1}$-(Peptide)$_{n2}$-(ED-KP)$_{n3}$-(Peptide)$_{n4}$;

Formula 7A = $Z^1$—$Y^1$—$X^1$—(CCM)$_{n1}$-(L1)$_{n2}$-(ED-KP)$_{n3}$-(L2)$_{n4}$;

Formula 7B = $Z^1-Y^1-X^1-(CCM)_{n1}-(Xaa)_{n2}-(ED-KP)_{n3}-(Xaa)_{n4}$;

Formula 7C = $Z^1-Y^1-X^1-CCM)_{n1}-(Xaa^1)_{n2}-(ED-KP)_{n3}-(Xaa^2)_{n4}$;

Formula 8 = $(CCM)_{n1}-(Peptide)_{n2}-(ED-KP)_{n3}-(Peptide)_{n4}-X^2-Y^2-Z^2$;

Formula 8A = $(CCM)_{n1}-(L1)_{n2}-(ED-KP)_{n3}-(L2)_{n4}-X^2-Y^2-Z^2$;

Formula 8B = $(CCM)_{n1}-(Xaa)_{n2}-(ED-KP)_{n3}-(Xaa)_{n4}-X^2-Y^2-Z^2$; and

Formula 8C = $(CCM)_{n1}-(Xaa^1)_{n2}-(ED-KP)_{n3}-(Xaa^2)_{n4}-X^2-Y^2-Z^2$.

20. The cell-targeting compound of claim 15, comprising one of Formulae 10-10C, 11-11C, or 12-12C wherein:
KP and KP1 are independently one or more amino acids independently selected from proline and glycine that can cause the peptide to kink;
Aib is a 2-aminoisobutyric acid residue;
Xaa, Xaa$^1$, and Xaa$^2$ are independently one or more natural or non-natural amino acids, essential amino acids, or non-essential amino acids, or amino acids having L or D configuration;
$Z^1$ and $Z^2$ are independently a targeting moiety, cargo moiety, or nothing, wherein at least one is a targeting moiety;
$Y^1$ and $Y^2$ are independently nothing or a linker, or a linker having a cargo moiety;
$X^1$ and $X^2$ are independently nothing, a coupling group, one or more beta-alanine residues, or a polypeptide; and
n1 and n3 are independently an integer greater than 0 and less than or equal to 50;
n2 n4, n5, n6, and n7 are independently 0-50, Formula 10 = $Z^1-Y^1-X^1-(Aib)_{n1}-(Xaa^1)_{n2}-(KP)_{n3}-(Xaa^2)_{n4}-X^2-Y^2-Z^2$;

Formula 11 = $Z^1-Y^1-X^1-(Aib)_{n1}-(Xaa^1)_{n2}-(KP)_{n3}-(Xaa^2)_{n4}$;

Formula 12 = $(Aib)_{n1}-(Xaa^1)_{n2}-(KP)_{n3}-(Xaa^2)_{n4}-X^2-Y^2-Z^2$;

Formula 10A = $Z^1-Y^1-X^1-(Aib)_{n1}-(Xaa^1)_{n2}-(KP)_{n3}-(Xaa^2)_{n4}-(KP1)_{n5}-X^2-Y^2-Z^2$;

Formula 11A = $Z^1-Y^1-X^1-(Aib)_{n1}-(Xaa^1)_{n2}-(KP)_{n3}-(Xaa^2)_{n4}-(KP1)_{n5}$;

Formula 12A = $(Aib)_{n1}-(Xaa^1)_{n2}-(KP)_{n3}-(Xaa^2)_{n4}-(KP1)_{n5}-X^2-Y^2-Z^2$;

Formula 10B = $Z^1-Y^1-X^1-(Aib)_{n1}-(Xaa^1)_{n2}-(KP)_{n3}-(Xaa^2)_{n4}-(KP1)_{n5}-(Xaa^3)_{n6}-X^2-Y^2-Z^2$;

Formula 11B = $Z^1-Y^1-X^1-(Aib)_{n1}-(Xaa^1)_{n2}-(KP)_{n3}-(Xaa^2)_{n4}-(KP1)_{n5}-(Xaa^3)_{n6}$;

Formula 12B = $(Aib)_{n1}-(Xaa^1)_{n2}-(KP)_{n3}-(Xaa^2)_{n4}-(KP1)_{n5}-(Xaa^3)_{n6}-X^2-Y^2-Z^2$;

Formula 10C = $Z^1-Y^1-X^1-(Xaa^4)_{n7}-(Aib)_{n1}-(Xaa^1)_{n2}-(KP)_{n3}-(Xaa^2)_{n4}-(KP1)_{n5}-X^2-Y^2-Z^2$;

Formula 11C = $Z^1-Y^1-X^1-(Xaa^4)_{n7}-(Aib)_{n1}-(Xaa^1)_{n2}-(KP)_{n3}-(Xaa^2)_{n4}-(KP1)_{n5}$; and Formula 12C = $(Xaa^4)_{n7}-(Aib)_{n1}-(Xaa^1)_{n2}-(KP)_{n3}-(Xaa^2)_{n4}-(KP1)_{n5}-X^2-Y^2-Z^2$.

21. The cell-targeting compound of claim 15, further comprising:
at least one cargo moiety linked to the one or more peptides.

22. The cell-targeting compound of claim 15, wherein the at least one targeting moiety is linked to the one or more peptides through a branched linker.

23. The cell-targeting moiety of claim 22, wherein a first arm of the branched linker is linked to a specific targeting moiety and a second arm of the branched linker is linked to a general targeting moiety.

24. The cell targeting moiety of claim 23, wherein the specific targeting moiety is specific to a protein or portion thereof that is associated with a cell membrane and the general targeting moiety generally associates with the cell membrane.

25. The cell targeting moiety of claim 24, wherein the specific targeting moiety is an antibody, or fragment thereof, and the general targeting moiety is a lipid or cholesterol derivative.

\* \* \* \* \*

SEQUENCE LISTING

```
<160> NUMBER OF SEQ ID NOS: 97

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<223> OTHER INFORMATION: C-term CONH2

<400> SEQUENCE: 1

Glu Glu Xaa Xaa Ser Ser Ala Trp Trp Ser Tyr Trp Pro Pro Val Ala
1               5                   10                  15

<210> SEQ ID NO 2
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Aib

<400> SEQUENCE: 2

Xaa Xaa Xaa Xaa
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Tyr Ala Tyr Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Trp Ala Tyr Trp
1               5

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<223> OTHER INFORMATION: C-term CONH2

<400> SEQUENCE: 5

Glu Glu Xaa Xaa Ala Ala Ala Trp Trp Ala Tyr Trp Pro Pro Val Ala
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction
      product or derivative thereof, which can be considered
      a nonstandard amino acid
```

```
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<223> OTHER INFORMATION: C-term CONH2

<400> SEQUENCE: 6

Xaa Glu Glu Xaa Ser Ser Ala Trp Trp Ser Tyr Trp Pro Pro Val Ala
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<223> OTHER INFORMATION: C-term CONH2

<400> SEQUENCE: 7

Xaa Glu Glu Xaa Ala Ala Ala Trp Trp Ala Tyr Trp Pro Pro Val Ala
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<223> OTHER INFORMATION: C-term CONH2

<400> SEQUENCE: 8

Xaa Glu Glu Xaa Xaa Ala Ala Ala Trp Trp Ala Tyr Trp Pro Pro Val
1               5                   10                  15

Ala

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
                    peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 9

Xaa Glu Glu Xaa Xaa Xaa Xaa Trp Trp Ala Tyr Trp Pro Pro Val Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(6)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 10

Xaa Glu Glu Xaa Xaa Xaa Trp Trp Ala Tyr Trp Pro Pro Val Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
```

-continued

```
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 11

Xaa Glu Glu Xaa Xaa Xaa Xaa Trp Trp Ala Tyr Trp Pro Pro Val
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic
      acid or 2-aminoisobutyric acid or Aib amino acid or
      reaction product or derivative thereof, which can be
      considered a nonstandard amino acid
<220> FEATURE:
<223> OTHER INFORMATION: C-term CONH2

<400> SEQUENCE: 12

Xaa Glu Glu Xaa Xaa Xaa Xaa Ala Trp Ala Tyr Trp Pro Pro Val Ala
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
```

```
       2-amino-2-methylpropanoic acid or 2-aminoisobutyric acid or Aib
       amino acid or reaction product or derivative thereof, which can be
       considered a nonstandard amino acid
<220> FEATURE:
<223> OTHER INFORMATION: C-term CONH2

<400> SEQUENCE: 13

Xaa Glu Glu Xaa Xaa Xaa Xaa Trp Ala Ala Tyr Trp Pro Pro Val Ala
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 14

Xaa Glu Glu Xaa Xaa Xaa Xaa Trp Trp Ala Ala Trp Pro Pro Val Ala
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 15

Xaa Glu Glu Xaa Xaa Xaa Xaa Trp Trp Ala Tyr Ala Pro Pro Val Ala
```

```
<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 16

Xaa Glu Glu Xaa Xaa Xaa Xaa Trp Trp Ala Tyr Trp Ala Pro Val Ala
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 17

Xaa Glu Glu Xaa Xaa Xaa Xaa Trp Trp Ala Tyr Trp Pro Ala Val Ala
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 18

Xaa Glu Glu Xaa Xaa Xaa Xaa Trp Trp Ala Tyr Trp Pro Pro Ala Ala
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 19

Xaa Glu Glu Xaa Xaa Xaa Xaa Trp Trp Ala Trp Trp Pro Pro Val Ala
1               5                   10                  15

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
```

```
<222> LOCATION: (4)..(4)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (5)..(8)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 20

Xaa Glu Glu Xaa Xaa Xaa Xaa Xaa Trp Trp Ala Tyr Trp Pro Pro Val
1               5                   10                  15

Ala

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 21

Xaa Glu Glu Xaa Xaa Xaa Xaa Xaa Xaa Trp Trp Ala Tyr Trp Pro Pro
1               5                   10                  15

Val Ala

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
```

```
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 22

Xaa Glu Glu Xaa Xaa Xaa Xaa Xaa Xaa Phe Phe Ala Phe Phe Pro Pro
1               5                   10                  15

Val Ala

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 23

Xaa Glu Glu Xaa Xaa Xaa Xaa Xaa Xaa Tyr Tyr Ala Tyr Tyr Pro Pro
1               5                   10                  15

Val Ala

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
``` considered a nonstandard amino acid
<220> FEATURE:
<223> OTHER INFORMATION: C-term CONH2

<400> SEQUENCE: 24

Xaa Glu Glu Xaa Xaa Xaa Xaa Xaa Xaa Tyr Tyr Tyr Tyr Tyr Pro Pro
1               5                   10                  15

Val Ala

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
      Epsilon- Ahx amino acid or reaction product or derivative thereof,
      which can be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 25

Xaa Glu Glu Xaa Xaa Xaa Xaa Xaa Xaa Tyr Tyr Ala Tyr Tyr Pro Pro
1               5                   10                  15

Val Val

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 26

Xaa Glu Glu Xaa Xaa Xaa Xaa Xaa Xaa Trp Trp Ala Tyr Trp Pro Pro
1               5                   10                  15

Val Ala

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 27

Xaa Glu Glu Xaa Xaa Xaa Xaa Xaa Xaa Trp Trp Ala Tyr Trp Pro Pro
1               5                   10                  15

Val Ala Ala

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 28

Xaa Glu Glu Xaa Xaa Xaa Xaa Xaa Xaa Tyr Tyr Ala Tyr Tyr Pro Pro
1               5                   10                  15

Val Val

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 29

Xaa Glu Glu Xaa Xaa Xaa Xaa Xaa Xaa Tyr Tyr Tyr Tyr Tyr Pro Pro
1               5                   10                  15

Val Val

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: (S)-2-aminopent-4-ynamide or
      (S)-2-aminopent-4-ynoic acid or vinylglycine or reaction product
      or derivative thereof, which can be considered a nonstandard amino
      acid
<220> FEATURE:
<221> NAME/KEY: MOD_RES
<222> LOCATION: (5)..(6)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (7)..(10)
<223> OTHER INFORMATION: 2-amino-2-methylpropanamide or 2-amino-2-methylpropanoic acid or 2-aminoisobutyric acid or Aib
        amino acid or reaction product or derivative thereof, which can be
        considered a nonstandard amino acid
<220> FEATURE:
<223> OTHER INFORMATION: C-term CONH2

<400> SEQUENCE: 30

Xaa Glu Glu Xaa Xaa Xaa Xaa Xaa Xaa Xaa Tyr Tyr Ala Tyr Tyr Pro
1               5                   10                  15

Pro Val Val

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: (S)-2-aminopent-4-ynamide or
      (S)-2-aminopent-4-ynanoic
      acid or vinylglycine or reaction product or derivative
      thereof, which can be considered a nonstandard amino acid
<220> FEATURE:
<221> NAME/KEY: MOD_RES
<222> LOCATION: (5)..(6)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (7)..(10)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 31

Xaa Glu Glu Xaa Xaa Xaa Xaa Xaa Xaa Xaa Trp Trp Ala Tyr Trp Pro
1               5                   10                  15

Pro Val Ala

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG

```
    amino acid or reaction product or derivative thereof, which can be
    considered a nonstandard amino acid
<220> FEATURE:
<221> NAME/KEY: MOD_RES
<222> LOCATION: (6)..(9)
<223> OTHER INFORMATION: 2-amino-2-methylpropanamide or
    2-amino-2-methylpropanoic acid or 2-aminoisobutyric acid or Aib
    amino acid or reaction product or derivative thereof, which can be
    considered a nonstandard amino acid
<220> FEATURE:
<223> OTHER INFORMATION: C-term CONH2

<400> SEQUENCE: 32

Xaa Glu Glu Xaa Xaa Xaa Xaa Xaa Xaa Trp Trp Ala Tyr Trp Pro Pro
1               5                   10                  15

Val Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (1)..(1)
<223> OTHER INFORMATION: 3-aminopropanamide or 3-aminopropanoic acid or
    reaction product or derivative thereof, which can be considered
    a nonstandard amino acid
<220> FEATURE:
<221> NAME/KEY: MOD_RES
<222> LOCATION: (2)..(2)
<223> OTHER INFORMATION: (S)-2-aminopent-4-ynamide or
    (S)-2-aminopent-4-ynanoic acid or vinylglycine or reaction product
    or derivative thereof, which can be considered a nonstandard amino
    acid
<220> FEATURE:
<221> NAME/KEY: MOD_RES
<222> LOCATION: (3)..(4)
<223> OTHER INFORMATION:
    3-(2-(2-(2-aminoethoxy)ethoxy)ethoxy)propanamide or
    3-(2-(2-(2-aminoethoxy)ethoxy)ethoxy)propanoic acid or mini-PEG
    amino acid or reaction product or derivative thereof, which can be
    considered a nonstandard amino acid
<220> FEATURE:
<221> NAME/KEY: MOD_RES
<222> LOCATION: (5)..(8)
<223> OTHER INFORMATION: 2-amino-2-methylpropanamide or
    2-amino-2-methylpropanoic acid or 2-aminoisobutyric acid or Aib
    amino acid or reaction product or derivative thereof, which can be
    considered a nonstandard amino acid
<220> FEATURE:
<223> OTHER INFORMATION: C-term CONH2

<400> SEQUENCE: 33

Xaa Xaa Xaa Xaa Xaa Xaa Xaa Xaa Trp Trp Ala Tyr Trp Pro Pro Val
1               5                   10                  15

Ala

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (1)..(1)
<223> OTHER INFORMATION: 3-aminopropanamide or 3-aminopropanoic acid or
    reaction product or derivative thereof, which can be considered
    a nonstandard amino acid
```

```
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 34

Xaa Glu Glu Xaa Xaa Xaa Xaa Xaa Xaa Trp Trp Ala Tyr Trp Pro Pro
1               5                   10                  15

Val Ala

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: (S)-2-aminopent-4-ynamide or
      (S)-2-aminopent-4-ynanoic acid or vinylglycine or reaction product
      or derivative thereof, which can be considered a nonstandard amino
      acid
<220> FEATURE:
<221> NAME/KEY: MOD_RES
<222> LOCATION: (5)..(6)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (7)..(10)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 35

Xaa Glu Glu Xaa Xaa Xaa Xaa Xaa Xaa Xaa Trp Trp Ala Tyr Trp Pro
1               5                   10                  15

Pro Val Ala

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: (S)-2-aminopent-4-ynamide or
      (S)-2-aminopent-4-ynanoic acid or vinylglycine or reaction product
      or derivative thereof, which can be considered a nonstandard amino
      acid
<220> FEATURE:
<221> NAME/KEY: MOD_RES
<222> LOCATION: (5)..(6)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (7)..(10)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 36

Xaa Glu Glu Xaa Xaa Xaa Xaa Xaa Xaa Xaa Trp Trp Ala Tyr Trp Pro
1               5                   10                  15

Pro Val Val

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: (S)-2-aminopent-4-ynamide or
      (S)-2-aminopent-4-ynanoic acid or vinylglycine or reaction product
      or derivative thereof, which can be considered a nonstandard amino
      acid
<220> FEATURE:
<221> NAME/KEY: MOD_RES
<222> LOCATION: (5)..(6)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (7)..(10)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 37
```

```
Xaa Glu Glu Xaa Xaa Xaa Xaa Xaa Xaa Xaa Trp Trp Ala Tyr Tyr Pro
1               5                   10                  15

Pro Val Val

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: (S)-2-aminopent-4-ynamide or
      (S)-2-aminopent-4-ynanoic acid or vinylglycine or reaction product
      or derivative thereof, which can be considered a nonstandard amino
      acid
<220> FEATURE:
<221> NAME/KEY: MOD_RES
<222> LOCATION: (5)..(6)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (7)..(10)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 38

Xaa Glu Glu Xaa Xaa Xaa Xaa Xaa Xaa Xaa Tyr Tyr Ala Tyr Tyr Pro
1               5                   10                  15

Pro Val Val

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 39

Ser Ser Ala Trp Trp Ser Tyr Trp Pro Pro Val Ala
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<223> OTHER INFORMATION: C-term CONH2

<400> SEQUENCE: 40

Ala Ala Ala Trp Trp Ala Tyr Trp Pro Pro Val Ala
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(3)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 41

Xaa Xaa Xaa Trp Trp Ala Tyr Trp Pro Pro Val Ala
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 42

Xaa Xaa Xaa Xaa Trp Trp Ala Tyr Trp Pro Pro Val Ala
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 43
```

-continued

```
Xaa Xaa Xaa Xaa Trp Trp Ala Tyr Trp Pro Pro Val Ala
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 44

Xaa Xaa Xaa Xaa Trp Trp Ala Tyr Trp Pro Pro Val Val
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 45

Xaa Xaa Xaa Xaa Ala Trp Ala Tyr Trp Pro Pro Val Val
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 46

Xaa Xaa Xaa Xaa Trp Ala Ala Tyr Trp Pro Pro Val Val
1               5                   10
```

```
<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 47

Xaa Xaa Xaa Xaa Trp Trp Ala Ala Trp Pro Pro Val Val
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 48

Xaa Xaa Xaa Xaa Trp Trp Ala Tyr Ala Pro Pro Val Val
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 49

Xaa Xaa Xaa Xaa Trp Trp Ala Tyr Trp Ala Pro Val Val
1               5                   10

<210> SEQ ID NO 50
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 50

Xaa Xaa Xaa Xaa Trp Trp Ala Tyr Trp Pro Ala Val Val
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 51

Xaa Xaa Xaa Xaa Trp Trp Ala Tyr Trp Pro Pro Ala Val
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 52

Xaa Xaa Xaa Xaa Tyr Trp Ala Trp Trp Pro Pro Val Val
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 53

Xaa Xaa Xaa Xaa Trp Tyr Ala Trp Trp Pro Pro Val Val
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 54

Xaa Xaa Xaa Xaa Trp Trp Ala Trp Tyr Pro Pro Val Val
1               5                   10

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60
```

```
<400> SEQUENCE: 60

000

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(5)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 61

Xaa Xaa Xaa Xaa Xaa Trp Trp Ala Tyr Trp Pro Pro Val Ala
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 62

Xaa Xaa Xaa Xaa Tyr Tyr Ala Tyr Tyr Pro Pro Val Val
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 63

Xaa Xaa Xaa Xaa Trp Trp Ala Tyr Trp Pro Pro Val Val
1               5                   10
```

```
<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 64

Xaa Xaa Xaa Xaa His His Ala His His Pro Pro Val Val
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 65

Xaa Xaa Xaa Xaa Trp Trp Ala Tyr Trp Pro Pro Val Leu
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 66

Xaa Xaa Xaa Xaa Trp Trp Ala Tyr Trp Pro Pro Leu Val
1               5                   10

<210> SEQ ID NO 67
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 67

Xaa Xaa Xaa Xaa Trp Trp Ala Tyr Trp Pro Pro Leu Leu
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 68

Xaa Xaa Xaa Xaa Trp Trp Gly Tyr Trp Pro Pro Val Ala
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 69

Xaa Xaa Xaa Xaa Tyr Tyr Ala Tyr Tyr Pro Pro Val Val
1               5                   10

<210> SEQ ID NO 70

<400> SEQUENCE: 70

000
```

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
guacggaaua gauaauuaau t                                      21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uuaauuaucu auuccguacu u                                      21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
guacggaaua gauaauuaau u                                      21

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:

-continued

```
<223> OTHER INFORMATION: N-term Ac
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term NH2

<400> SEQUENCE: 78

Xaa Xaa Xaa Xaa Trp Trp Ala Trp Tyr Pro Pro Val Val
1               5                   10

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term NH2

<400> SEQUENCE: 79

Xaa Xaa Xaa Xaa Trp Trp Ala Trp Trp Ala Trp Tyr Pro Pro Val Val
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term NH2

<400> SEQUENCE: 80

Xaa Xaa Xaa Xaa Trp Tyr Ala Trp Tyr Ala Trp Tyr Pro Pro Val Val
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term NH2

<400> SEQUENCE: 81

Xaa Xaa Xaa Xaa Ala Trp Tyr Ala Trp Tyr Trp Tyr Pro Pro Val Val
1               5                   10                  15

<210> SEQ ID NO 82
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term NH2

<400> SEQUENCE: 82

Xaa Xaa Xaa Xaa Trp Tyr Ala Trp Tyr Ala Trp Tyr Pro Pro Val Val
1               5                   10                  15

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Pacific Blue fluorophore
<220> FEATURE:
<221> NAME/KEY: MOD_RES
<222> LOCATION: (2)..(5)
<223> OTHER INFORMATION: Aib
<220> FEATURE:
<223> OTHER INFORMATION: C-term NH2

<400> SEQUENCE: 83

Gly Xaa Xaa Xaa Xaa Trp Tyr Ala Trp Tyr Ala Trp Tyr Pro Pro Val
1               5                   10                  15

Val

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term (Cholester-3-yl)oxy
<220> FEATURE:
<221> NAME/KEY: MOD_RES
<222> LOCATION: (1)..(2)
<223> OTHER INFORMATION: Beta-Ala
<220> FEATURE:
<221> NAME/KEY: MOD_RES
<222> LOCATION: (5)..(6)
<223> OTHER INFORMATION: 3-(2-(2-(2-aminoethoxy)ethoxy)ethoxy)propanyl
<220> FEATURE:
<221> NAME/KEY: MOD_RES
<222> LOCATION: (7)..(10)
<223> OTHER INFORMATION: Aib
<220> FEATURE:
<223> OTHER INFORMATION: C-term NH2

<400> SEQUENCE: 84

Xaa Xaa Glu Glu Xaa Xaa Xaa Xaa Xaa Xaa Trp Tyr Ala Trp Tyr Ala
1               5                   10                  15

Trp Tyr Pro Pro Val Val
            20

<210> SEQ ID NO 85
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term NH2

<400> SEQUENCE: 85

Xaa Xaa Xaa Xaa Tyr Tyr Ala Tyr Tyr Ala Tyr Tyr Pro Pro Val Val
1               5                   10                  15

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term
      (3-beta-Cholest-5-en-3-yl-ammonio)pentanoyl
<220> FEATURE:
<221> NAME/KEY: MOD_RES
<222> LOCATION: (3)..(4)
<223> OTHER INFORMATION: 3-(2-(2-(2-aminoethoxy)ethoxy)ethoxy)propanyl
<220> FEATURE:
<221> NAME/KEY: MOD_RES
<222> LOCATION: (5)..(8)
<223> OTHER INFORMATION: Aib
<220> FEATURE:
<223> OTHER INFORMATION: C-term NH2

<400> SEQUENCE: 86

Glu Glu Xaa Xaa Xaa Xaa Xaa Xaa Tyr Tyr Tyr Tyr Tyr Pro Pro Val
1               5                   10                  15

Val

<210> SEQ ID NO 87
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term (Cholester-3-yl)oxy
<220> FEATURE:
<221> NAME/KEY: MOD_RES
<222> LOCATION: (1)..(2)
<223> OTHER INFORMATION: Beta-Ala
<220> FEATURE:
<221> NAME/KEY: MOD_RES
<222> LOCATION: (5)..(6)
<223> OTHER INFORMATION: 3-(2-(2-(2-aminoethoxy)ethoxy)ethoxy)propanyl
<220> FEATURE:
<221> NAME/KEY: MOD_RES
<222> LOCATION: (7)..(10)
<223> OTHER INFORMATION: Aib
<220> FEATURE:
<223> OTHER INFORMATION: C-term NH2

<400> SEQUENCE: 87

Xaa Xaa Glu Glu Xaa Xaa Xaa Xaa Xaa Xaa Tyr Tyr Ala Tyr Tyr Ala
1               5                   10                  15

Tyr Tyr Pro Pro Val Val
            20

<210> SEQ ID NO 88
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term NH2

<400> SEQUENCE: 88

Xaa Xaa Xaa Xaa Tyr Trp Ala Tyr Trp Ala Tyr Trp Pro Pro Val Val
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term NH2

<400> SEQUENCE: 89

Xaa Xaa Xaa Xaa Trp Trp Ala Trp Trp Ala Trp Trp Pro Pro Val Val
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term NH2

<400> SEQUENCE: 90

Xaa Xaa Xaa Xaa Trp Trp Ala Trp Trp Ala Trp Tyr Pro Pro Val Val
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term NH2

<400> SEQUENCE: 91

Xaa Xaa Xaa Xaa Tyr Tyr Ala Tyr Tyr Ala Tyr Tyr Pro Pro Val Val
```

-continued

```
<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Aib
<220> FEATURE:
<221> NAME/KEY: MOD_RES
<222> LOCATION: (5)..(6)
<223> OTHER INFORMATION: Trp or Tyr
<220> FEATURE:
<221> NAME/KEY: MOD_RES
<222> LOCATION: (8)..(9)
<223> OTHER INFORMATION: Trp or Tyr
<220> FEATURE:
<221> NAME/KEY: MOD_RES
<222> LOCATION: (11)..(12)
<223> OTHER INFORMATION: Trp or Tyr
<220> FEATURE:
<223> OTHER INFORMATION: C-term NH2

<400> SEQUENCE: 92

Xaa Xaa Xaa Xaa Xaa Xaa Ala Xaa Xaa Ala Xaa Xaa Pro Pro Val Val
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Aib
<220> FEATURE:
<221> NAME/KEY: MOD_RES
<222> LOCATION: (5)..(6)
<223> OTHER INFORMATION: Any aromatic amino acid
<220> FEATURE:
<221> NAME/KEY: MOD_RES
<222> LOCATION: (8)..(9)
<223> OTHER INFORMATION: Any aromatic amino acid
<220> FEATURE:
<221> NAME/KEY: MOD_RES
<222> LOCATION: (11)..(12)
<223> OTHER INFORMATION: Any aromatic amino acid
<220> FEATURE:
<223> OTHER INFORMATION: C-term NH2

<400> SEQUENCE: 93

Xaa Xaa Xaa Xaa Xaa Xaa Ala Xaa Xaa Ala Xaa Xaa Pro Pro Val Val
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic amino acid, Aib or not present
<220> FEATURE:
```

```
<221> NAME/KEY: MOD_RES
<222> LOCATION: (5)..(6)
<223> OTHER INFORMATION: Any aromatic amino acid
<220> FEATURE:
<221> NAME/KEY: MOD_RES
<222> LOCATION: (8)..(9)
<223> OTHER INFORMATION: Any aromatic amino acid
<220> FEATURE:
<221> NAME/KEY: MOD_RES
<222> LOCATION: (11)..(12)
<223> OTHER INFORMATION: Any aromatic amino acid
<220> FEATURE:
<223> OTHER INFORMATION: C-term NH2

<400> SEQUENCE: 94

Xaa Xaa Xaa Xaa Xaa Xaa Ala Xaa Xaa Ala Xaa Xaa Pro Pro Val Val
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any aliphatic amino acid, Aib or not present
<220> FEATURE:
<221> NAME/KEY: MOD_RES
<222> LOCATION: (5)..(6)
<223> OTHER INFORMATION: Any aromatic amino acid
<220> FEATURE:
<221> NAME/KEY: MOD_RES
<222> LOCATION: (8)..(9)
<223> OTHER INFORMATION: Any aromatic amino acid
<220> FEATURE:
<221> NAME/KEY: MOD_RES
<222> LOCATION: (11)..(12)
<223> OTHER INFORMATION: Any aromatic amino acid
<220> FEATURE:
<221> NAME/KEY: MOD_RES
<222> LOCATION: (15)..(16)
<223> OTHER INFORMATION: Any aliphatic amino acid, Aib or not present
<220> FEATURE:
<223> OTHER INFORMATION: C-term NH2

<400> SEQUENCE: 95

Xaa Xaa Xaa Xaa Xaa Xaa Ala Xaa Xaa Ala Xaa Xaa Pro Pro Xaa Xaa
1               5                   10                  15

<210> SEQ ID NO 96
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(40)
<223> OTHER INFORMATION: Any aliphatic amino acid, Aib or not present
<220> FEATURE:
<221> NAME/KEY: MISC_FEATURE
<222> LOCATION: (1)..(10)
<223> OTHER INFORMATION: This region may encompass 1-10 amino acids
<220> FEATURE:
<221> NAME/KEY: MISC_FEATURE
<222> LOCATION: (11)..(20)
<223> OTHER INFORMATION: This region may encompass 1-10 amino acids
<220> FEATURE:
<221> NAME/KEY: MISC_FEATURE
<222> LOCATION: (21)..(30)
<223> OTHER INFORMATION: This region may encompass 1-10 amino acids
```

```
<220> FEATURE:
<221> NAME/KEY: MISC_FEATURE
<222> LOCATION: (31)..(40)
<223> OTHER INFORMATION: This region may encompass 1-10 amino acids
<220> FEATURE:
<221> NAME/KEY: MOD_RES
<222> LOCATION: (41)..(42)
<223> OTHER INFORMATION: Any aromatic amino acid
<220> FEATURE:
<221> NAME/KEY: MOD_RES
<222> LOCATION: (44)..(45)
<223> OTHER INFORMATION: Any aromatic amino acid
<220> FEATURE:
<221> NAME/KEY: MOD_RES
<222> LOCATION: (47)..(48)
<223> OTHER INFORMATION: Any aromatic amino acid
<220> FEATURE:
<221> NAME/KEY: MOD_RES
<222> LOCATION: (51)..(70)
<223> OTHER INFORMATION: Any aliphatic amino acid, Aib or not present
<220> FEATURE:
<221> NAME/KEY: MISC_FEATURE
<222> LOCATION: (51)..(60)
<223> OTHER INFORMATION: This region may encompass 1-10 amino acids
<220> FEATURE:
<221> NAME/KEY: MISC_FEATURE
<222> LOCATION: (61)..(70)
<223> OTHER INFORMATION: This region may encompass 1-10 amino acids
<220> FEATURE:
<223> OTHER INFORMATION: C-term NH2

<400> SEQUENCE: 96

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Ala Xaa Xaa Ala Xaa Xaa
        35                  40                  45

Pro Pro Xaa Xaa Xaa Xaa Xaa Xaa Xaa Xaa Xaa Xaa Xaa Xaa Xaa
        50                  55                  60

Xaa Xaa Xaa Xaa Xaa Xaa
65                  70

<210> SEQ ID NO 97
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(40)
<223> OTHER INFORMATION: Any aliphatic amino acid, Aib or not present
<220> FEATURE:
<221> NAME/KEY: MISC_FEATURE
<222> LOCATION: (1)..(10)
<223> OTHER INFORMATION: This region may encompass 1-10 amino acids
<220> FEATURE:
<221> NAME/KEY: MISC_FEATURE
<222> LOCATION: (11)..(20)
<223> OTHER INFORMATION: This region may encompass 1-10 amino acids
<220> FEATURE:
<221> NAME/KEY: MISC_FEATURE
<222> LOCATION: (21)..(30)
<223> OTHER INFORMATION: This region may encompass 1-10 amino acids
<220> FEATURE:
<221> NAME/KEY: MISC_FEATURE
<222> LOCATION: (31)..(40)
<223> OTHER INFORMATION: This region may encompass 1-10 amino acids
<220> FEATURE:
<221> NAME/KEY: MOD_RES
<222> LOCATION: (41)..(42)
```

```
<223> OTHER INFORMATION: Any aromatic amino acid
<220> FEATURE:
<221> NAME/KEY: MOD_RES
<222> LOCATION: (44)..(45)
<223> OTHER INFORMATION: Any aromatic amino acid
<220> FEATURE:
<221> NAME/KEY: MOD_RES
<222> LOCATION: (47)..(48)
<223> OTHER INFORMATION: Any aromatic amino acid
<220> FEATURE:
<221> NAME/KEY: MOD_RES
<222> LOCATION: (49)..(50)
<223> OTHER INFORMATION: Pro or Gly
<220> FEATURE:
<221> NAME/KEY: MOD_RES
<222> LOCATION: (51)..(70)
<223> OTHER INFORMATION: Any aliphatic amino acid, Aib or not present
<220> FEATURE:
<221> NAME/KEY: MISC_FEATURE
<222> LOCATION: (51)..(60)
<223> OTHER INFORMATION: This region may encompass 1-10 amino acids
<220> FEATURE:
<221> NAME/KEY: MISC_FEATURE
<222> LOCATION: (61)..(70)
<223> OTHER INFORMATION: This region may encompass 1-10 amino acids
<220> FEATURE:
<223> OTHER INFORMATION: C-term NH2

<400> SEQUENCE: 97

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Ala Xaa Xaa Ala Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa
65                  70
```